US012742775B2

(12) United States Patent
Umetsu et al.

(10) Patent No.: US 12,742,775 B2
(45) Date of Patent: Sep. 22, 2026

(54) INFORMATION PROCESSING APPARATUS, INFORMATION PROCESSING SYSTEM, INFORMATION PROCESSING METHOD, AND PROGRAM

(71) Applicant: Sony Group Corporation, Tokyo (JP)

(72) Inventors: Tomoyuki Umetsu, Tokyo (JP); Kenji Yamane, Kanagawa (JP)

(73) Assignee: Sony Group Corporation, Tokyo (JP)

( * ) Notice: Subject to any disclaimer, the term of this patent is extended or adjusted under 35 U.S.C. 154(b) by 777 days.

(21) Appl. No.: 18/016,274

(22) PCT Filed: Jun. 17, 2021

(86) PCT No.: PCT/JP2021/023111

§ 371 (c)(1),
(2) Date: Jan. 13, 2023

(87) PCT Pub. No.: WO2022/019016

PCT Pub. Date: Jan. 27, 2022

(65) Prior Publication Data

US 2023/0273191 A1 Aug. 31, 2023

(30) Foreign Application Priority Data

Jul. 21, 2020 (JP) ................................ 2020-124469

(51) Int. Cl.
*G01N 15/14* (2024.01)
*G01N 21/64* (2006.01)
(Continued)

(52) U.S. Cl.
CPC ........... *G01N 33/533* (2013.01); *G01N 21/64* (2013.01); *G06N 3/002* (2013.01)

(58) Field of Classification Search
None
See application file for complete search history.

(56) References Cited

U.S. PATENT DOCUMENTS 5,206,143 A 4/1993 Horan
12,209,948 B2 1/2025 Jaimes et al.
(Continued)

FOREIGN PATENT DOCUMENTS

CN 110691964 A 1/2020
EP 3 579 238 A1 12/2019
(Continued)

OTHER PUBLICATIONS

Benke, Stephan, "The Panel Design Tool", University of Zurich, Flow Cytometry Facility, Jun. 1, 2017 (Jun. 1, 2017), pp. 1-34, XP093106104.

(Continued)

*Primary Examiner* — Marcus H Taningco
(74) *Attorney, Agent, or Firm* — Wolf, Greenfield & Sacks, P.C.

(57) ABSTRACT

A main object of the present technology is to provide a technique for automatically proposing a better combination of fluorochrome-labeled antibodies.

The present technology provides an information processing apparatus including a processing unit that generates a combination list of phosphors with respect to biomolecules on the basis of expression level categories in which a plurality of biomolecules to be used for analysis of a sample is classified on the basis of expression levels in the sample, brightness categories in which a plurality of phosphors usable for the analysis of the sample is classified on the basis of brightness, and correlation information between the plurality of phosphors, in which the processing unit selects the phosphors to be allocated to the biomolecules in the combination list from phosphors belonging to a brightness category associated with an expression level category to which the biomolecules belong.

21 Claims, 42 Drawing Sheets

1

2

(51) Int. Cl.
*G01N 33/533* (2006.01)
*G06N 3/00* (2023.01)

(56) References Cited

U.S. PATENT DOCUMENTS

| | | | | |
|---|---|---|---|---|
| 2011/0204259 | A1 | 8/2011 | Rogers | |
| 2015/0099653 | A1* | 4/2015 | Battini | G01N 33/57515 506/18 |
| 2016/0025621 | A1 | 1/2016 | Kapinsky | |
| 2019/0360910 | A1 | 11/2019 | Tsuji | |
| 2021/0335450 | A1* | 10/2021 | Nakagawa | G16B 45/00 |

FOREIGN PATENT DOCUMENTS

| | | | | |
|---|---|---|---|---|
| JP | 2012529046 | A | 11/2012 | |
| JP | 2013024792 | A | 2/2013 | |
| JP | 2016-517000 | A | 6/2016 | |
| JP | 2019-203842 | A | 11/2019 | |
| JP | 2020510822 | A | 4/2020 | |
| WO | WO-2011065753 | A2 | 6/2011 | |
| WO | WO 2014/144826 | A1 | 9/2014 | |
| WO | WO-2019031048 | A1 | 2/2019 | |
| WO | WO 2019/106973 | A1 | 6/2019 | |
| WO | WO-2022019016 | A1 * | 1/2022 | G01N 15/1429 |

OTHER PUBLICATIONS

International Search Report and English translation thereof mailed Aug. 24, 2021 in connection with International Application No. PCT/JP2021/023111.

International Written Opinion and English translation thereof mailed Aug. 24, 2021 in connection with International Application No. PCT/JP2021/023111.

International Preliminary Report on Patentability and English translation thereof mailed Feb. 2, 2023 in connection with International Application No. PCT/JP2021/023111.

Extended European Search Report issued Dec. 11, 2023 in connection with European Application No. 21846215.8.

* cited by examiner

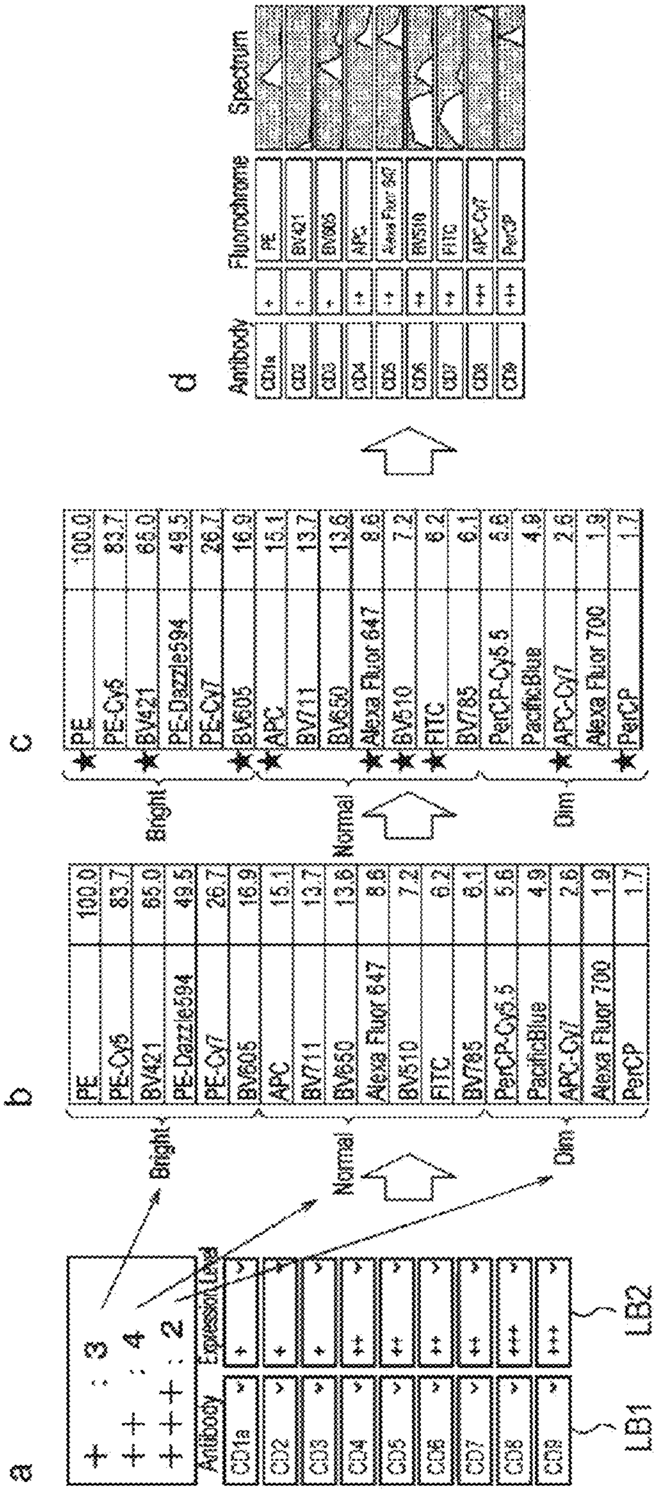

| Antibody | Expression Level |
|---|---|
| CD1a | + |
| CD2 | + |
| CD3 | + |
| CD4 | ++ |
| CD5 | ++ |
| CD6 | ++ |
| CD7 | ++ |
| CD8 | +++ |
| CD9 | +++ |

LB1 LB2 b

| | | |
|---|---|---|
| Bright | PE | 100.0 |
| | PE-Cy5 | 83.7 |
| | BV421 | 65.0 |
| | PE-Dazzle594 | 49.5 |
| | PE-Cy7 | 26.7 |
| | BV605 | 16.9 |
| Normal | APC | 15.1 |
| | BV711 | 13.7 |
| | BV650 | 13.6 |
| | Alexa Fluor 647 | 8.6 |
| | BV510 | 7.2 |
| | FITC | 6.2 |
| | BV785 | 6.1 |
| Dim | PerCP-Cy5.5 | 5.6 |
| | PacificBlue | 4.9 |
| | APC-Cy7 | 2.6 |
| | Alexa Fluor 700 | 1.9 |
| | PerCP | 1.7 |

c

| | | |
|---|---|---|
| Bright | ★PE | 100.0 |
| | PE-Cy5 | 83.7 |
| | ★BV421 | 65.0 |
| | PE-Dazzle594 | 49.5 |
| | PE-Cy7 | 26.7 |
| | ★BV605 | 16.9 |
| Normal | ★APC | 15.1 |
| | BV711 | 13.7 |
| | BV650 | 13.6 |
| | ★Alexa Fluor 647 | 8.6 |
| | ★BV510 | 7.2 |
| | ★FITC | 6.2 |
| | BV785 | 6.1 |
| Dim | PerCP-Cy5.5 | 5.6 |
| | PacificBlue | 4.9 |
| | ★APC-Cy7 | 2.6 |
| | Alexa Fluor 700 | 1.9 |
| | ★PerCP | 1.7 |

d

| Antibody | | Fluorochrome | Spectrum |
|---|---|---|---|
| CD1a | + | PE | |
| CD2 | + | BV421 | |
| CD3 | + | BV605 | |
| CD4 | ++ | APC | |
| CD5 | ++ | Alexa Fluor 647 | |
| CD6 | ++ | BV510 | |
| CD7 | ++ | FITC | |
| CD8 | +++ | APC-Cy7 | |
| CD9 | +++ | PerCP | |

FIG. 5B

| AntiBody | Fluorochrome | Clone | ISO Type | Target Species | Host Species | Catalog | Size | Company | Price | URL | Product Name |
|---|---|---|---|---|---|---|---|---|---|---|---|
| CD27 | PE | O323 | IgG1, κ | human | Mouse | 2114035 | 25 tests | sony | 17400 | https://d177r6bz0xmhgl.cloudfront.net/pub/media/pds/2114035_TDS.pdf | Anti-human CD27, |
| CD127 (IL-7Rα) | BV421 | A019D5 | IgG1, κ | human | Mouse | 2356545 | 25 tests | sony | 34400 | https://d177r6bz0xmhgl.cloudfront.net/pub/media/pds/2356545_TDS.pdf | Anti-human CD12 |
| CD19 | BV605 | HIB19 | IgG1, κ | human | Mouse | 2111215 | 25 tests | sony | 32400 | https://d177r6bz0xmhgl.cloudfront.net/pub/media/pds/2111215_TDS.pdf | Isotype Control,Mc |
| CD5 | APC | UCHT2 | IgG1, κ | human | Mouse | 2103055 | 25 tests | sony | 19800 | https://d177r6bz0xmhgl.cloudfront.net/pub/media/pds/2103055_TDS.pdf | Anti-human CD5,M |
| CD4 | BV510 | OKT4 | IgG2b, κ | human | Mouse | 2187215 | 25 tests | sony | 29800 | https://d177r6bz0xmhgl.cloudfront.net/pub/media/pds/2187215_TDS.pdf | Isotype Control,Mc |
| CD3 | PacificBlue | UCHT1 | IgG1, κ | human | Mouse | 2102085 | 100 μg | sony | 39800 | https://d177r6bz0xmhgl.cloudfront.net/pub/media/pds/2102085_TDS.pdf | Anti-human CD3,M |
| CD8a | APC-Cy7 | HIT8a | IgG1, κ | human | Mouse | 2104625 | 25 tests | sony | 22800 | https://d177r6bz0xmhgl.cloudfront.net/pub/media/pds/2104625_TDS.pdf | Anti-human CD8a, |
| CD45 | Alexa Fluor 700 | HI30 | IgG1, κ | human | Mouse | 2120115 | 25 μg | sony | 18400 | https://d177r6bz0xmhgl.cloudfront.net/pub/media/pds/2120115_TDS.pdf | Anti-human CD45, |

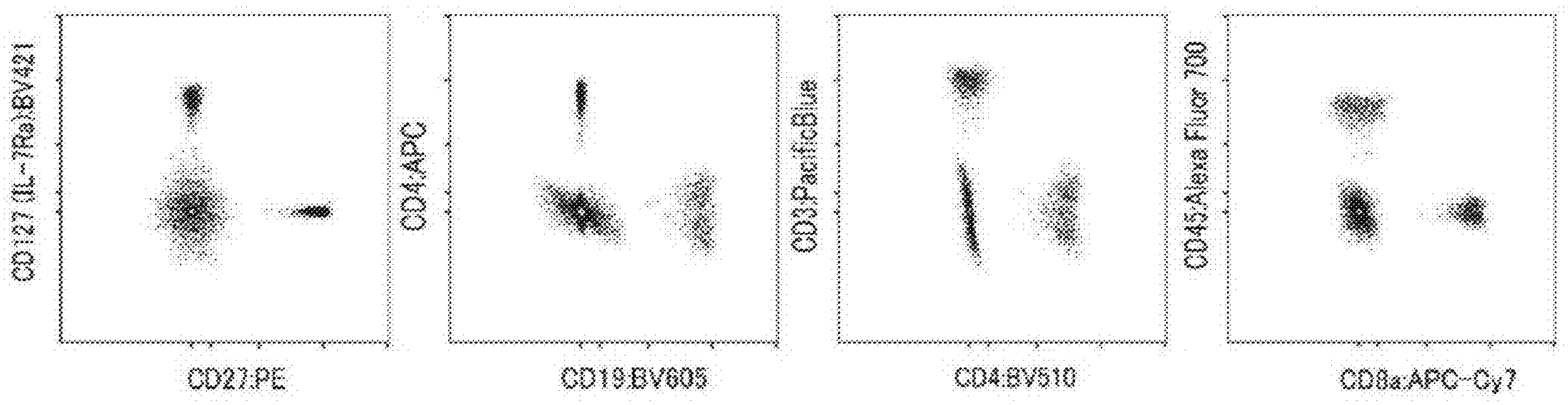

Figure 6:
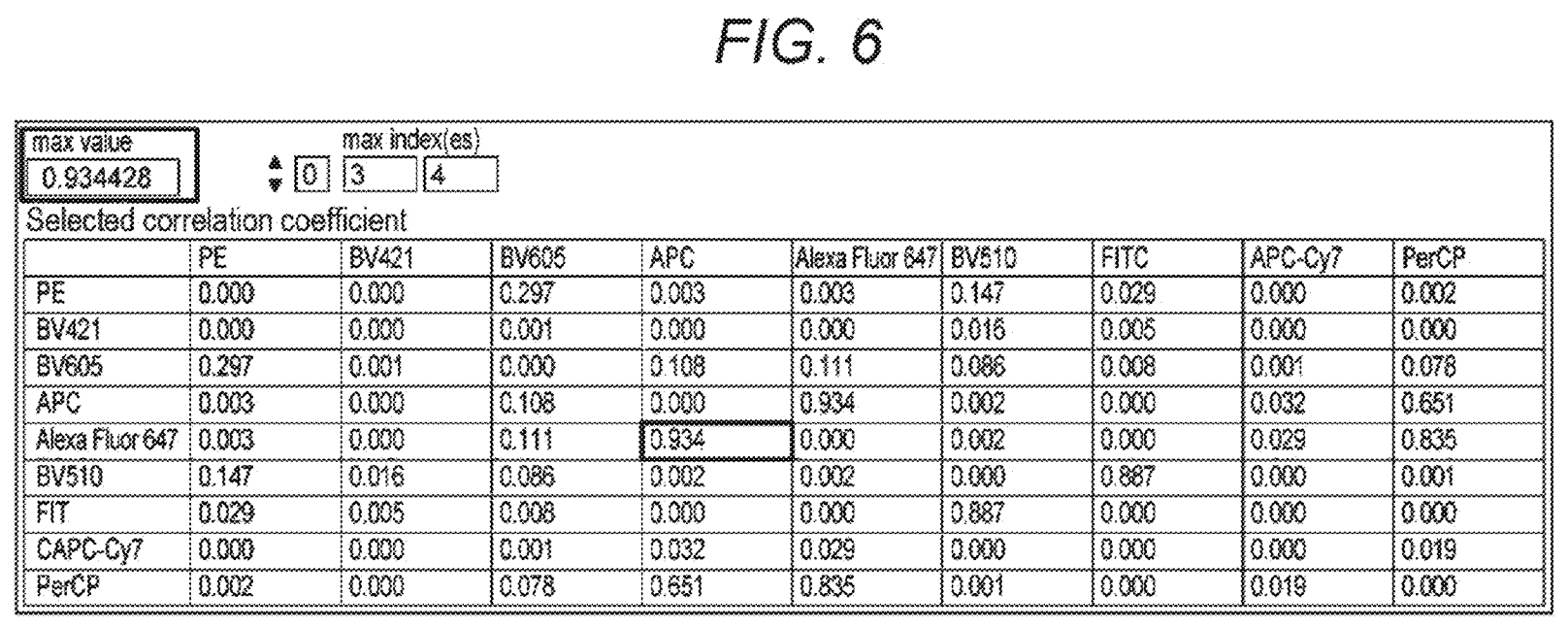

FIG. 6 max value
0.934428 max index(es)
0 3 4

Selected correlation coefficient

| | PE | BV421 | BV605 | APC | Alexa Fluor 647 | BV510 | FITC | APC-Cy7 | PerCP |
|---|---|---|---|---|---|---|---|---|---|
| PE | 0.000 | 0.000 | 0.297 | 0.003 | 0.003 | 0.147 | 0.029 | 0.000 | 0.002 |
| BV421 | 0.000 | 0.000 | 0.001 | 0.000 | 0.000 | 0.016 | 0.005 | 0.000 | 0.000 |
| BV605 | 0.297 | 0.001 | 0.000 | 0.108 | 0.111 | 0.086 | 0.008 | 0.001 | 0.078 |
| APC | 0.003 | 0.000 | 0.108 | 0.000 | 0.934 | 0.002 | 0.000 | 0.032 | 0.651 |
| Alexa Fluor 647 | 0.003 | 0.000 | 0.111 | 0.934 | 0.000 | 0.002 | 0.000 | 0.029 | 0.835 |
| BV510 | 0.147 | 0.016 | 0.086 | 0.002 | 0.002 | 0.000 | 0.887 | 0.000 | 0.001 |
| FIT | 0.029 | 0.005 | 0.008 | 0.000 | 0.000 | 0.887 | 0.000 | 0.000 | 0.000 |
| CAPC-Cy7 | 0.000 | 0.000 | 0.001 | 0.032 | 0.029 | 0.000 | 0.000 | 0.000 | 0.019 |
| PerCP | 0.002 | 0.000 | 0.078 | 0.651 | 0.835 | 0.001 | 0.000 | 0.019 | 0.000 |

| Fluorochrome | Value |
|---|---|
| ★ PE | 100.0 |
| PE-Cy5 | 83.7 |
| ★ BV421 | 65.0 |
| PE-Dazzle594 | 49.5 |
| PE-Cy7 | 26.7 |
| ★ BV605 | 16.9 |
| ★ APC | 15.1 |
| BV711 | 13.7 |
| BV650 | 13.6 |
| ★ Alexa Fluor 647 | 8.6 |
| ★ BV510 | 7.2 |
| ★ FITC | 6.2 |
| BV785 | 6.1 |
| PerCP-Cy5.5 | 5.6 |
| PacificBlue | 4.9 |
| ★ APC-Cy7 | 2.6 |
| Alexa Fluor 700 | 1.9 |
| ★ PerCP | 1.7 |

| Antibody | | Fluorochrome | Spectrum |
|---|---|---|---|
| CD1a | + | PE | |
| CD2 | + | BV421 | |
| CD3 | + | BV605 | |
| CD4 | ++ | APC | |
| CD5 | ++ | Alexa Fluor 647 | |
| CD6 | ++ | BV510 | |
| CD7 | ++ | FITC | |
| CD8 | +++ | APC-Cy7 | |
| CD9 | +++ | PerCP | |

A
PE-Cy7 spectrum(@551nm)
1.2
1
0.8
0.6
0.4
0.2
0
-0.2
B
APC-Cy7 spectrum(@628nm)
C
PE-Cy7 and APC-Cy7 spectrum (5Laser)
355nm
405nm
488nm
561nm
638nm
PE-Cy7
APC-Cy7

| name | value | | name | value |
|---|---|---|---|---|
| Alexa Fluor 532 | 750 | | PE-Cy7 | 1000 |
| Alexa Fluor 555 | 500 | | PE-Dazzle594 | 1000 |
| Alexa Fluor 594 | 1000 | | PE-eF610 | 500 |
| Alexa Fluor 647 | 1000 | | PE | 1000 |
| Alexa Fluor 700 | 1000 | | PerCP-Cy5.5 | 1000 |
| AM CA | 500 | | PerCP-eF710 | 500 |
| Am Cyan | 500 | | PerCP | 1000 |
| APC-Cy7 | 1000 | | Qdot 605 | 250 |
| APC | 1000 | | Qdot 655 | 250 |
| BUV395 | 1000 | | Qdot 705 | 250 |
| BUV496 | 750 | | Qdot 800 | 250 |
| BUV563 | 750 | | PacificBlue | 1000 |
| BUV661 | 750 | | V500 | 750 |
| BUV737 | 750 | | BB515 | 750 |
| BUV805 | 750 | | APC-R700 | 750 |
| BV421 | 1000 | | Alexa Fluor 405 | 1 |
| BV480 | 1000 | | Alexa Fluor 610 | 1 |
| BV510 | 1000 | | APC-Cy5.5 | 1 |
| BV570 | 1000 | | Cy5 | 1 |
| BV605 | 1000 | | eFluor 450 | 1 |
| BV650 | 1000 | | eFluor 506 | 1 |
| BV711 | 1000 | | eFluor 660 | 1 |
| BV750 | 750 | | Pacific Green | 1 |
| BV785 | 1000 | | Pacific Orange | 1 |
| FITC | 1000 | | PE-eF700 | 1 |
| PE-AF610 | 500 | | | |
| PE-AF700 | 500 | | | |
| PE-Cy5.5 | 1000 | | | |
| PE-Cy5 | 750 | | | |

B

In a case where Auto Restriction is ON:
Candidates of dyes to be used are narrowed down in accordance with the number of inputs under the following conditions.

Number of inputs 0 to 10: use only priority order value of 1000
11 to 20: use priority order values of 750 to 1000
21 to 30: use priority order values of 500 to 1000
31 to 40: use priority order values of 250 to 1000
41 or more: use priority order values of 0 to 1000

C

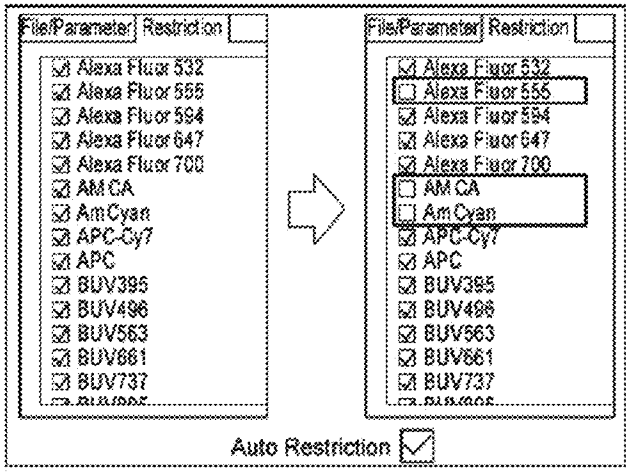

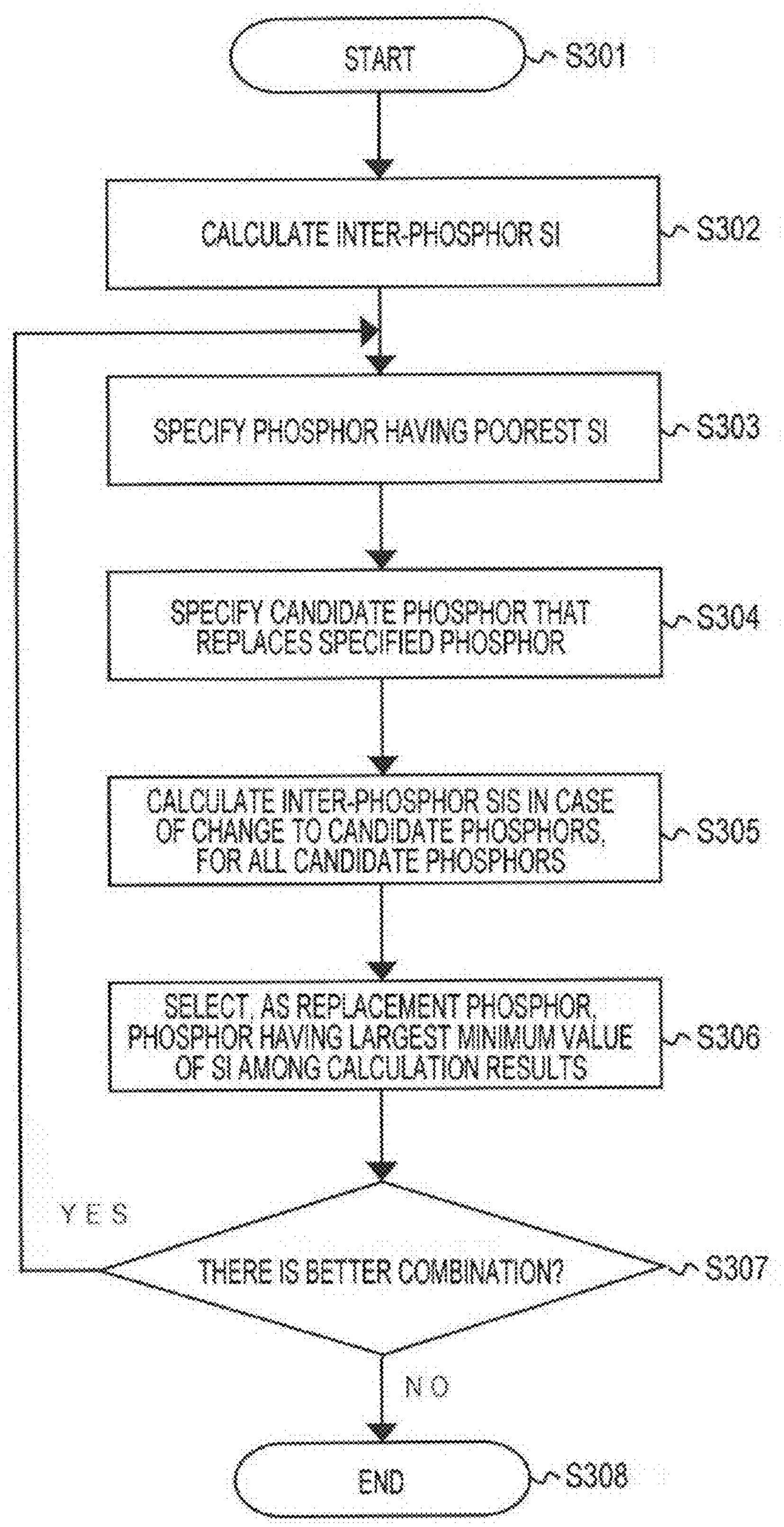

FIG. 14

START S301
CALCULATE INTER-PHOSPHOR SI S302
SPECIFY PHOSPHOR HAVING POOREST SI S303
SPECIFY CANDIDATE PHOSPHOR THAT REPLACES SPECIFIED PHOSPHOR S304
CALCULATE INTER-PHOSPHOR SIS IN CASE OF CHANGE TO CANDIDATE PHOSPHORS, FOR ALL CANDIDATE PHOSPHORS S305
SELECT, AS REPLACEMENT PHOSPHOR, PHOSPHOR HAVING LARGEST MINIMUM VALUE OF SI AMONG CALCULATION RESULTS S306
THERE IS BETTER COMBINATION? S307
YES
NO
END S308

Reagent | Stain-Index | SSM

| Nega/Posi | PE | BV421 | BV605 | APC | BV711 | FITC | BV785 | PerCP-Cy5.5 | PacificBlue | PerCP |
|---|---|---|---|---|---|---|---|---|---|---|
| PE | - | 163.2 | 26.3 | 32.5 | 37.9 | 292.3 | 61.2 | 11.2 | 476.7 | 13.1 |
| BV421 | 264.4 | - | 128.5 | 243.5 | 158.9 | 54.3 | 215.8 | 54.4 | 26.9 | 70.4 |
| BV605 | 58.3 | 36.7 | - | 15 | 16.4 | 168.2 | 32.7 | 5 | 89.6 | 5.9 |
| APC | 538.8 | 68.1 | 42.1 | - | 12.7 | 494.7 | 26.4 | 3.9 | 452.8 | 4.3 |
| BV711 | 37.3 | 22.3 | 462.7 | 44.9 | - | 165.2 | 12.7 | | 59.4 | 4.3 |
| FITC | 63.3 | 303.7 | 77 | 84.3 | 108.3 | - | 187.9 | 30.6 | 442.6 | 36.6 |
| BV786 | 41.2 | 30.2 | 486.4 | 18.2 | 52.8 | 128.7 | - | 20.9 | 65.7 | 31.9 |
| PerCP-Cy5.5 | 537.7 | 66.6 | 513.3 | 27.6 | 12.1 | 401.7 | 22.5 | - | 472.4 | 5.1 |
| PacificBlue | 98.3 | 13.5 | 108.7 | 107.7 | 98.4 | 24.7 | 198.2 | 30.6 | - | 37.2 |
| PerCP | 536.6 | 105.4 | 53.5 | 21.6 | 19.8 | 474.3 | 47.3 | 6 | 467.9 | - |

FIG. 17A
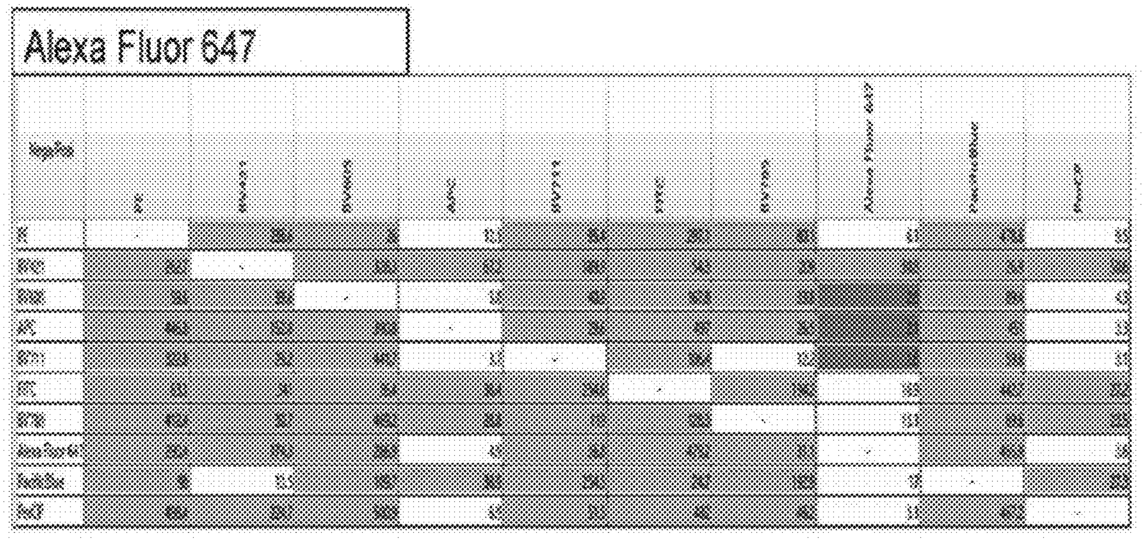
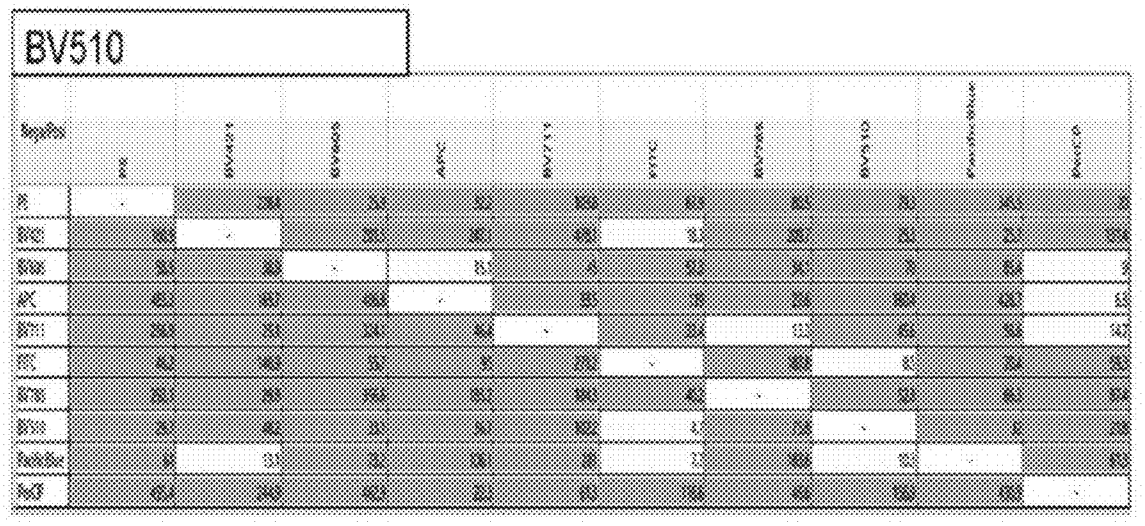
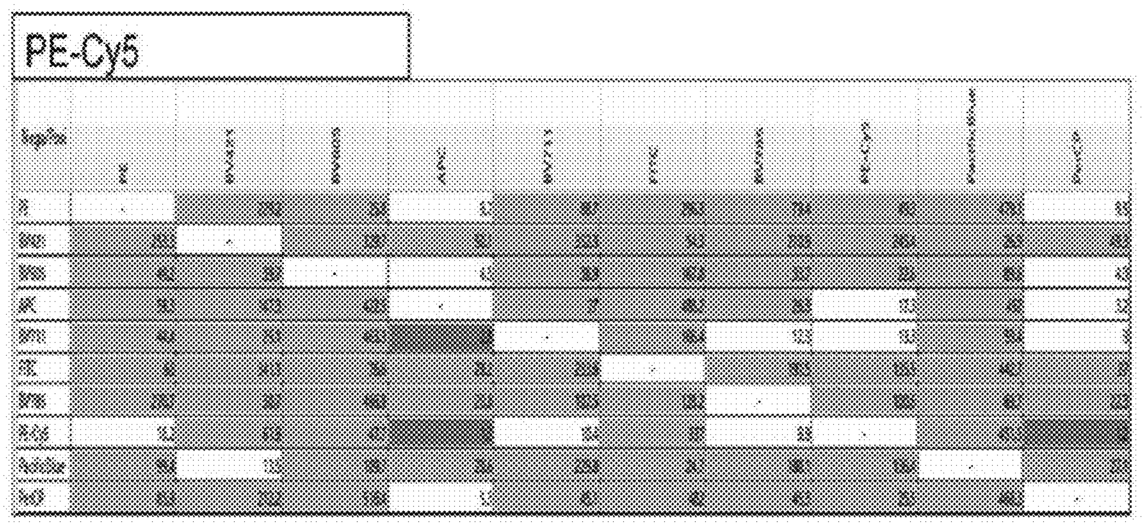

FIG. 17B
APC-Cy7
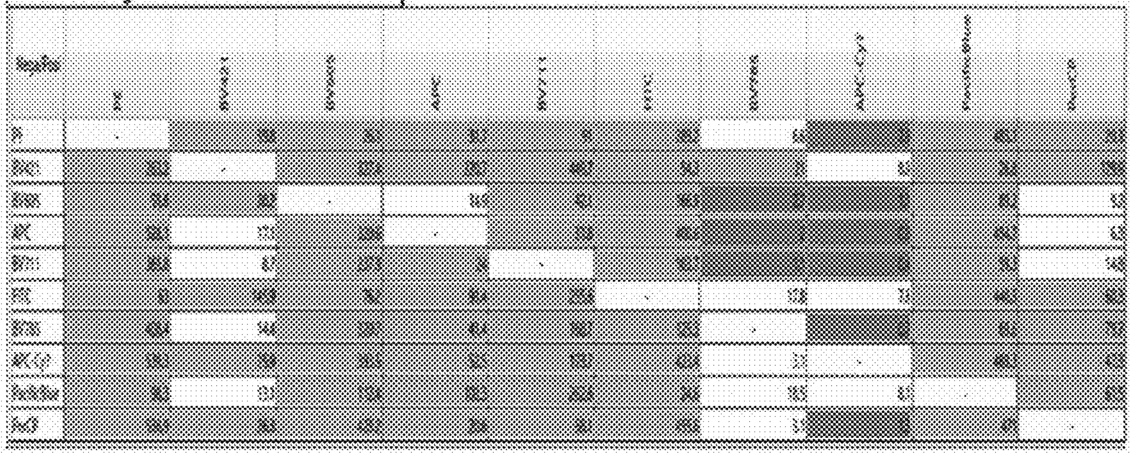
BV650
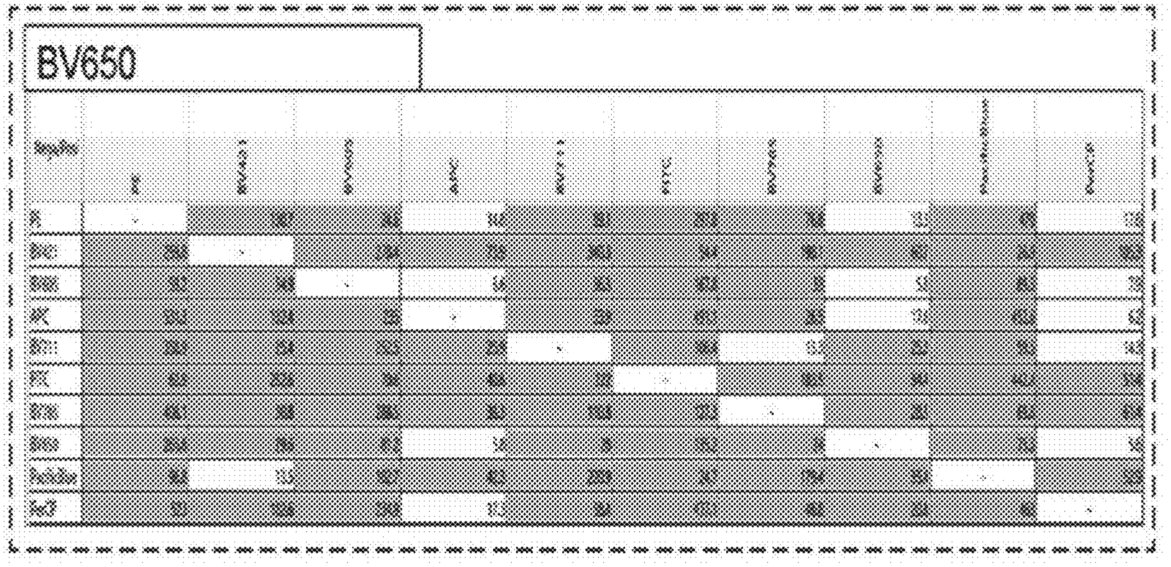
PE-Cy7
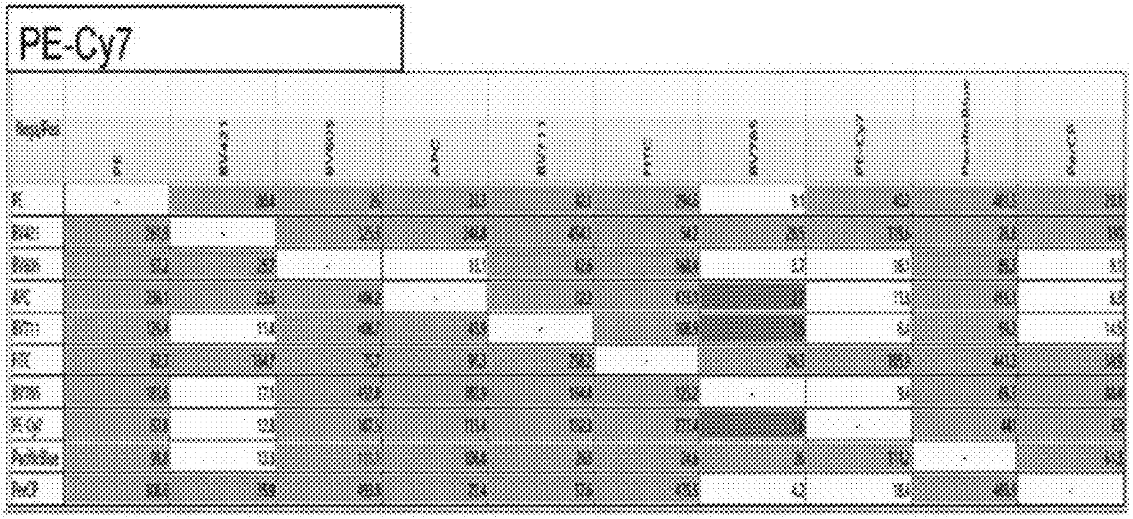

FIG. 20

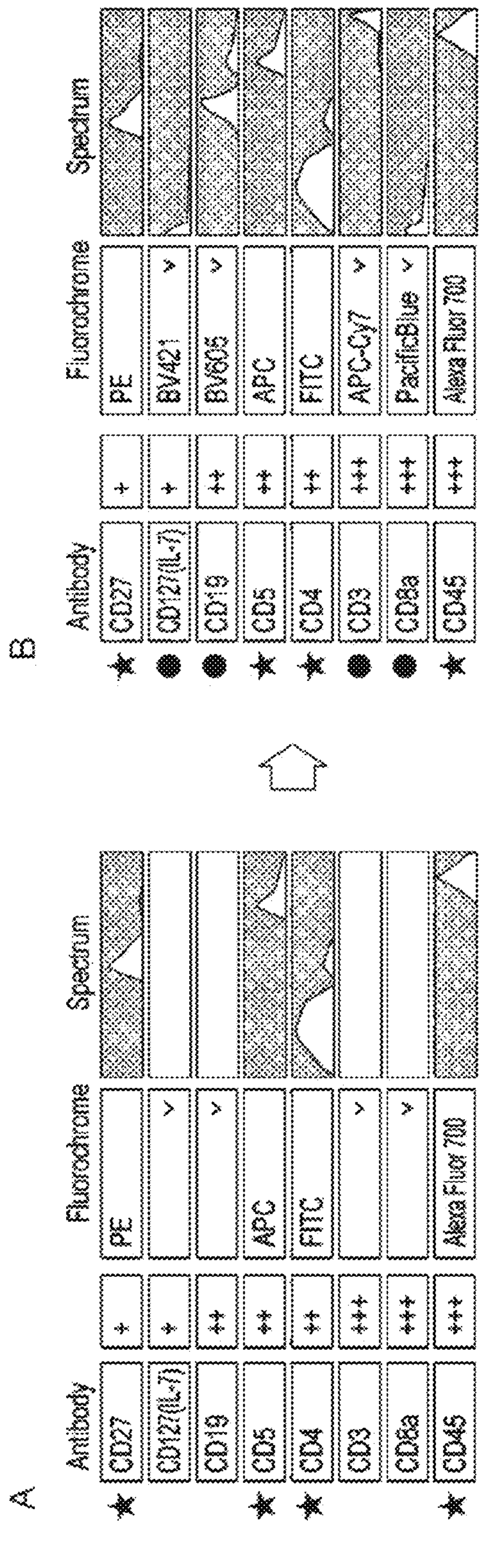

C

| Antibody | Fluorochrome | Clone | ISO Type | Target Species | Host Species | Catalog | Size | Company | Price | URL | Product Name |
|---|---|---|---|---|---|---|---|---|---|---|---|
| CD127 (IL-7Rα) | BV421 | A019D5 | IgG1, κ | human | Mouse | 2356545 | 25 tests | sony | 34400 | https://d177rtdsxfernhgl.cloudfront.net/pub/media/pdfs/2356545_TDS.pdf | Anti-human CD127 (IL-7Rα),Mouse |
| CD19 | BV605 | HIB19 | IgG1, κ | human | Mouse | 2111215 | 25 tests | sony | 32400 | https://d177rtdsxfernhgl.cloudfront.net/pub/media/pdfs/2111215_TDS.pdf | Isotype Control,Mouse,IgG1, κ,BV |
| CD3 | APC-Cy7 | SK7 | IgG1, κ | human | Mouse | 2324085 | 25 tests | sony | 22800 | https://d177rtdsxfernhgl.cloudfront.net/pub/media/pdfs/2324085_TDS.pdf | Anti-human CD3,Mouse,IgG1, κ,Al |
| CD8a | PacificBlue | HIT8a | IgG1, κ | human | Mouse | 2104640 | 100 tests | sony | 43400 | https://d177rtdsxfernhgl.cloudfront.net/pub/media/pdfs/2104640_TDS.pdf | Anti-human CD8a,Mouse,IgG1, κ,F |

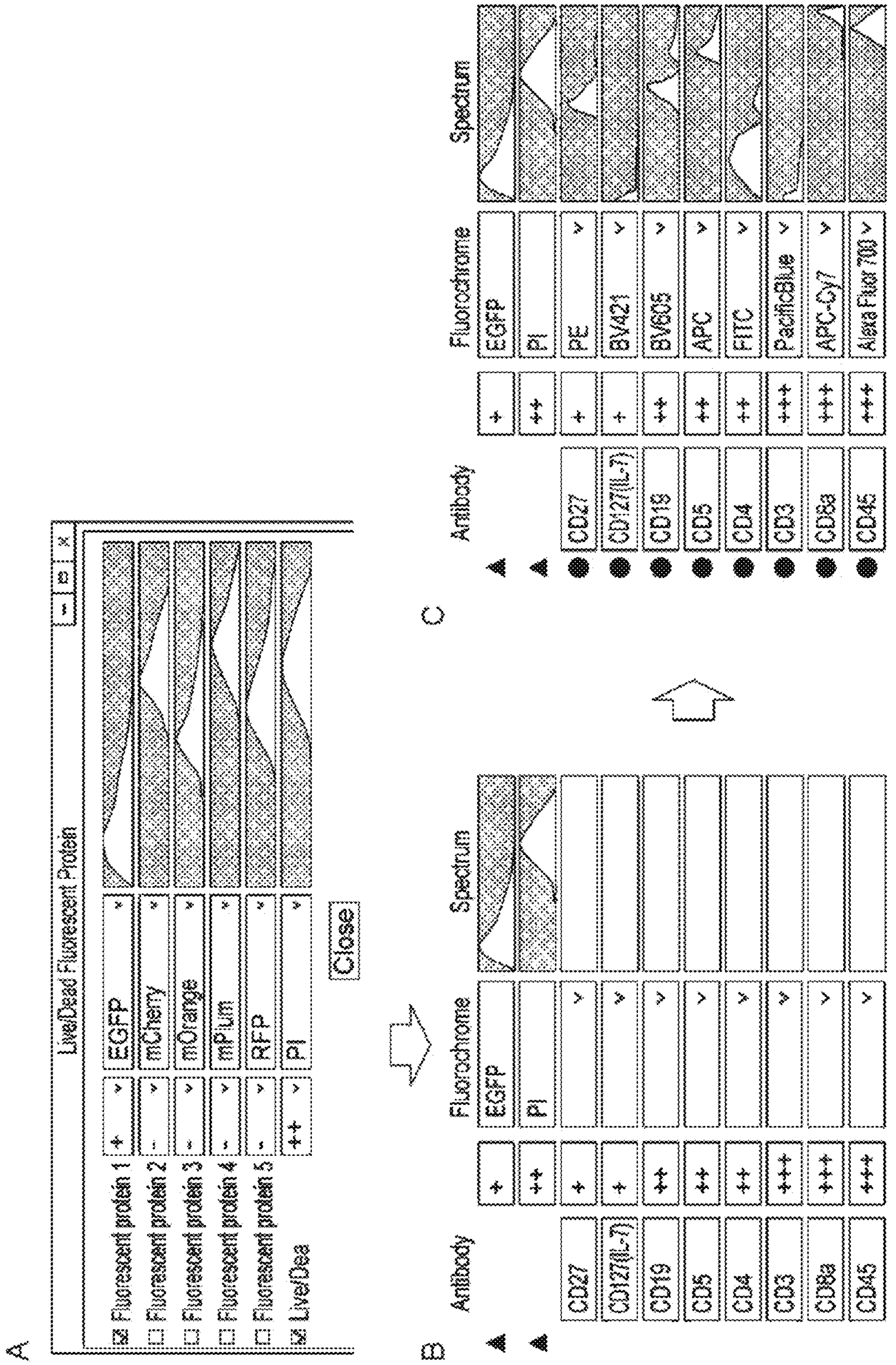

Live/Dead Fluorescent Protein

Fluorescent protein 1 + EGFP
Fluorescent protein 2 - mCherry
Fluorescent protein 3 - mOrange
Fluorescent protein 4 - mPlum
Fluorescent protein 5 - RFP
Live/Dea ++ PI Close

B

| Antibody | | Fluorochrome | Spectrum |
|---|---|---|---|
| | + | EGFP | |
| | ++ | PI | |
| CD27 | + | | |
| CD127(IL-7) | + | | |
| CD19 | ++ | | |
| CD5 | ++ | | |
| CD4 | ++ | | |
| CD3 | +++ | | |
| CD8a | +++ | | |
| CD45 | +++ | | |

C

| Antibody | | Fluorochrome | Spectrum |
|---|---|---|---|
| | + | EGFP | |
| | ++ | PI | |
| CD27 | + | PE | |
| CD127(IL-7) | + | BV421 | |
| CD19 | ++ | BV605 | |
| CD5 | ++ | APC | |
| CD4 | ++ | FITC | |
| CD3 | +++ | PacificBlue | |
| CD8a | +++ | APC-Cy7 | |
| CD45 | +++ | Alexa Fluor 700 | |

FIG. 23A

ALL FLUOROCHROMES USABLE IN FCM DEVICE

| Nega / Posi | Alexa Fluo | Alexa Fluo | Alexa Fluo | Alexa Fluo | Alexa Fluo | AMCA_P | Am Cyan_ | ... | PerCP-eF | PerCP_P | Qdot605_ | Qdot655_ | Qdot705_ | Qdot800_ | VioBlue_P |
|---|---|---|---|---|---|---|---|---|---|---|---|---|---|---|---|
| Alexa Fluor 532 | 100000 | 17 | 72.6 | 385.3 | 1008 | 303.4 | 33.5 | ... | 83 | 130.9 | 31.3 | 46.9 | 77.3 | 277.3 | 138.4 |
| Alexa Fluor 555 | 321.6 | 100000 | 114.8 | 487.6 | 2139.8 | 817.8 | 86.6 | ... | 115.6 | 192.8 | 136.5 | 108 | 220.3 | 674.8 | 410.5 |
| Alexa Fluor 594 | 1165.1 | 157.8 | 100000 | 47 | 180.9 | 430 | 56.8 | ... | 38.6 | 25.4 | 30.8 | 16 | 30.5 | 182.7 | 208.7 |
| Alexa Fluor 647 | 1459.8 | 293.7 | 307.1 | 100000 | 70.9 | 670.8 | 68.9 | ... | 80.4 | 61.4 | 279.1 | 57.7 | 72.3 | 371.6 | 280.8 |
| Alexa Fluor 700 | 556.8 | 175.4 | 252 | 75.1 | 100000 | 314.3 | 40.8 | ... | 37 | 39.7 | 176.4 | 95.7 | 51.7 | 104.3 | 149.5 |
| AMCA | 810.6 | 205.4 | 283.1 | 700.7 | 1865.4 | 100000 | 32.3 | ... | 286.7 | 196.6 | 100.3 | 145.9 | 164.1 | 495.6 | 30.4 |
| ⋮ | ⋮ | ⋮ | ⋮ | ⋮ | ⋮ | ⋮ | ⋮ | | ⋮ | ⋮ | ⋮ | ⋮ | ⋮ | ⋮ | ⋮ |
| PerCP-eF710 | 2055.9 | 198.6 | 466 | 59.7 | 73.8 | 497.8 | 65.7 | ... | 100000 | 18.1 | 322 | 64.9 | 29.8 | 56.1 | 272.1 |
| PerCP | 1073.2 | 244.6 | 307.3 | 47.4 | 160.8 | 322.3 | 47.1 | ... | 30.4 | 100000 | 173.5 | 34.2 | 28.6 | 120.7 | 156.4 |
| Qdot 605 | 1384.8 | 129.4 | 69.4 | 580.5 | 1796.2 | 757.9 | 78.7 | ... | 301.2 | 178.2 | 100000 | 48.9 | 135.3 | 903.1 | 347 |
| Qdot 655 | 1960.3 | 292.7 | 94 | 60.2 | 361.6 | 780.5 | 92.9 | ... | 65.3 | 31.3 | 63 | 100000 | 39.9 | 499.1 | 376.9 |
| Qdot 705 | 1407.9 | 184.3 | 266 | 44.5 | 87 | 360.8 | 53.7 | ... | 16.8 | 14.9 | 161.6 | 27.1 | 100000 | 62.7 | 196.2 |
| Qdot 800 | 725.2 | 214.5 | 238.6 | 252.2 | 175.9 | 168.2 | 39.1 | ... | 42.3 | 51.7 | 110.5 | 83.4 | 48.2 | 100000 | 89.5 |
| VioBlue | 1484.3 | 284.2 | 382.7 | 908.6 | 2499.2 | 112.2 | 45.8 | ... | 384.2 | 238.6 | 151.2 | 190.2 | 298.3 | 516 | 100000 |

ALL FLUOROCHROMES USABLE IN FCM DEVICE

| | Sample Name | Subset Name | Count |
|---|---|---|---|
| | PE_Spillover_LSM_A_Unmixed_WLSM_A.fcs | Ungated | 1547 |
| | FITC_Spillover_LSM_A_Unmixed_WLSM_A.fcs | Ungated | 1544 |

$$① \quad {}^{PE}SI_{FITC} = \{ {}^{PE}F_{PE} - {}^{PE}F_{FITC} \} \div \{ {}^{PE}\sigma_{FITC} \times 2 \}$$

| SSM | FITC | PE |
|---|---|---|
| FITC | 0 | ① |
| PE | ② | 0 |

*FIG. 24A*

ALL FLUOROCHROMES USABLE IN FCM DEVICE

ALL FLUOROCHROMES USABLE IN FCM DEVICE

| Sample / Filter | Alexa Fluor 532 | Alexa Fluo | Alexa Fluo | Alexa Fluo | Alexa Fluo | AMCA_F | AmCyan_ | ... | PerCP-eF | PerCP_F | Qdot605_ | Qdot655_ | Qdot705_ | Qdot800_ | VioBlue_F |
|---|---|---|---|---|---|---|---|---|---|---|---|---|---|---|---|
| Alexa Fluor 532 | 0.0 | 3.6 | 1.5 | 0.3 | 0.1 | 0.0 | 4.2 | ... | 0.9 | 1.1 | 3.1 | 3.0 | 1.4 | 0.4 | 0.4 |
| Alexa Fluor 555 | 0.3 | 0.0 | 1.7 | 0.5 | 0.3 | 0.1 | 3.0 | ... | 1.2 | 1.2 | 1.2 | 2.4 | 1.5 | 0.7 | 0.7 |
| Alexa Fluor 594 | 0.1 | 0.9 | 0.0 | 1.5 | 0.4 | 0.1 | 1.6 | ... | 2.7 | 4.4 | 4.6 | 5.9 | 3.2 | 0.7 | 0.2 |
| Alexa Fluor 647 | 0.0 | 0.2 | 0.3 | 0.0 | 0.9 | 0.0 | 1.2 | ... | 1.2 | 1.7 | 0.2 | 1.8 | 1.4 | 0.3 | 0.2 |
| Alexa Fluor 700 | 0.1 | 0.5 | 0.2 | 1.1 | 0.0 | 0.0 | 2.2 | ... | 2.8 | 3.5 | 0.3 | 1.6 | 2.8 | 1.2 | 0.1 |
| AMCA | 0.1 | 0.4 | 0.5 | 0.1 | 0.0 | 0.0 | 4.2 | ... | 0.4 | 0.9 | 1.4 | 1.0 | 0.6 | 0.4 | 2.3 |
| ⋮ | ⋮ | ⋮ | ⋮ | ⋮ | ⋮ | ⋮ | ⋮ | | ⋮ | ⋮ | ⋮ | ⋮ | ⋮ | ⋮ | ⋮ |
| PerCP-eF710 | 0.1 | 0.6 | 0.3 | 1.2 | 1.1 | 0.2 | 1.7 | ... | 0.0 | 5.8 | 0.3 | 1.9 | 4.8 | 2.0 | 0.2 |
| PerCP | 0.1 | 0.4 | 0.5 | 1.7 | 0.5 | 0.0 | 0.0 | ... | 3.3 | 0.0 | 0.6 | 3.1 | 3.4 | 1.0 | 0.0 |
| Qdot 605 | 0.1 | 0.7 | 1.7 | 0.2 | 0.1 | 0.0 | 1.0 | ... | 0.4 | 0.7 | 0.0 | 2.5 | 0.9 | 0.2 | 0.0 |
| Qdot 655 | 0.0 | 0.3 | 1.2 | 1.4 | 0.3 | 0.1 | 0.4 | ... | 1.4 | 3.6 | 2.1 | 0.0 | 3.1 | 0.2 | 0.1 |
| Qdot 705 | 0.1 | 0.6 | 0.5 | 1.6 | 1.0 | 0.1 | 2.3 | ... | 5.5 | 7.0 | 0.6 | 3.4 | 0.0 | 1.8 | 0.3 |
| Qdot 800 | 0.2 | 0.8 | 0.5 | 0.6 | 0.5 | 0.3 | 3.8 | ... | 2.8 | 3.4 | 0.6 | 1.8 | 2.8 | 0.0 | 0.6 |
| VioBlue | 0.0 | 0.2 | 0.2 | 0.1 | 0.0 | 0.7 | 2.5 | ... | 0.3 | 0.6 | 0.6 | 0.6 | 0.4 | 0.3 | 0.0 |

① $^{FITC}SS_{PE} = \{ (^{PE}\sigma_{FITC})^2 - (^{PE}\sigma_{Nega})^2 \}^{0.5} \div \{ ^{FITC}F_{FITC} - {}^{FITC}F_{Nega} \}^{0.5}$
SSM
FITC
PE
FITC
0
②
PE
①
0
PE-A
FITC-A
Unstain
FITC
$^{FITC}F_{FITC}$
$^{FITC}F_{Nega}$
$^{PE}\sigma_{Nega}$
$^{PE}\sigma_{FITC}$
Sample Name
Subset Name
Count
Ungated
Ungated

FIG. 25A

| Nega/Pos | BV421 | Qdot 605 | BUV737 | Alexa Fluor 594 | BUV395 | BV711 | PE-Cy7 | APC-Cy7 | BV785 | Qdot 655 | BV480 | PE-Cy5.5 | Alexa Fluor 532 | Alexa Fluor 700 | BUV496 | APC | FITC | PerCP | BV570 | PE |
|---|---|---|---|---|---|---|---|---|---|---|---|---|---|---|---|---|---|---|---|---|
| BV421 | - | 284.9 | 4205.7 | 2305.5 | 156.4 | 532.6 | 863.8 | 1868.6 | 321.6 | 68.1 | 24.8 | 437.5 | 670.3 | 2025.3 | 157.4 | 559.8 | 332.4 | 356.5 | 101.9 | 86.3 |
| Qdot 605 | 70.7 | - | 3865.1 | 1038.9 | 239 | 462.4 | 865.8 | 1739 | 339.4 | 41.3 | 35.3 | 434.3 | 605.9 | 1945.9 | 194.5 | 475.8 | 301.6 | 267.1 | 46.4 | 43.9 |
| BUV737 | 57 | 284.9 | - | 1590.7 | 41.3 | 106.7 | 179.9 | 282.7 | 71.6 | 50.2 | 28.9 | 201.6 | 624.9 | 108.3 | 124.9 | 192 | 290.6 | 223.1 | 92 | 62.2 |
| Alexa Fluor 594 | 67 | 52.8 | 863.3 | - | 178.4 | 96.6 | 240.9 | 765.3 | 124.4 | 10 | 28 | 113.8 | 606.7 | 202 | 153.6 | 32.8 | 295.8 | 63.7 | 59.6 | 30.4 |
| BUV395 | 75.3 | 251.9 | 4023.6 | 2281.8 | - | 520.4 | 852.2 | 1725.6 | 337.7 | 66.3 | 33.1 | 435 | 692.7 | 2041.5 | 132.1 | 580.7 | 312.8 | 352.1 | 109 | 90.5 |
| BV711 | 22.9 | 263.1 | 497.4 | 2288.2 | 135 | - | 394.5 | 552.6 | 66.9 | 52.2 | 25.9 | 227.2 | 636.9 | 162.5 | 167.6 | 228.3 | 321.3 | 176.9 | 98.4 | 75.4 |
| PE-Cy7 | 76.1 | 238.7 | 1875.8 | 1081.1 | 214.3 | 409.5 | - | 304 | 76.8 | 61.1 | 36.4 | 335.7 | 422.8 | 128 | 195.6 | 427.1 | 221.9 | 322.8 | 97.5 | 38.5 |
| APC-Cy7 | 57.5 | 236.9 | 906.2 | 1509.5 | 171.8 | 237 | 121.5 | - | 45 | 32.1 | 28 | 357.2 | 591.9 | 183.3 | 155.3 | 44 | 255.1 | 202.4 | 94.2 | 76.7 |
| BV785 | 33.3 | 262.3 | 1457 | 2288.6 | 163.7 | 300.6 | 445.5 | 715.3 | - | 61.8 | 26 | 419.8 | 636.1 | 1216.4 | 168.5 | 459 | 318.6 | 301.7 | 98.5 | 85.8 |
| Qdot 655 | 66.1 | 198.5 | 3647.5 | 1706.6 | 215.6 | 360.7 | 786.4 | 1746.2 | 320.3 | - | 38.5 | 363.2 | 596.2 | 1225.6 | 201.8 | 131.4 | 295.2 | 165.5 | 108.4 | 82.5 |
| BV480 | 76.9 | 230.9 | 4088.2 | 2284 | 207.7 | 484.1 | 874 | 1697.8 | 248.8 | 61.4 | - | 427.5 | 569.8 | 2021.3 | 146.7 | 547.1 | 213.7 | 308 | 87.1 | 78.5 |
| PE-Cy5.5 | 76.1 | 187.3 | 792.1 | 635 | 205.1 | 108.2 | 112.2 | 686.3 | 120.1 | 40.1 | 36.3 | - | 378.2 | 216.5 | 192.7 | 155.5 | 235.2 | 118.4 | 72.4 | 18.2 |
| Alexa Fluor 532 | 69.1 | 130 | 2472.7 | 620.6 | 169.5 | 438.7 | 581 | 1724.7 | 282.2 | 40.2 | 26.4 | 303.1 | - | 1780.3 | 113.6 | 438.9 | 74 | 245.8 | 61.5 | 13.5 |
| Alexa Fluor 700 | 68.1 | 232.8 | 548.1 | 1560 | 171.1 | 84.4 | 251.4 | 246.4 | 94.7 | 56.1 | 28.9 | 200.3 | 486.1 | - | 155.7 | 146.4 | 196.4 | 215.6 | 94.5 | 66.3 |
| BUV496 | 75.8 | 170.6 | 2762.5 | 2211.9 | 81 | 491.4 | 860.1 | 1691.2 | 235.9 | 50.7 | 21.7 | 431.1 | 397.3 | 1965.9 | - | 538.8 | 113.8 | 259.4 | 80.4 | 69.5 |
| APC | 86.3 | 286.6 | 151.1 | 1847.5 | 216 | 236.2 | 502.8 | 762.5 | 234.1 | 26.4 | 35.8 | 362.4 | 601.7 | 159.4 | 199 | - | 298.7 | 177.1 | 113.9 | 82.7 |
| FITC | 85.7 | 213.8 | 4137.4 | 2275.4 | 197.3 | 513.3 | 763.5 | 1683.8 | 286.6 | 62.4 | 25.6 | 421.3 | 229.2 | 2007.2 | 118.2 | 541.2 | - | 328.1 | 87.4 | 65.8 |
| PerCP | 70.2 | 234.6 | 633 | 1902.6 | 176.7 | 104.5 | 340.1 | 970 | 139.4 | 28.8 | 28.2 | 157.1 | 629.1 | 298.8 | 157.5 | 96.3 | 297.5 | - | 94.8 | 64.7 |
| BV570 | 33.7 | 164.9 | 2983 | 718.1 | 167.1 | 253.8 | 718.5 | 1748.3 | 231 | 32.6 | 26.6 | 371.8 | 532 | 1665 | 163.8 | 403.2 | 306.5 | 226.5 | - | 38.2 |
| PE | 82.8 | 185.2 | 3972.5 | 776.1 | 217.7 | 484.8 | 758.4 | 1738.9 | 338 | 52.8 | 38.2 | 363.9 | 432.7 | 1982.1 | 195.8 | 486.2 | 263.9 | 283.5 | 74.1 | - |

FIG. 25C

| Nega/Posi | BV421 | PE-Cy5 | PerCP-eF710 | Alexa Fluor 594 | AmCyan | BV711 | Alexa Fluor 647 | PerCP-Cy5.5 | PE-Cy7 | Qdot 655 | BV480 | PE-Cy5.5 | APC-Cy7 | AMCA | BUV496 | APC | FITC | Qdot 705 | VioBlue | BV510 |
|---|---|---|---|---|---|---|---|---|---|---|---|---|---|---|---|---|---|---|---|---|
| BV421 | - | 748.6 | 997.6 | 2113.8 | 20.4 | 210.7 | 334.7 | 577.3 | 832.6 | 64.6 | 4 | 298.3 | 1844.9 | 153.6 | 101.8 | 182.7 | 132.7 | 671.4 | 14.4 | 10 |
| PE-Cy5 | 43.4 | - | 140.4 | 750.8 | 20.5 | 32.1 | 24.5 | 111.3 | 149.1 | 13.5 | 7.2 | 53.5 | 730.4 | 343.8 | 129.5 | 13.8 | 168.3 | 125.8 | 46 | 9.8 |
| PerCP-eF710 | 25.8 | 198.4 | - | 1835.4 | 28.3 | 15.4 | 32.7 | 61.4 | 84.8 | 23.3 | 6.9 | 154.5 | 286.2 | 311.3 | 119.5 | 27.6 | 165.4 | 47.6 | 42.1 | 11.1 |
| Alexa Fluor 594 | 48 | 99.6 | 253.9 | - | 25.6 | 50.2 | 26.5 | 105.1 | 248.6 | 8.9 | 6.6 | 64.8 | 837.9 | 275.8 | 94.3 | 13.7 | 144.1 | 124 | 40.7 | 7 |
| AmCyan | 58 | 747.3 | 967.7 | 2501.7 | - | 199.7 | 308.8 | 496.6 | 841.4 | 57.7 | 3.9 | 201.8 | 1830.9 | 318.1 | 70.9 | 171.4 | 59.7 | 660.1 | 38.8 | 7.8 |
| BV711 | 22.3 | 590.3 | 310.8 | 2074 | 21.9 | - | 88.1 | 201.4 | 400 | 37.5 | 4.6 | 228.2 | 606.2 | 239.1 | 117.7 | 65.6 | 141.1 | 107.1 | 17.9 | 10.1 |
| Alexa Fluor 647 | 56.7 | 389.2 | 802 | 1785.3 | 29.5 | 170.1 | - | 378.6 | 498.4 | 29 | 7.3 | 227.8 | 757.4 | 353.7 | 137.9 | 17.6 | 181.5 | 368.4 | 46.2 | 11.9 |
| PerCP-Cy5.5 | 34 | 138.4 | 92.9 | 1874.9 | 27.8 | 20.7 | 24.5 | - | 122 | 19.4 | 6.7 | 178.7 | 372.7 | 265.7 | 118.7 | 20.2 | 163.4 | 57.3 | 41.5 | 10.9 |
| PE-Cy7 | 55.6 | 506.8 | 559.9 | 860 | 24.2 | 124.9 | 289.9 | 479.4 | - | 58.5 | 7.2 | 186.3 | 521.6 | 347 | 130.7 | 156 | 162.9 | 461.3 | 46.4 | 10.2 |
| Qdot 655 | 56.5 | 318.8 | 724.6 | 1790.2 | 30.2 | 172.8 | 115.3 | 298.7 | 824.9 | - | 7.3 | 252.4 | 1804.1 | 353.5 | 132.2 | 53.2 | 178.6 | 470.7 | 47.8 | 11 |
| BV480 | 56.7 | 750.5 | 976.8 | 2460.8 | 18.4 | 202.2 | 312.5 | 508.4 | 876.2 | 56.5 | - | 281.8 | 1798.6 | 283.4 | 80.2 | 178 | 113.9 | 636.5 | 37.8 | 8.8 |
| PE-Cy5.5 | 41.3 | 156.8 | 124 | 594.3 | 28.5 | 29.4 | 58.5 | 142.7 | 117.8 | 32.1 | 7.2 | - | 753 | 331.9 | 115.7 | 45.2 | 158.8 | 109.1 | 45.4 | 7.8 |
| APC-Cy7 | 54.2 | 375.2 | 746.2 | 1535.5 | 26.5 | 123.9 | 41.4 | 308.1 | 119 | 25.7 | 6.6 | 221.9 | - | 286.9 | 108 | 21.1 | 154.4 | 242.5 | 41 | 10.3 |
| AMCA | 21.2 | 722.4 | 921.7 | 2248.4 | 23.4 | 188.1 | 286.9 | 461.4 | 837 | 48.9 | 4.3 | 277.7 | 1803.8 | - | 48.8 | 165 | 148.6 | 490.7 | 14.8 | 7.5 |
| BUV496 | 54.1 | 728.4 | 953.8 | 2429.1 | 21.6 | 185.3 | 300.6 | 488.5 | 840.4 | 49.6 | 5.7 | 287 | 1786.3 | 116.6 | - | 173.9 | 98.7 | 446 | 39.9 | 8.6 |
| APC | 56 | 323.8 | 737.7 | 1708.4 | 29.5 | 131.2 | 31.8 | 298.7 | 514.6 | 20.7 | 7.3 | 229.1 | 880.9 | 349.8 | 137.2 | - | 182.4 | 240.7 | 46.3 | 11.8 |
| FITC | 57.5 | 703.4 | 869.1 | 2193 | 26.3 | 195 | 309.3 | 533.9 | 752.9 | 58.9 | 6.9 | 284.9 | 1838.8 | 332.5 | 89.9 | 173.1 | - | 638.3 | 46.3 | 10.6 |
| Qdot 705 | 34.9 | 152.3 | 110.8 | 1880.1 | 26.7 | 21.7 | 31.5 | 62 | 144.5 | 12.5 | 6.7 | 173.6 | 477 | 286.3 | 114.2 | 23 | 159.8 | - | 41 | 10.2 |
| VioBlue | 27.4 | 751.5 | 984.1 | 2394.3 | 16.9 | 204.5 | 314.1 | 538.2 | 870.1 | 60.8 | 3.4 | 295.9 | 1836.5 | 197 | 82.7 | 177.1 | 112.1 | 656.3 | - | 8.3 |
| BV510 | 57.8 | 704.3 | 964 | 2547.8 | 26.5 | 189.3 | 301.9 | 462.8 | 874 | 50.6 | 6.4 | 291.2 | 1774.3 | 286.5 | 82.4 | 177 | 152.3 | 553.6 | 42.3 | - |

| time | limitation on | limitation off |
| --- | --- | --- |
| 15 antibodies | 35 sec | 273 sec |
| 20 antibodies | 26 sec | 525 sec |

| Nega/Posi | PE | BV421 | BV605 | PE-Cy7 | APC | FITC | PerCP-Cy5.5 | PacificBlue | BV711 | BV510 |
|---|---|---|---|---|---|---|---|---|---|---|
| PE | - | 131.6 | 26.4 | 344.4 | 36.3 | 341.1 | 85.4 | 246.7 | 276.2 | 338.8 |
| BV421 | 161.1 | - | 200.9 | 870.9 | 205.1 | 91.8 | 504.9 | 23.6 | 1362.2 | 136.7 |
| BV605 | 87.8 | 28.8 | - | 146.7 | 18.7 | 268.4 | 39.8 | 85.5 | 123.6 | 281.8 |
| PE-Cy7 | 88.9 | 282.6 | 107.4 | - | 132.1 | 229.8 | 204.4 | 337 | 441.2 | 415.2 |
| APC | 474.2 | 96.1 | 410.3 | 113.5 | - | 401 | 20.1 | 424.6 | 90.4 | 807.5 |
| FITC | 21.1 | 89.1 | 25.9 | 876.9 | 50.8 | - | 123 | 31.2 | 418 | 19 |
| PerCP-Cy5.5 | 492 | 49.3 | 493 | 44.2 | 14.6 | 526.4 | - | 356.2 | 45.2 | 707.4 |
| PacificBlue | 61.2 | 13.7 | 73.2 | 814.6 | 124.7 | 38.8 | 246.8 | - | 238.8 | 51.4 |
| BV711 | 126.8 | 10.9 | 190.7 | 25.7 | 22.8 | 80.8 | 20.3 | 28.3 | - | 111.9 |
| BV510 | 13.3 | 23.3 | 14.8 | 263.4 | 19.8 | 10.4 | 41.8 | 14.4 | 131 | - |

INFORMATION PROCESSING APPARATUS, INFORMATION PROCESSING SYSTEM, INFORMATION PROCESSING METHOD, AND PROGRAM

CROSS-REFERENCE TO RELATED APPLICATIONS

This application claims the benefit under 35 U.S.C. § 371 as a U.S. National Stage Entry of International Application No. PCT/JP2021/023111, filed in the Japanese Patent Office as a Receiving Office on Jun. 17, 2021, which claims priority to Japanese Patent Application Number JP2020-124469, filed in the Japanese Patent Office on Jul. 21, 2020, each of which is hereby incorporated by reference in its entirety.

TECHNICAL FIELD

The present technology relates to an information processing apparatus, an information processing system, an information processing method, and a program. More specifically, the present technology relates to an information processing apparatus, an information processing system, an information processing method, and a program that propose how to allocate a phosphor to a biomolecule.

BACKGROUND ART

For example, particle populations such as cells, microorganisms, and liposomes are labeled with a fluorochrome, and the intensity and/or pattern of fluorescence generated from the fluorochrome excited by irradiating each particle of the particle population with laser light is measured, thereby measuring the characteristics of the particles. Typical examples of the particle analyzer that performs the measurement include a flow cytometer.

The flow cytometer is a device that irradiates particles flowing in a line in a flow path with laser light (excitation light) having a specific wavelength and detects fluorescence and/or scattered light emitted from each particle to analyze a plurality of particles one by one. The flow cytometer can convert light detected by the photodetector into an electrical signal, quantify the electrical signal, and perform statistical analysis to determine characteristics, such as the type, size, and structure, of each particle.

Several technologies have been proposed so far regarding a technique for selecting a fluorochrome to be used for labeling a particle population to be analyzed by a flow cytometer. For example, Patent Document 1 below describes a method for designing a probe panel of a flow cytometer, the method including: determining a strain factor that quantifies an effect of leakage into a second channel caused by emission of a first label intended to be measured in a first channel;

- inputting a predicted maximum signal of a first probe-label combination that includes the first label and a first probe;
- calculating an increase in a detection limit in the second channel on the basis of the strain factor and the predicted maximum signal of the first probe-label combination; and
- selecting a probe-label combination included in the probe panel on the basis of the calculated increase in the detection limit.

CITATION LIST

Patent Document

Patent Document 1: Japanese Unexamined Patent Application Publication (Translation of PCT Application) No. 2016-517000

SUMMARY OF THE INVENTION

Problems to be Solved by the Invention

In order to label the particle population to be analyzed by the flow cytometer, a plurality of fluorochrome-labeled antibodies is often used. The determination process for the combination of fluorochrome-labeled antibodies that are used in the analysis is also called panel design. The number of fluorochrome-labeled antibodies used in the analysis tends to increase, and as the number increases, panel design becomes more difficult.

Therefore, a main object of the present technology is to provide a technique of automatically proposing a better combination of fluorochrome-labeled antibodies.

Solutions to Problems

The present technology provides an information processing apparatus including a processing unit that generates a combination list of phosphors with respect to biomolecules on the basis of expression level categories in which a plurality of biomolecules to be used for analysis of a sample is classified on the basis of expression levels in the sample, brightness categories in which a plurality of phosphors usable for the analysis of the sample is classified on the basis of brightness, and correlation information between the plurality of phosphors, in which the processing unit selects the phosphors to be allocated to the biomolecules in the combination list from phosphors belonging to a brightness category associated with an expression level category to which the biomolecules belong.

The expression level categories are associated with the brightness categories such that an expression level category obtained by classifying a biomolecule exhibiting a lower expression level corresponds to a brightness category in which a brighter phosphor is classified.

The processing unit can select each of the phosphors by using the correlation information.

The correlation information can be a correlation coefficient between fluorescence spectra of the plurality of phosphors.

The correlation information can be a value obtained by squaring a correlation coefficient between fluorescence spectra of the plurality of phosphors.

The processing unit can calculate the correlation coefficient by using two or more fluorescence spectra respectively obtained in a case where a phosphor is irradiated with excitation light beams having two or more different wavelengths.

The correlation information can be a stain index between the plurality of phosphors.

The correlation information can be a spillover spreading matrix between the plurality of phosphors.

The plurality of phosphors can be identified on the basis of data regarding whether a complex of a phosphor and a biomolecule is available.

The processing unit can adjust the number of phosphors belonging to each of the brightness categories in accordance with the number of biomolecules belonging to each of the expression level categories.

The plurality of phosphors can be identified on the basis of information regarding priority associated with the phosphors.

The processing unit can perform evaluation of separation capability related to the combination list.

The processing unit can further generate a modified combination list in which at least one phosphor of a set of phosphors included in the combination list is changed to another phosphor in accordance with a result of the evaluation of the separation capability and further performs separation capability evaluation related to the modified combination list.

The processing unit can further generate the combination list on the basis of cost information regarding a complex of a biomolecule and a phosphor.

In a case where a phosphor to be allocated to at least one biomolecule among the plurality of biomolecules is identified, the processing unit can further generate the combination list on the basis of correlation information between the plurality of phosphors and the phosphor identified in advance.

In a case where a light-producing substance to be used for analysis of the sample is identified, the processing unit can further generate the combination list on the basis of correlation information between the plurality of phosphors and the light-producing substance.

Each of the plurality of biomolecules can be an antigen or an antibody.

In a case where each of the plurality of biomolecules is an antigen, the expression level may be an expression level of the antigen, and in a case where each of the plurality of biomolecules is an antibody, the expression level can be an expression level of an antigen captured by the antibody.

Further, the present technology also provides an information processing system including: an input unit that accepts an input of data regarding expression levels of a plurality of biomolecules to be used for analysis of a sample; and a processing unit that generates a combination list of phosphors with respect to biomolecules on the basis of expression level categories in which the plurality of biomolecules is classified on the basis of expression levels in the sample, brightness categories in which a plurality of phosphors usable for the analysis of the sample is classified on the basis of brightness, and correlation information between the plurality of phosphors, in which the processing unit selects the phosphors to be allocated to the biomolecules in the combination list from phosphors belonging to a brightness category associated with an expression level category to which the biomolecules belong.

Further, the present technology also provides an information processing method including a list generation step of generating a combination list of phosphors with respect to biomolecules on the basis of expression level categories in which a plurality of biomolecules to be used for analysis of a sample is classified on the basis of expression levels in the sample, brightness categories in which a plurality of phosphors usable for the analysis of the sample is classified on the basis of brightness, and correlation information between the plurality of phosphors, in which in the list generation step, the phosphors to be allocated to the biomolecules in the combination list are selected from phosphors belonging to a brightness category associated with an expression level category to which the biomolecules belong.

Further, the present technology also provides a program causing an information processing apparatus to execute a list generation step of generating a combination list of phosphors with respect to biomolecules on the basis of expression level categories in which a plurality of biomolecules to be used for analysis of a sample is classified on the basis of expression levels in the sample, brightness categories in which a plurality of phosphors usable for the analysis of the sample is classified on the basis of brightness, and correlation information between the plurality of phosphors, in which in the list generation step, the phosphors to be allocated to the biomolecules in the combination list are selected from phosphors belonging to a brightness category associated with an expression level category to which the biomolecules belong.

BRIEF DESCRIPTION OF DRAWINGS

FIG. 5A is a diagram for explaining information processing according to the present technology.

FIG. 5B is a diagram for explaining information processing according to the present technology.

FIG. 6 is a diagram showing a matrix of correlation coefficient square values.

FIG. 10 is a diagram showing an example of a list related to a phosphor.

FIG. 14 is a flowchart of separation capability evaluation processing.

FIG. 17A is a diagram showing a calculation result of inter-phosphors SI.

FIG. 17B is a diagram showing a calculation result of inter-phosphors SI.

FIG. 20 is a diagram showing an example of an input acceptance window.

FIG. 22 is a diagram showing an example of an input acceptance window.

FIG. 23A is a diagram showing an example of a normalized inter-phosphor SI list.

FIG. 24A is a diagram showing an example of inter-phosphor SSM.

FIG. 25A is a view showing inter-phosphor stain indexes obtained by an experiment.

FIG. 25C is a view showing inter-phosphor stain indexes obtained by an experiment.

FIG. 28 is a diagram showing the processing time required to generate a combination list.

MODE FOR CARRYING OUT THE INVENTION

Modes for carrying out the present technology will be described below. Note that embodiments described below show representative embodiments of the present technology, and the scope of the present technology is not limited only to these embodiments. Note that the present technology will be described in the following order.

1. First Embodiment (Information Processing Apparatus)
   (1) Details of Problems of the Invention
   (2) Example of Flow of Experiment Performed Using Present Technology
   (3) Description of First Embodiment
   (3-1) Configuration Example of Information Processing Apparatus
   (3-2) Example of Processing by Processing Unit (Processing Flow)
   (Example 1: Evaluation Using Simulation Data)
   (Example 2: Evaluation Using Cells)
   (3-3) Example of Processing by Processing Unit (Example of Fluorescence Spectrum Used in Calculation of Correlation Coefficient)
   (3-4) Example of Processing by Processing Unit (Example of Referring to Database Regarding Availability of Reagent)
   (3-5) Example of Processing by Processing Unit (Example of Adjusting Number of Phosphors Classified into Each Brightness Category)
   (3-6) Example of Processing by Processing Unit (Example in which Information Regarding Priority is Associated with Each Phosphor, and Phosphors to be Used in Optimization are Limited in Accordance with Number of Selected Phosphors)
   (Example 3: Comparison of Whether Information Regarding Priority is Used) (3-7) Example of Processing by Processing Unit (Example of Executing Separation Capability Evaluation)
   (Example 4: Comparison of Performance or Non-Performance of Separation Capability Evaluation)
   (3-8) Example of Processing by Processing Unit (Processing Flow in Consideration of Reagent Cost)
   (3-9) Example of Processing by Processing Unit (Processing Flow in Case where Phosphor Determined in Advance to be Adopted is Included)
   (3-10) Example of Processing by Processing Unit (Processing Flow in Case where Light-Producing Substance, Determined in Advance to be Adopted, is Included)
   (3-11) Example of Processing by Processing Unit (Processing Flow in Case where Stain Index Between Phosphors or Spillover Spreading Matrix Between Phosphors is Used as Correlation Information)
   (3-11-1) Case of Using Stain Index Between Phosphors
   (Example 5: Evaluation Using Simulation Data—Case of Normalized Inter-Phosphor SI)
   (3-11-2) Case of Using Spillover Spreading Matrix Between Phosphors
   (Example 6: Evaluation Using Simulation Data—Case of Inter-Phosphor SSM)
2. Second Embodiment (Information Processing System)
3. Third Embodiment (Information Processing Method)
4. Fourth Embodiment (Program)

1. First Embodiment (Information Processing Apparatus)

(1) Details of Problems of the Invention

Figure 1:
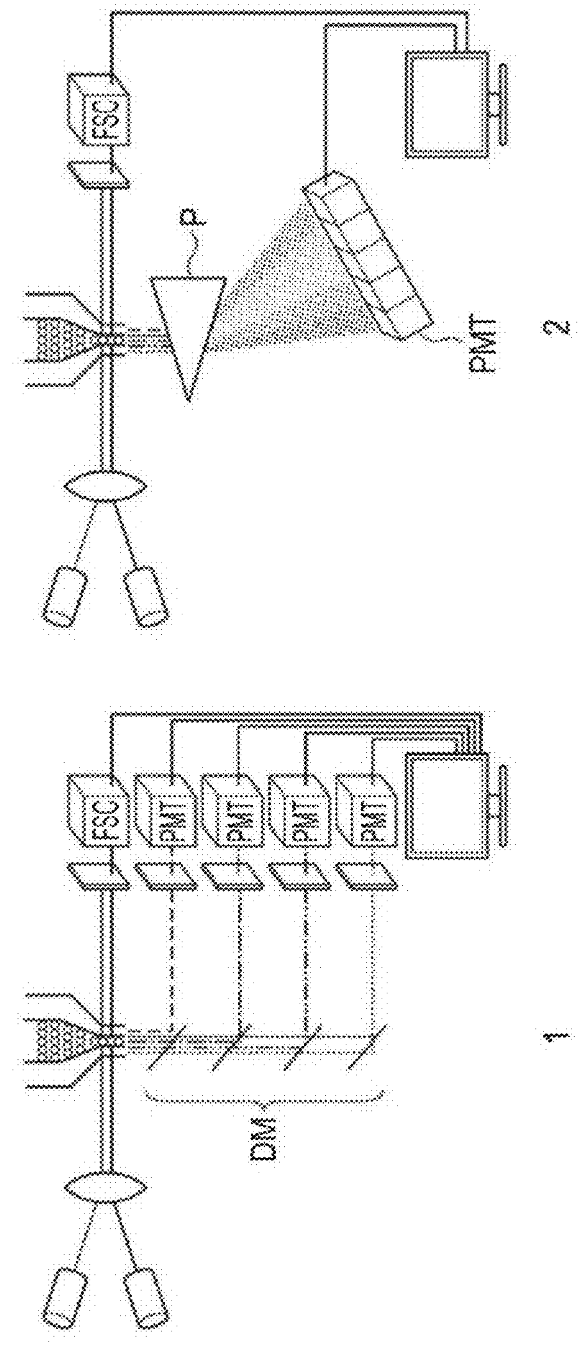
FIG. 1 is a schematic diagram of a configuration of a flow cytometer.

The flow cytometer can be roughly classified into a filter type and a spectral type, for example, from the viewpoint of an optical system of fluorescence measurement. The filter flow cytometer can adopt a configuration as shown in 1 of FIG. 1 in order to extract only target light information from a target fluorochrome. Specifically, light generated by irradiating the particles with light is branched into a plurality of pieces by a wavelength separation means DM such as a dichroic mirror and allowed to pass through different filters, and then each branched light is measured by a plurality of detectors, for example, a photomultiplier tube PMT and the like. That is, in the filter flow cytometer, fluorescence detection is performed for each wavelength band corresponding to each fluorochrome by using a detector corresponding to each fluorochrome, to perform fluorescence detection of multiple colors. At that time, in a case where a plurality of fluorochromes each having a close fluorescence wavelength is used, fluorescence correction processing can be performed in order to calculate a more accurate amount of fluorescence. However, in a case where a plurality of fluorochromes each having a very close fluorescence spectrum is used, leakage of fluorescence to detectors except for the detector to detect the fluorescence increases, and hence an event in which fluorescence correction cannot be performed can also occur.

The spectral flow cytometer performs deconvolution (unmixing) on fluorescence data, obtained by detecting light generated by irradiating the particles with light, with the spectrum information of the fluorochrome used for staining to analyze the amount of fluorescence of each particle. As shown in 2 of FIG. 1, the spectral flow cytometer disperses fluorescence by using a prism spectroscopic optical element P. Further, in order to detect the spectral flow cytometer and the dispersed fluorescence, an array-type detector, such as an array-type photomultiplier PMT, is provided instead of a large number of photodetectors provided in the filter flow cytometer. The spectral flow cytometer more easily avoids the influence of leakage of fluorescence and is more suitable for analysis using a plurality of fluorochromes than the filter flow cytometer.

In order to advance comprehensive interpretation in basic medicine and clinical fields, multicolor analysis using a plurality of fluorochromes has become widespread also in flow cytometry. However, when a large number of fluorochromes are used in one measurement as in the multicolor analysis, in the filter flow cytometer, as described above, fluorescence from a fluorochrome except for a target fluorochrome leaks into each detector, and analysis accuracy decreases. In a case where the number of colors is large, the problem of leakage of fluorescence can be solved to some extent by using the spectral flow cytometer. However, in order to perform more appropriate multicolor analysis, an appropriate panel design (combination design of fluorochrome and antibody) in which the fluorescence spectrum shape, the antibody expression level, and the brightness of the fluorochrome are taken into consideration is required.

Panel design has traditionally relied heavily on user experience and trial-and-error adjustments. However, as the number of colors increases, particularly when the number of colors is about 20 or more, the number of combinations of fluorochromes to be considered rapidly increases, and hence it is extremely difficult to find an optimal dye combination having sufficient decomposition performance.

Device manufacturers that sell flow cytometers, reagent manufacturers that sell antibodies with fluorochromes, and the like have released web tools for panel design for promoting their products. However, as the number of colors increases, these web tools may not exhibit sufficient practicality.

When the number of colors is, for example, ten or more, it is not possible to avoid the occurrence of a large overlap between fluorescence spectra, and it is difficult for a person to predict fluorescence leakage that actually occurs from the appearance overlap of spectra. If the number of parameters is one, the parameter can be adjusted manually by a person to some extent, but there is a plurality of parameters to be adjusted independently in the panel design of the multicolor analysis. Main examples of the parameter to be considered include, for example, the fluorescence spectrum shape, the expression level of the antigen, and the brightness of the fluorochrome described above. Moreover, it is also desirable to consider the excitation characteristics, availability, and cost of the fluorochrome. Therefore, it is very difficult to determine which fluorochrome should be preferentially adopted and to predict the influence on the whole by changing a combination of some fluorochromes. The basic principle regarding fluorescence correction and independent information regarding each fluorochrome and antigen are not sufficient for an appropriate panel design, and it is extremely difficult to manually find an optimal combination. Since the number of panel candidates generated in the case of considering the plurality of parameters described above is enormous, it is considered that if a better panel can be automatically presented, it can contribute to a significant reduction in the burden on the user.

(2) Example of Flow of Experiment Performed Using Present Technology

Figure 2:
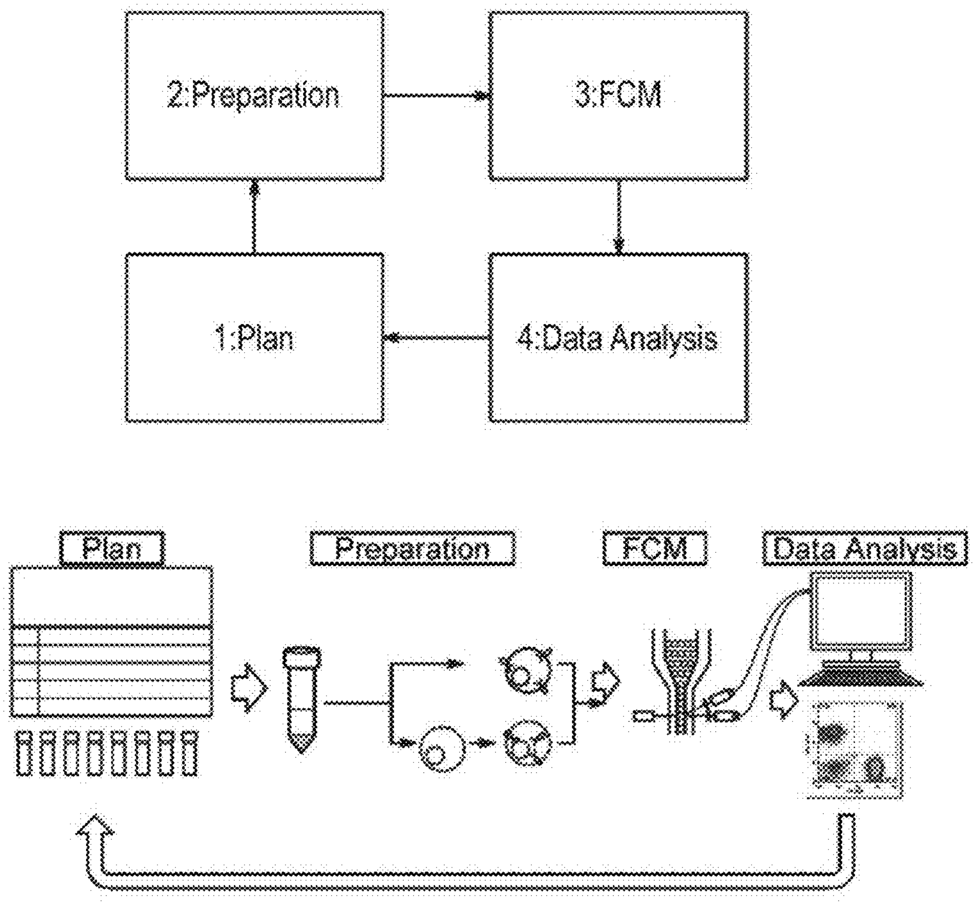
FIG. 2 is a diagram showing an experimental flow example in a case where the present technology is applied in flow cytometry.

As described above, the present technology may be used to generate a list related to combinations of antibodies and phosphors that are in particle analysis such as flow cytometry. An experimental flow example in the case of applying the present technology in flow cytometry will be described with reference to FIG. 2.

The flow of the experiment using the flow cytometer is roughly classified into: an experiment planning step ("1: Plan" in FIG. 2) of examining a cell to be an experiment target and a method for detecting the cell to prepare an antibody reagent with a fluorescence index; a sample preparation step ("2: Preparation" in FIG. 2) of actually staining and preparing the cell in a state suitable for measurement; a flow cytometry (FCM) measurement step ("3: FCM" in FIG. 2) of measuring the amount of fluorescence of each stained cell by the flow cytometer; and a data analysis step ("4: Data Analysis" in FIG. 2) of performing various data processing so as to obtain a desired analysis result from data recorded by the FCM measurement. Then, these steps can be repeated as necessary.

In the experiment planning step, first, which molecule (e.g., antigen, cytokine, etc.) expression is used to determine a microparticle (mainly a cell) that is desired to be detected using a flow cytometer, that is, a marker to be used in the detection of the microparticle, is determined. The determination can be made on the basis of, for example, information such as past experimental results and papers. Next, which fluorochrome is used to detect the marker is examined. Information such as the number of markers desired to be detected at the same time, specifications of a usable FCM device, commercially available fluorescence-labeled reagents, and the spectrum, brightness, price, and delivery date of the fluorochrome is comprehensively determined, and a combination of fluorescence-labeled antibody reagents necessary for actual experiments is determined. The determination process for the combination of reagents is commonly referred to as panel design in FCM. Here, a reagent that is insufficient among a set of reagents determined by the panel design is ordered to a reagent manufacturer and purchased. However, fluorescence-labeled antibody reagents are expensive, and a relatively rare reagent and the like may take one month or more from order placement to delivery. Therefore, it is not realistic to perform trial and error by repeating the above four steps many times. It is desirable to obtain desired results with fewer number of times of experiment planning steps.

In the sample preparation step, first, the experiment target is processed into a state suitable for FCM measurement. For example, cell separation and purification can be performed. For example, for immune cells derived from blood or the like, red blood cells are removed from the blood by hemolysis and density gradient centrifugation, and white blood cells are extracted. The staining processing is performed on the extracted cell group as a target by using a fluorescence-labeled antibody. At this time, in addition to the sample to be analyzed that is simultaneously stained with a plurality of fluorochromes, it is generally recommended to prepare a single stained sample stained with only one fluorochrome to be used as a criterion at the time of analysis and a non-stained sample not stained at all.

In the FCM measurement step, at the time of optically analyzing the microparticle, first, excitation light is emitted from a light source of a light irradiation unit of the flow cytometer, and the microparticle flowing in the flow path is irradiated with the excitation light. Next, fluorescence emitted from the microparticle is detected by a detection unit of the flow cytometer. Specifically, using a dichroic mirror, a bandpass filter, or the like, only light of a specific wavelength (target fluorescence) is separated from light emitted from the microparticle, and the separated light is detected by a detector such as a 32-channel PMT. At this time, for example, fluorescence is dispersed using a prism, a diffraction grating, or the like, and light having a different wavelength is detected in each channel of the detector. This can facilitate obtaining spectrum information of detection light (fluorescence). The microparticle to be analyzed is not particularly limited, and examples thereof include cells, microbeads, and the like.

The flow cytometer can have a function of recording fluorescence information of each fine particle acquired by FCM measurement together with scattered light information, time information, and position information other than the fluorescence information. The recording function can be mainly executed by a memory or a disk of a computer. In normal cell analysis, analysis of several thousand to several one million microparticles is performed under one experimental condition, and it is thus necessary to record a large number of pieces of information in an organized state for each experimental condition.

In the data analysis step, light intensity data in each wavelength region detected in the FCM measurement step is quantified using a computer or the like, and the amount of fluorescence (intensity) for each fluorochrome used is obtained. For this analysis, a correction method using a criterion calculated from experimental data is used. The criterion is calculated by statistical processing by using two types of measurement data of microparticles stained with only one fluorochrome and measurement data of unstained microparticles. The calculated amount of fluorescence can be recorded in a data recording unit provided in the computer together with information such as the name of the fluorescent molecule, the measurement date, and the type of the microparticle. The amount of fluorescence (fluorescence spectrum data) of the sample estimated by the data analysis is stored and displayed as a graph in accordance with the purpose, and the fluorescence amount distribution of the microparticle is analyzed. For example, the proportion of cells to be detected contained in the measured sample can be calculated by analyzing the fluorescence amount distribution.

The present technology can be used for panel design in the experiment planning step. For example, the information processing apparatus according to the present technology can accept the input of the biomolecule and the expression level of the biomolecule in the measurement target by the user, and can automatically generate the optimized FCM experimental panel by using the input data. That is, it can be said that the information processing apparatus of the present technology is an apparatus having an optimization algorithm for the panel generation.

Further, as another example of the particle analysis to which the present technology is applied, a microparticle sorter for sorting microparticles in a closed space can be mentioned. For example, in order to determine whether to sort the microparticles, the device may include: a chip that has a flow path through which the microparticle is allowed to flow and in which the microparticle is sorted; a light irradiation unit that irradiates the microparticles flowing through the flow path with light; a detection unit that detects light generated by the light irradiation; and a determination unit that determines whether to sort the microparticles on the basis of information regarding the detected light. Examples of the microparticle sorter include a device described in Japanese Patent Application Laid-Open No. 2020-041881.

In addition, the analysis to which the present technology is applied is not limited to particle analysis. That is, the present technology may be used in various types of processing in which allocation of a phosphor to a biomolecule is required. For example, in microscopic analysis or observation of a cell sample or a tissue sample, such as multicolor fluorescence imaging, processing of allocating a phosphor to a biomolecule according to the present technology may be performed in order to stain these samples. In recent years, the number of phosphors used tends to increase also in fluorescence imaging, and the present technology can also be used in such analysis or observation.

(3) Description of First Embodiment

The information processing apparatus according to the present technology includes a processing unit that generates a combination list of phosphors with respect to biomolecules. The processing unit generates the combination list on the basis of expression level categories obtained by classifying a plurality of biomolecules to be used for analysis of a sample on the basis of an expression level in the sample, brightness categories in which a plurality of phosphors usable for the analysis of the sample is classified on the basis of brightness, and correlation information between the plurality of phosphors. In the generation, the processing unit selects the phosphors to be allocated to the biomolecules in the combination list from phosphors belonging to a brightness category associated with an expression level category to which the biomolecules belong.

By performing the selection and generating the combination list, a more appropriate combination list can be generated, and the processing for the generation is performed more efficiently. This makes it possible to automatically perform the optimized panel design.

(3-1) Configuration Example of Information Processing Apparatus

Figure 3:
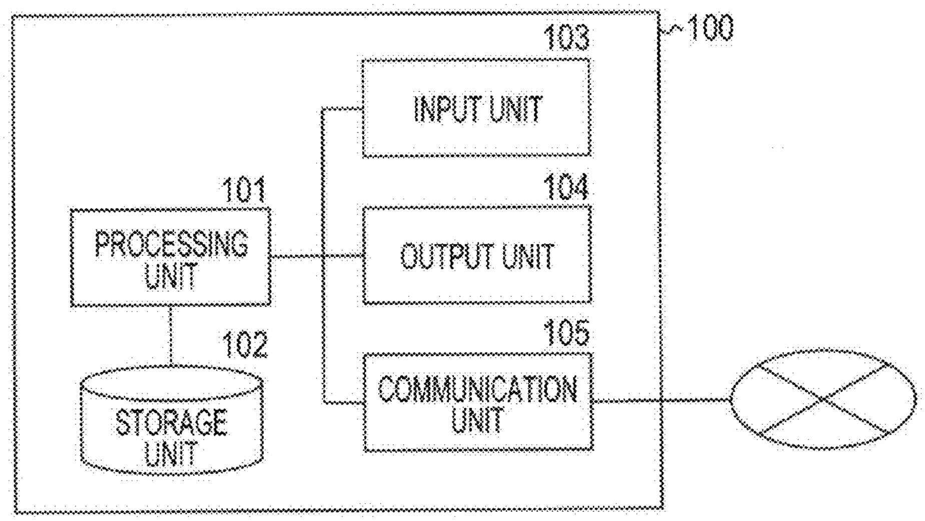
FIG. 3 is a diagram showing a configuration example of an information processing apparatus according to the present technology.

An example of the information processing apparatus according to the present technology will be described with reference to FIG. 3. FIG. 3 is a block diagram of the information processing apparatus. An information processing apparatus 100 shown in FIG. 3 can include a processing unit 101, a storage unit 102, an input unit 103, an output unit 104, and a communication unit 105. The information processing apparatus 100 may be configured by, for example, a general-purpose computer.

The processing unit 101 is configured to be able to generate a combination list of phosphors with respect to biomolecules. The processing of generating the combination list will be described in detail below. The processing unit 101 can include, for example, a central processing unit (CPU) and a random-access memory (RAM). The CPU and the RAM may be connected to each other via, for example, a bus. An input/output interface may be further connected to the bus. The input unit 103, the output unit 104, and the communication unit 105 may be connected to the bus via the input/output interface.

The storage unit 102 stores various data. The storage unit 102 may be configured to be able to store, for example, data acquired in processing to be described later, data generated in processing to be described later, and/or the like. Examples of these pieces of data include, but are not limited to, various data accepted by the input unit 103 (e.g., biomolecule data and expression level data), various data accepted by the communication unit 105 (e.g., a list related to a phosphor), various data generated by the processing unit 101 (e.g., an expression level category, a brightness category, correlation information, combination list, etc.), and the like. Further, the storage unit 102 can store an operating system (e.g., WINDOWS (registered trademark), UNIX (registered trademark), LINUX (registered trademark), etc.), a program for causing the information processing apparatus or the information processing system to execute the information processing method according to the present technology, and various other programs.

The input unit 103 can include an interface configured to be able to accept inputs of various data. For example, the input unit 103 may be configured to be able to accept various data inputs in processing to be described later. Examples of the data include biomolecule data, expression level data, and the like. As a device that accepts such an operation, the input unit 103 can include, for example, a mouse, a keyboard, a touch panel, and the like.

The output unit 104 can include an interface configured to be able to output various data. For example, the output unit 104 may be configured to be able to output various data generated in processing to be described later. Examples of the data include, but are not limited to, various data (e.g., an expression level category, a brightness category, correlation information, a combination list, etc.) generated by the processing unit 101, and the like. The output unit 104 can include, for example, a display device as a device that outputs the data.

The communication unit 105 can be configured to connect the information processing apparatus 100 to a network in a wired or wireless manner. By the communication unit 105, the information processing apparatus 100 can acquire various data (e.g., a list related to a phosphor, etc.) via the network. The acquired data can be stored in, for example, the storage unit 102. The configuration of the communication unit 105 may be appropriately selected by those skilled in the art.

The information processing apparatus 100 may include, for example, a drive (not shown) or the like. The drive can read data (e.g., the various data mentioned above) or a program (e.g., the program described above, etc.) recorded in the recording medium and output the read data or program to the RAM. The recording medium is, for example, a micro secure digital (SD) memory card, an SD memory card, or flash memory, but is not limited thereto.

(3-2) Example of Processing by Processing Unit (Processing Flow)

Figure 4:
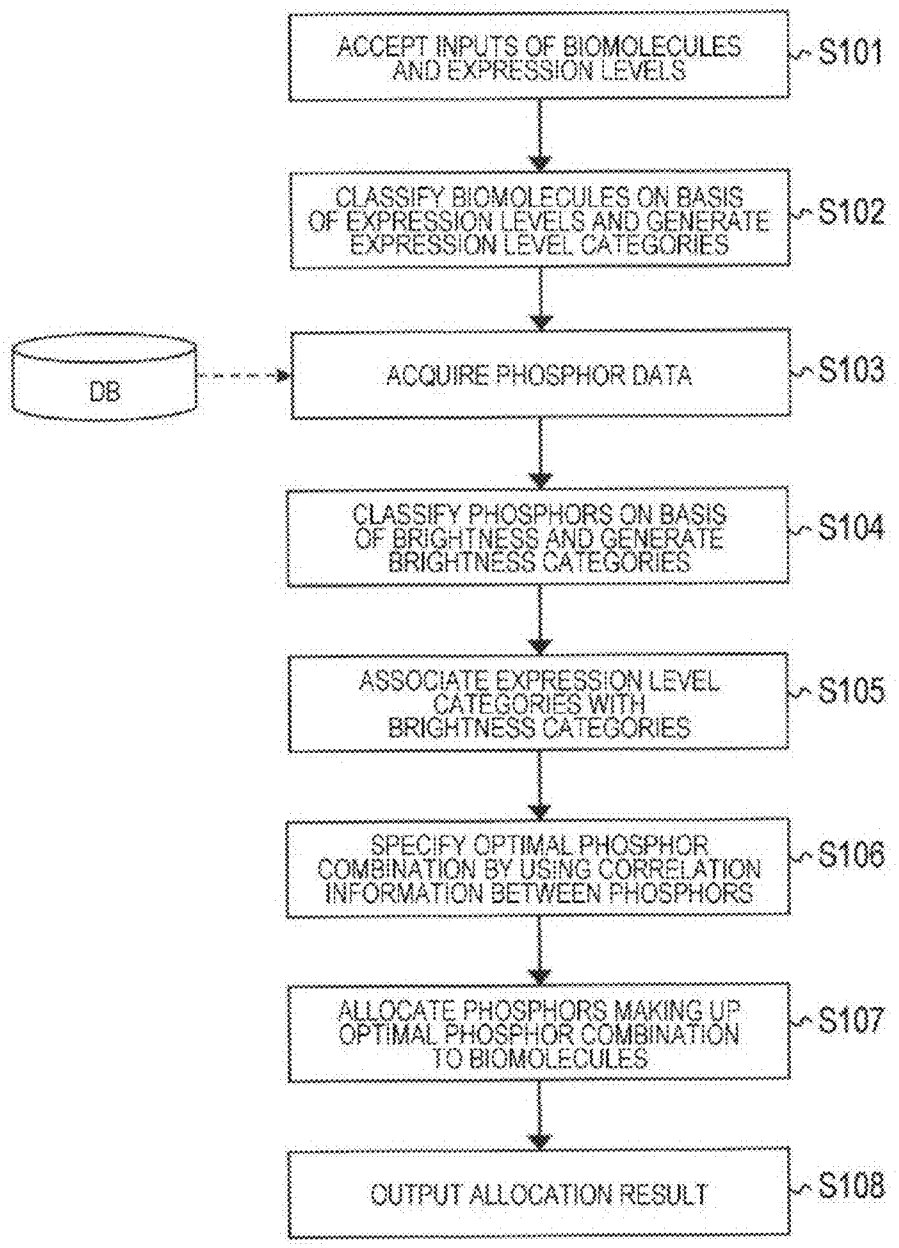
FIG. 4 is a flowchart of processing executed by the information processing apparatus according to the present technology.

Processing executed by the processing unit will be described below with reference to FIG. 4. FIG. 4 is a flowchart of the processing. The following description relates to an application example of the present technology in the case of optimizing a combination of an antibody and a fluorochrome used in flow cytometry.

In step S101 of FIG. 4, the information processing apparatus 100 (particularly, the input unit 103) accepts inputs of a plurality of biomolecules and the respective expression levels of the plurality of biomolecules.

The biomolecule may be an antigen to be measured in flow cytometry (e.g., a surface antigen, a cytokine, etc.) or may be an antibody that captures the antigen to be measured. In a case where the plurality of biomolecules is an antigen, the expression level may be an expression level of the antigen. In a case where each of the plurality of biomolecules is an antibody, the expression level may be an expression level of an antigen captured by the antibody.

The processing unit 101 can cause the output unit 104 (particularly, the display device) to display an input acceptance window for accepting the input to prompt the user to perform the input. The input acceptance window can include, for example, a biomolecule input acceptance field and an expression level acceptance field such as an "Antibody" field and an shown in a of FIG. 5A.

The biomolecule input acceptance field may be, for example, a plurality of list boxes LB1 prompting selection of a biomolecule, as shown in the "Antibody" field in FIG. 5A. In a of FIG. 5A, nine list boxes are described for convenience of description, but the number of list boxes is not limited thereto. The number of list boxes may be, for example, five to 300 or ten to 200.

In response to the user enabling each list box by an operation such as clicking or touching, the processing unit 101 displays a list of options of biomolecules above or below the list box. In response to the user selecting one biomolecule from the list, the list is closed and the selected biomolecule is displayed.

In a of FIG. 5A, a screen after the selection of the biomolecule by the user is displayed. In response to the selection of the antigen to be captured by the antibody, as shown in the drawing, for example, "CD1a", "CD2", or the like is displayed.

Further, the expression level acceptance field may be, for example, a plurality of list boxes LB2 that promotes selection of an expression level, as shown in the "Expression Level" field in a of FIG. 5A. The number of the list boxes LB2 prompting the selection of the expression level may be the same as the number of the list boxes LB1 prompting the selection of the biomolecule. In a of FIG. 5A, nine list boxes are described for convenience of description, but the number of list boxes is not limited thereto. The number of list boxes may be, for example, five to 300 or ten to 200.

In response to the user enabling each list box by an operation such as clicking or touching, the processing unit 101 displays a list of options of expression levels above or below the list box. In response to the user selecting one biomolecule from the list, the list is closed and the selected expression level is displayed.

In a of FIG. 5A, a screen after the selection of the expression level by the user is displayed. In response to the grade of the expression level being selected, as shown in the drawing, for example, "+", "++", and "+++" are displayed In a of FIG. 5A, for example, "+" is selected as the expression level of the biomolecule "CD1a". Further, "++" is selected as the expression level of the biomolecule "CD4". The symbols "+", "++", and "+++" mean that the expression level increases in this order.

In the present specification, the "expression level", for example, may mean the grade of the expression level or may be a specific numerical value of the expression level. Preferably, as shown in a of FIG. 5A above, the expression level means the grade of the expression level. The grades of the expression level may be preferably two to 20 grades, more preferably two to 15 grades, and still more preferably two to ten grades, and may be divided into, for example, three to ten grades.

After the selection of the biomolecule and the expression level is completed as described above, for example, in response to the user clicking a selection completion button (not shown) in the input acceptance window, the processing unit 101 accepts the input of the selected biomolecule and the expression level.

In step S102, the processing unit 101 classifies the plurality of biomolecules selected in step S101 on the basis of the expression levels selected for the respective biomolecules and generates one or a plurality of expression level categories, particularly a plurality of expression level categories. The number of expression level categories can be, for example, a value corresponding to the number of expression level grades and can be preferably two or more, and more preferably three or more. The number can be preferably two to 20, preferably three to 15, and even more preferably three to ten.

In a of FIG. 5A, the expression level grade "+", "++", or "+++" is selected for each of the plurality of biomolecules. The processing unit 101 classifies a biomolecule with the selected expression level grade as "+" into an expression level category "+". Similarly, the processing unit 101 classifies a biomolecule with the selected expression level grade as "++" or "+++" into an expression level category "++" or an expression level category "+++", respectively. In this way, the processing unit 101 generates three expression level categories. Each expression level category includes a biomolecule with a corresponding expression level grade selected. In a of FIG. 5A, three biomolecules at the expression level grade "+", four biomolecules at the expression level grade "++", and two biomolecules at the expression level grade "+++" are input.

In step S103, the processing unit 101 acquires a list related to phosphors capable of labeling the biomolecule input in step S101. The list of the phosphors may be acquired, for example, from a database existing outside the information processing apparatus 100 via the communication unit 105 or may be acquired from a database stored inside the information processing apparatus 100 (e.g., storage unit 102).

The list related to the phosphors can include, for example, a name and brightness for each phosphor. Further, the list related to the phosphors preferably also includes a fluorescence spectrum of each phosphor. The fluorescence spectrum of each phosphor may be acquired from the database as data different from the list.

Preferably, the list may selectively include phosphors usable in a device (e.g., microparticle analyzer) in which a specimen is analyzed using a combination of biomolecule and phosphor. The phosphors unusable in the device are deleted from the list, and it is thereby possible to reduce the burden on the device in processing to be described later (particularly, calculation processing for correlation information).

In step S104, the processing unit 101 classifies the phosphors included in the list related to the phosphors acquired in step S103 on the basis of the brightness of each phosphor and generates one or a plurality of brightness categories, particularly a plurality of brightness categories.

In step S104, preferably, the processing unit 101 generates a brightness category with reference to the expression level category generated in step S102. As a result, it is possible to more efficiently associate the brightness category to be generated with the expression level category and generate the combination of the biomolecule and the phosphor. The specific content of the reference will be described below.

The classification based on the brightness may be classification based on the amount of fluorescence or fluorescence intensity. In order to perform the classification, for example, a numerical range of the amount of fluorescence or the fluorescence intensity may be associated with each brightness category. Then, the processing unit 101 can classify each of the phosphors included in the list into a brightness category associated with a numerical range including the amount of fluorescence or the fluorescence intensity of each phosphor with reference to the amount of fluorescence or the fluorescence intensity.

Preferably, in step S104, the processing unit 101 generates brightness categories with reference to the number of expression level categories generated in step S102. Particularly preferably, in step S104, the processing unit 101 generates the same number of brightness categories as the number of expression level categories generated in step S102. Thus, the expression level category and the brightness category can be associated on a one-to-one basis. In addition, it is possible to prevent the generation of a phosphor that is not considered in the generation of a combination list to be described later, and it is possible to generate a better combination. The number of brightness categories may be, for example, a value corresponding to the number of expression level categories, and can be preferably two or more, and more preferably three or more. The number can be preferably two to 20, preferably three to 15, and even more preferably three to ten.

For example, as shown in b of FIG. 5A, three brightness categories (Bright, Normal, and Dim) may be generated. In these three brightness categories, the brightness decreases in this order, that is, any phosphor included in Bright is brighter than any phosphor included in Normal, and any phosphor included in Normal is brighter than any phosphor included in Dim.

Preferably, in step S104, the processing unit 101 generates the brightness category with reference to the number of biomolecules included in each of the expression level categories generated in step S102. Particularly preferably, in step S104, the processing unit 101 classifies the phosphors into each brightness category such that the phosphors equal to or more than the number of biomolecules included in the expression level category generated in step S102 are included in the associated brightness category. This makes it possible to prevent the generation of a biomolecule to which a phosphor is not allocated in the generation of a combination list described later.

In step S105, the processing unit 101 associates the expression level categories generated in step S102 with the brightness categories generated in step S104. Preferably, the processing unit 101 associates one expression level category with one brightness category. In addition, the processing unit 101 can perform association such that the expression level category and the brightness category correspond on a one-to-one basis. That is, the association can be performed such that two or more expression level categories are not associated with one brightness category.

In a particularly preferred embodiment of the present technology, the processing unit 101 can execute the association such that an expression level category having a lower expression level is associated with a higher brightness category. For example, the processing unit 101 can associate the expression level category having the smallest expression level with the brightness category having the highest brightness, then associate the expression level category having the second smallest expression level with the brightness category having the second highest brightness, and similarly repeat this association until there is no more expression level category. Conversely, the processing unit 101 can associate the expression level category having the largest expression level with the brightness category having the lowest brightness, then associate the expression level category having the second largest expression level with the brightness category having the second lowest brightness, and similarly repeat this association until there is no more expression level category.

In the present embodiment, for example, as indicated by arrows between a and b in FIG. 5A, the processing unit 101 associates the expression level categories "+", "++", and "+++" with the brightness categories "Bright", "Normal", and "Dim", respectively.

As described above, regarding the expression level category generated in the present technology, preferably, the expression level category in which biomolecules exhibiting a lower expression level are classified may be associated with the brightness category so as to correspond to the brightness category in which brighter phosphors are classified.

In step S106, the processing unit 101 identifies the optimal phosphor combination by using correlation information between phosphors. The optimal phosphor combination may be, for example, a phosphor combination that is optimal from the viewpoint of the correlation between fluorescence spectra, more particularly, a phosphor combination that is optimal from the viewpoint of a correlation coefficient between fluorescence spectra, and even more particularly, a phosphor combination that is optimal from the viewpoint of the square of the correlation coefficient between fluorescence spectra. The correlation coefficient may be, for example, any of a Pearson correlation coefficient, a Spearman correlation coefficient, or a Kendall correlation coefficient, and is preferably a Pearson correlation coefficient.

The correlation information between the phosphors may be preferably correlation information between fluorescence spectra. That is, in one preferred embodiment of the present technology, the processing unit 101 identifies the optimal phosphor combination by using correlation information between fluorescence spectra.

For example, the Pearson correlation coefficient can be calculated between two fluorescence spectra X, Y as follows.

First, the fluorescence spectra X, Y can be expressed as follows, for example.

Fluorescence spectrum $X=(X_1, X_2, \ldots, X_{320})$, mean value$=\mu_x$, standard deviation$=\sigma_x$ (where $X_1$ to $X_{320}$ are fluorescence intensities at 320 different wavelengths, the mean value $\mu_x$ is the mean value of these fluorescence intensities, and the standard deviation $\sigma_x$ is a standard deviation of these fluorescence intensities.)

Fluorescence spectrum $Y=(Y_1, Y_2, \ldots, Y_{320})$, mean value=μy, standard deviation$=\sigma_y$ (where $Y_1$ to $Y_{320}$ are fluorescence intensities at 320 different wavelengths. The mean value $\mu_y$ is the mean value of these fluorescence intensities. The standard deviation $\sigma_x$ is a standard deviation of these fluorescence intensities.)

Note that the numerical value "320" is a value set for convenience of description, and the numerical value used in the calculation of the correlation coefficient is not limited thereto. The numerical value may be appropriately changed in accordance with the configuration of the fluorescence detector, for example, the number of photomultiplier tubes (PMTs) used for fluorescence detection, and the like.

The Pearson correlation coefficient R between the fluorescence spectra X, Y is obtained by the following Expression 1.

$$R = \frac{\sum Z_{Xn} Z_{Yn}}{N} \quad \text{[Mathematical Expression 1]}$$

In the equation of Mathematical Expression 1, $Z_{Xn}$ (n is 1 to 320) is a standardized fluorescence intensity and is expressed as follows.

$$Zx1 = (X_1 - \mu_x) \div \sigma_x,\ Zx2 = (X_2 - \mu_x) \div \sigma_x,\ \ldots\ Zx320 = (X_{320} - \mu_x) \div \sigma_x$$

Similarly, $Z_{Yn}$ (n is 1 to 320) is also expressed as follows.

$$Zy1 = (Y_1 - \mu_y) \div \sigma_y,\ Zy2 = (Y_2 - \mu_y) \div \sigma_y,\ \ldots\ Zy320 = (Y_{320} - \mu_y) \div \sigma_y$$

In addition, in the equation of Expression 1, N is the number of pieces of data.

An example of how to identify the optimal phosphor combination will be described below.

The processing unit 101 selects, from a certain brightness category, the same number of phosphors as "the number of biomolecules belonging to the expression level category associated with the certain brightness category". The phosphors are selected for all brightness categories. Thereby, the same number of phosphors as the "number of a plurality of biomolecules to be used for analysis of a sample" are selected, and in this manner, one phosphor combination candidate is obtained.

Next, the processing unit 101 calculates the square of a correlation coefficient (e.g., Pearson correlation coefficient) between fluorescence spectra for any two combinations of phosphors included in the phosphor combination candidates. The processing unit 101 calculates the square of the correlation coefficient for all combinations. By the calculation processing, the processing unit 101 obtains a matrix of correlation coefficient square values as shown in FIG. 6, for example. Then, from the matrix of correlation coefficient square values, the processing unit 101 identifies the maximum correlation coefficient square value. For example, in FIG. 6, the correlation coefficient between the fluorescence spectrum of Alexa Fluor 647 and the fluorescence spectrum of APC is 0.934, and the processing unit 101 identifies this value as the maximum correlation coefficient square value (a portion surrounded by a square in the upper left of the drawing).

Note that the smaller the correlation coefficient square value is, the less similar the two phosphor spectra are. That is, the two phosphors having the maximum correlation coefficient square value can mean the two phosphors having the most similar fluorescence spectra among the phosphors included in the phosphor combination candidates.

By the above processing, the processing unit 101 identifies the maximum correlation coefficient square value for one phosphor combination candidate.

Here, in a case where the "number of phosphors belonging to a certain brightness category" is larger than the "number of biomolecules belonging to an expression level category associated with the certain brightness category", there is a plurality of combinations of phosphors selected from the certain brightness category. For example, there are six kinds of phosphor combinations ($={}_4C_2$) in a case where two phosphors are selected from four phosphors. Therefore, for example, in a case where there are three brightness categories, four phosphors belong to any of the three brightness categories, and two phosphors are selected from each brightness category, there are 216 phosphor combination candidates of 6×6×6.

In the present technology, the processing unit 101 identifies the maximum correlation coefficient square value as described above for every possible phosphor combination candidate. For example, in a case where there are 216 phosphor combination candidates, the processing unit 101 identifies the maximum correlation coefficient square value of each of the 216 phosphor combination candidates. Then, the processing unit 101 identifies a phosphor combination candidate having the smallest identified maximum correlation coefficient square value. The processing unit 101 identifies the phosphor combination candidate identified in this manner as the optimal phosphor combination.

The identification result of the optimal phosphor combination is shown in c of FIG. 5A. In c of FIG. 5A, the phosphors that make up the identified optimal phosphor combination are marked with stars.

Note that in a case where there are two or more phosphor combination candidates having the smallest maximum correlation coefficient square value, the processing unit 101 can compare the next largest correlation coefficient squares for the two or more phosphor combination candidates and identify a phosphor combination candidate having a smaller next largest correlation coefficient square value as the optimal phosphor combination. In a case where the next largest correlation coefficient square value is the same, the correlation coefficient square value next largest thereto can be compared.

In the above description, the maximum correlation coefficient square value is referred to in order to identify the optimal phosphor combination, but what is referred to in order to identify the optimal phosphor combination is not limited thereto. For example, what is referred to may be the mean value or a total value from the largest value to the nth (here, n may be any positive number, and for example, n can be two to ten, particularly two to eight, and more particularly two to five) largest value among the correlation coefficient square values. The processing unit 101 may identify the phosphor combination candidate having the smallest mean value or the smallest total value as the optimal phosphor combination.

In step S107, the processing unit 101 allocates the phosphors that make up the optimal phosphor combination identified in step S106 to the plurality of biomolecules. More specifically, the processing unit 101 allocates each of the phosphors that make up the optimal phosphor combination to the biomolecules belonging to the expression level category associated with the brightness category to which the phosphor belongs.

Figure 7:
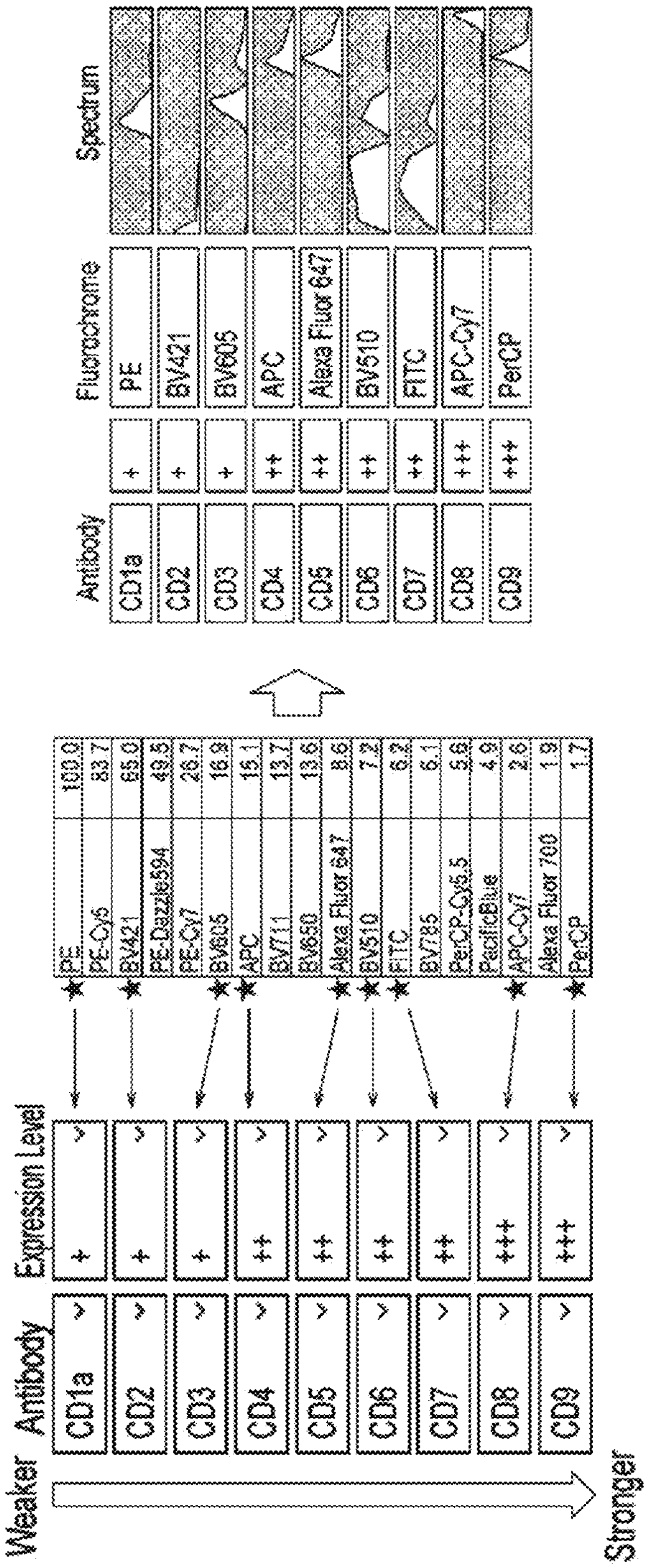
FIG. 7 is a conceptual diagram showing how to allocate a phosphor to a biomolecule.

In a case where two or more phosphors are included in one brightness category, two or more biomolecules can be included in the associated expression level category. In this case, a phosphor having a higher brightness can be allocated to a biomolecule having a lower expression level (or expected to have a lower expression level). FIG. 7 shows a conceptual diagram related to such allocation.

The processing unit 101 generates a combination of the phosphor and the biomolecule for each biomolecule by the allocation processing described above. In this manner, the processing unit 101 generates a combination list of phosphors with respect to biomolecules.

An example of the generation result of the combination list is shown in d of FIG. 5A. The processing unit 101 may output the generation result of the combination list, and in this case, for example, as in d of FIG. 5A, the processing unit 101 may display the fluorescence spectrum of each fluorochrome in addition to the combination of the biomolecule and the phosphor. By displaying the fluorescence spectrum, it is possible for the user to visually confirm whether there is no spectrum overlap.

In step S108, the processing unit 101 can cause, for example, the output unit 104 to output the combination list generated in step S107. For example, the combination list can be displayed on the display device.

In step S108, the processing unit 101 can further display reagent information corresponding to the combination of the antibody (or antigen) and the fluorochrome on the output unit 104. The reagent information can include, for example, a name of a reagent, a product number, a manufacturer name, a price, and the like. In order to display the reagent information, for example, the processing unit 101 may acquire the reagent information from a database existing outside the information processing apparatus 100 or may be acquired from a database stored inside the information processing apparatus 100 (e.g., storage unit 102).

In step S108, the processing unit 101 may further display a simulation result (e.g., various plots, etc.) regarding the separation capability in the case of using the combination list. The processing unit 101 may further display separation performance expected in the case of using the combination list.

FIG. 5B shows an example of the output result. In the example, simulation results are also shown in addition to the name of the antibody (or antigen), the name of the fluorochrome, the name of the reagent, the product number, the name of the manufacturer, the price, and the like.

By the above processing, the combination of the biomolecule and the phosphor can be optimized, and the optimized combination list can be presented to the user.

Example 1: Evaluation Using Simulation Data

Figure 25B:
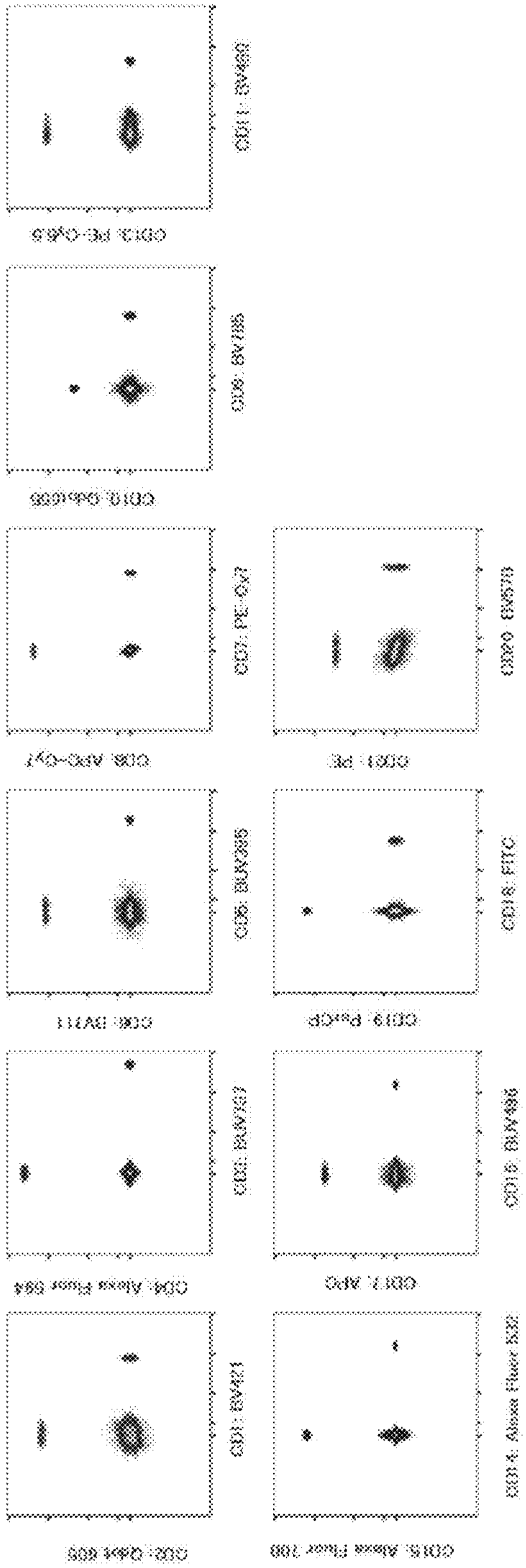
FIG. 25B is a diagram showing two-dimensional plots obtained by an experiment.

The processing as described above was performed by the information processing apparatus according to the present technology, 20 phosphors were allocated to 20 biomolecules, and a combination list of biomolecules and phosphors was generated. In order to perform the generation, the square value of the correlation coefficient described above was used as the correlation information. The fluorescence separation performance by the combination list was confirmed using simulation data. The fluorescence separation performance was evaluated using the inter-phosphor stain index. FIG. 25A shows a list of inter-phosphor stain indexes. In addition, FIG. 25B also shows two-dimensional plots obtained in the case of using the combination list.

Further, 20 phosphors were manually allocated to the 20 biomolecules, and a combination list of biomolecules and phosphors was generated. The fluorescence separation performance by the combination list was confirmed using the simulation data in a similar manner to the above. The fluorescence separation performance was evaluated using the inter-phosphor stain index. FIG. 25C shows a list of inter-phosphor stain indexes. In addition, FIG. 25D shows two-dimensional plots obtained in the case of using the combination list.

For the combination list generated by manual allocation, the inter-phosphor stain indexes were calculated, and the minimum value among the calculated inter-phosphor stain indexes was 3.36 (FIG. 25C). On the other hand, for the combination list generated according to the present technology, the inter-phosphor stain indexes were calculated, and the minimum value among the calculated inter-phosphor stain indexes was 9.98 (FIG. 25A). Therefore, it can be seen that the separation performance can be improved by the information processing apparatus according to the present technology.

Figure 25D:
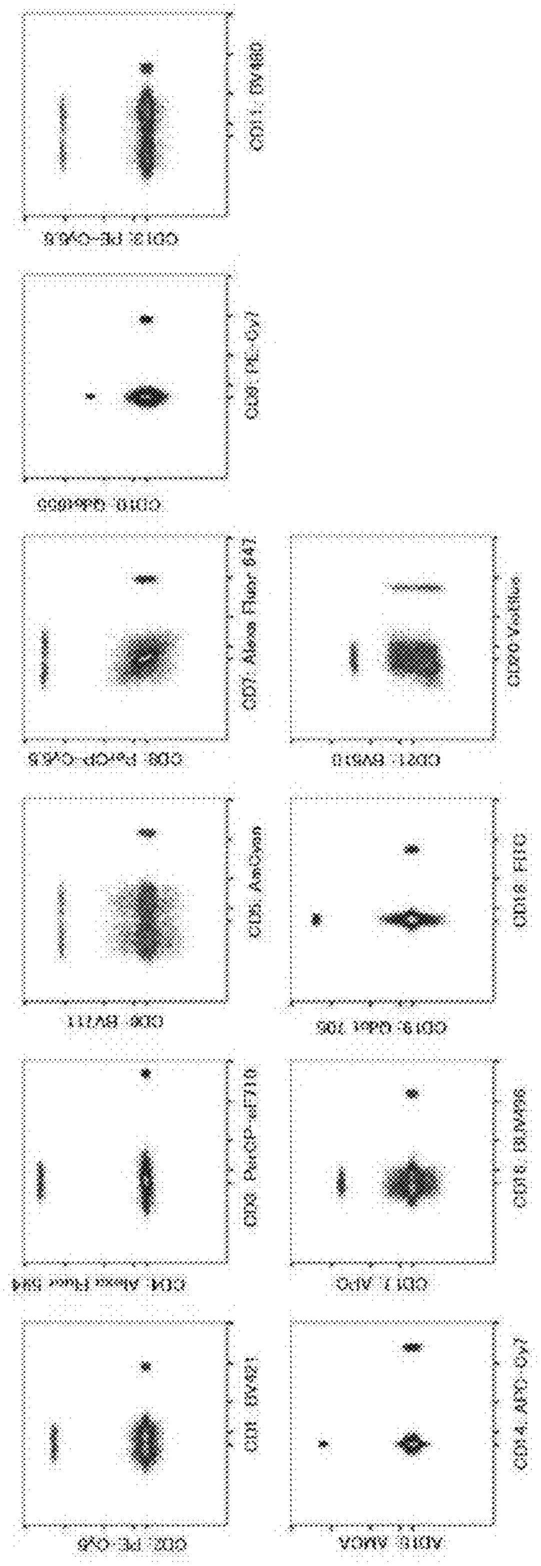
FIG. 25D is a diagram showing two-dimensional plots obtained by an experiment.

FIGS. 25B and 25D show the improved separation performance can also be confirmed by comparing the two-dimensional plots.

Further, the maximum value of the correlation coefficients between the fluorescence spectra of any two phosphors that make up the combination list generated by manual allocation was 0.957. On the other hand, the maximum value of the correlation coefficients between the fluorescence spectra of any two phosphors that make up the combination list generated according to the present technology was 0.351. Also, from this result, it can be seen that the separation performance can be performed by the information processing apparatus according to the present technology.

Example 2: Evaluation Using Cells

Figure 26A:
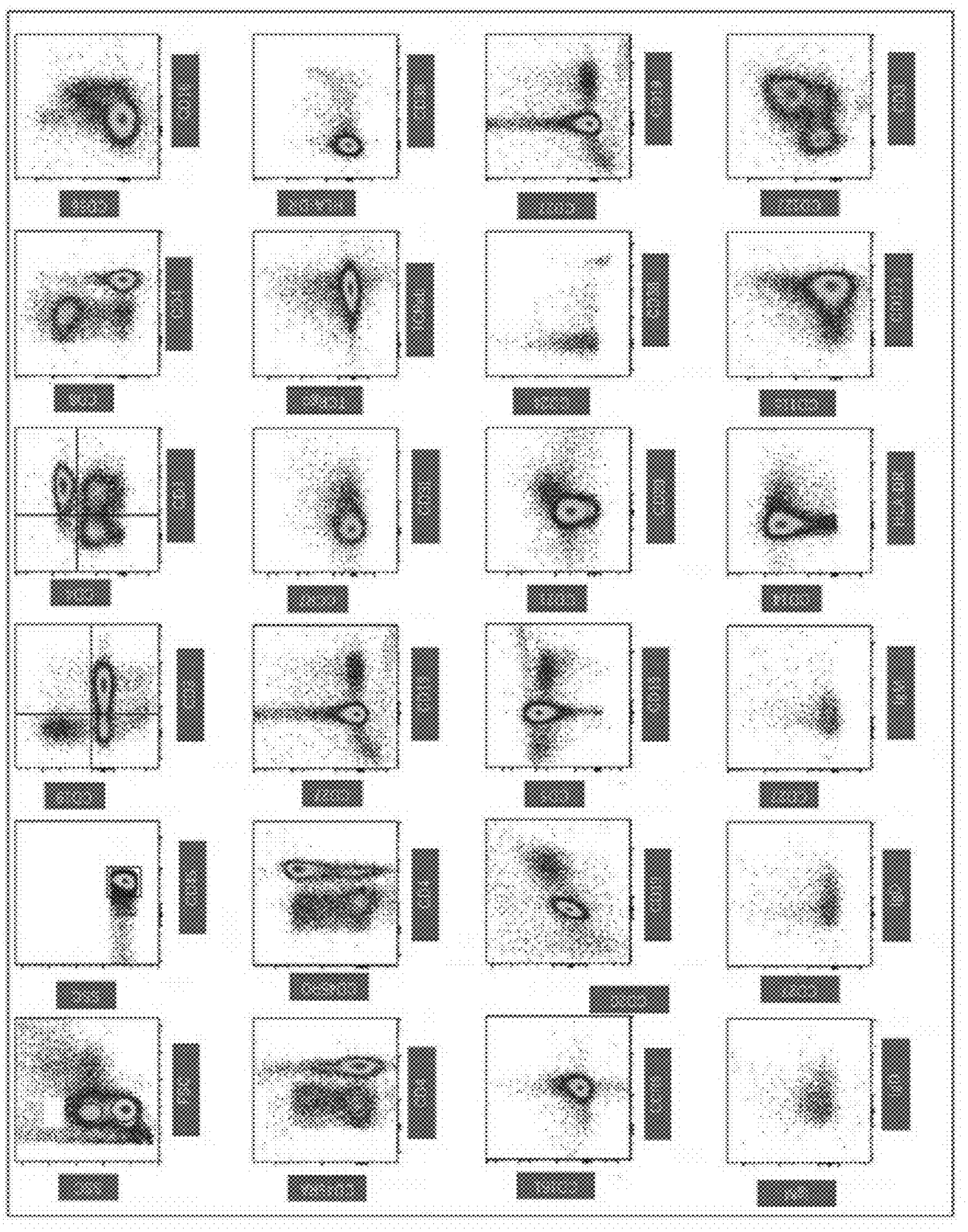
FIG. 26A is a view showing two-dimensional plots obtained by an experiment.

The processing as described above was performed by the information processing apparatus according to the present technology, 28 phosphors were allocated to 28 biomolecules, and a combination list of biomolecules and phosphors was generated. A fluorescence-labeled antibody group according to the combination list was prepared. A white blood cell-containing sample was stained using the fluorescence-labeled antibody group. The stained sample was analyzed by a flow cytometer. FIGS. 26A and 27A show two-dimensional plots group obtained by the analysis.

Figure 26B:
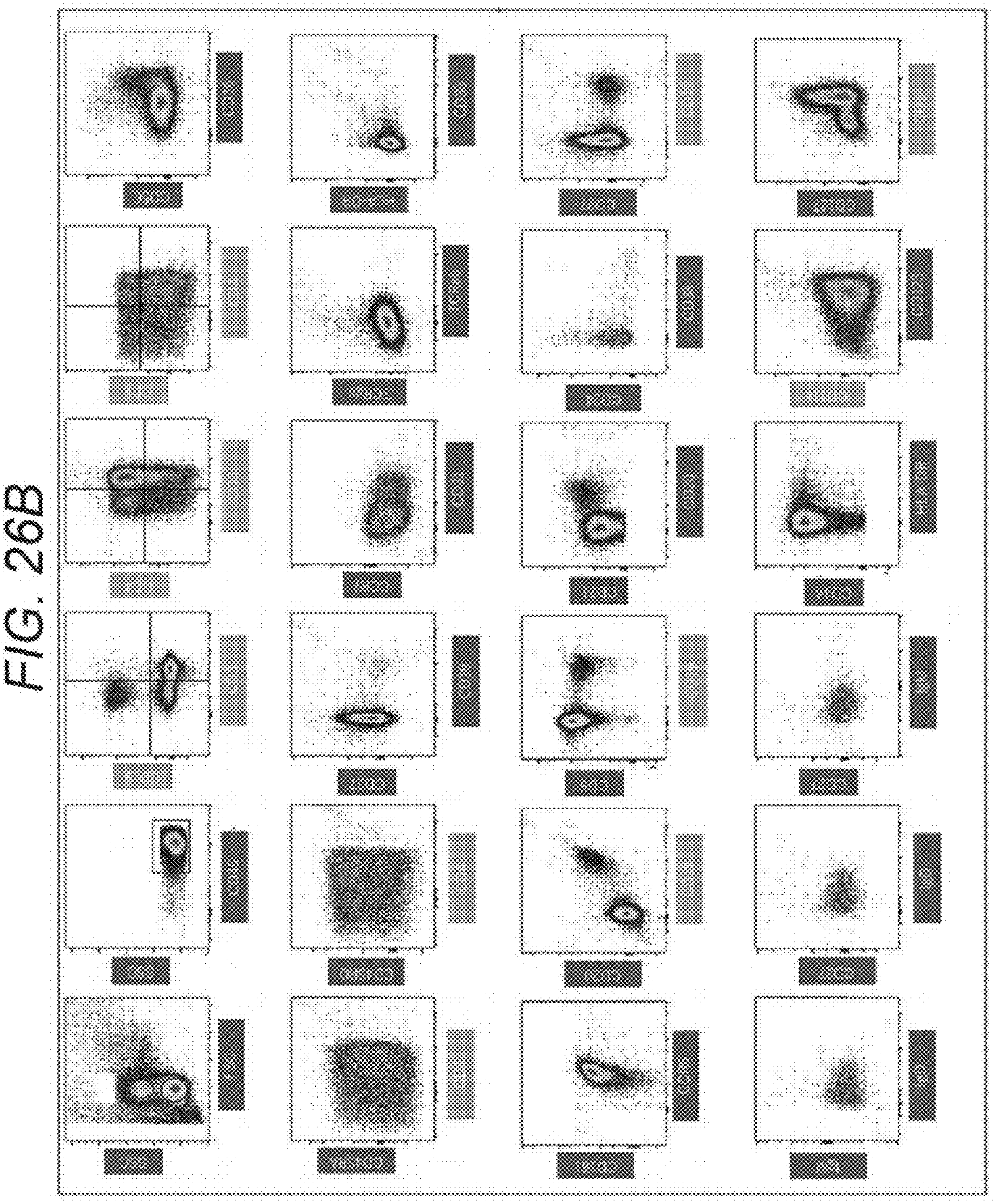
FIG. 26B is a diagram showing two-dimensional plots obtained by an experiment.

Further, 28 phosphors were manually allocated to the 28 biomolecules, and a combination list of biomolecules and phosphors was generated. A fluorescence-labeled antibody group according to the combination list was prepared. The white blood cell-containing sample was stained using the fluorescence-labeled antibody group. The stained sample was analyzed by a flow cytometer. FIGS. 26B and 27B show two-dimensional plots group obtained by the analysis.

Figure 27:
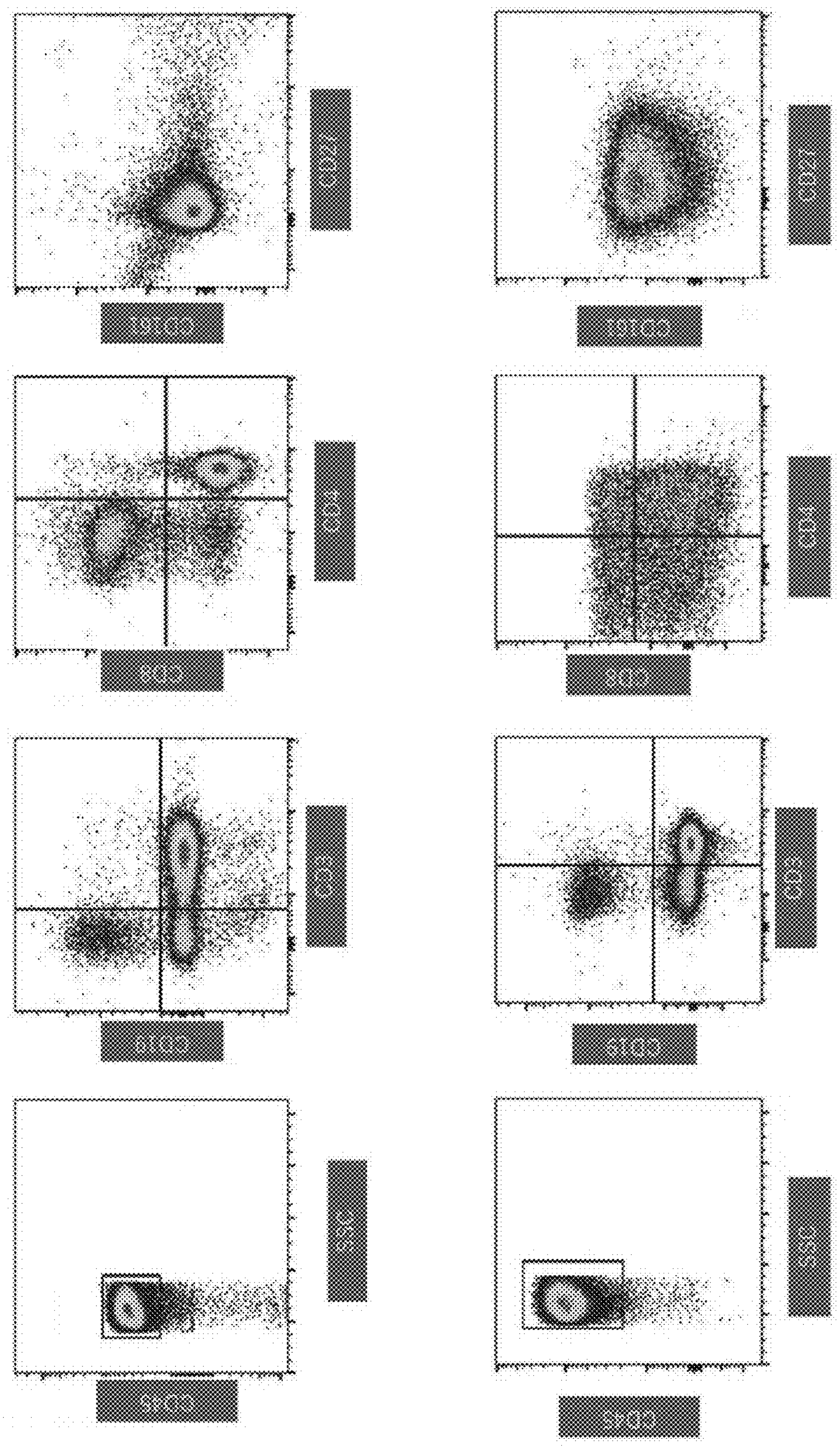
FIG. 27 is a diagram showing two-dimensional plots obtained by an experiment.

From the comparison of A and B in FIGS. 26 and 27, it can be seen that a two-dimensional plots group with improved separation performance was generated by the fluorescence-labeled antibody group according to the combination list generated by the information processing apparatus according to the present technology as compared with that by manual operation. Furthermore, it can also be seen that each cell population can be more clearly classified by the fluorescence-labeled antibody group according to the combination list generated by the information processing apparatus according to the present technology.

(3-3) Example of Processing by Processing Unit (Example of Fluorescence Spectrum Used in Calculation of Correlation Coefficient)

As described in (3-2) above, the processing unit 101 can acquire the fluorescence spectrum of each phosphor in step S103, and can then identify the optimal phosphor combination using the correlation information between the fluorescence spectra in step S106. The fluorescence spectrum used to acquire the correlation information may have a horizontal axis indicating a wavelength or a photodetector number corresponding to the wavelength, and a vertical axis indicating fluorescence intensity, particularly fluorescence intensity normalized by the maximum fluorescence intensity value.

The fluorescence spectrum used in the present technology may be a fluorescence spectrum of fluorescence generated in a case where the phosphor is irradiated with an excitation light beam having one wavelength or may be a combination of a plurality of fluorescence spectra obtained in a case where the phosphor is irradiated with excitation light beams having two or more different wavelengths, particularly one obtained by combining two or more fluorescence spectra. Hereinafter, these embodiments will be described with reference to FIG. 7.

Figure 8:
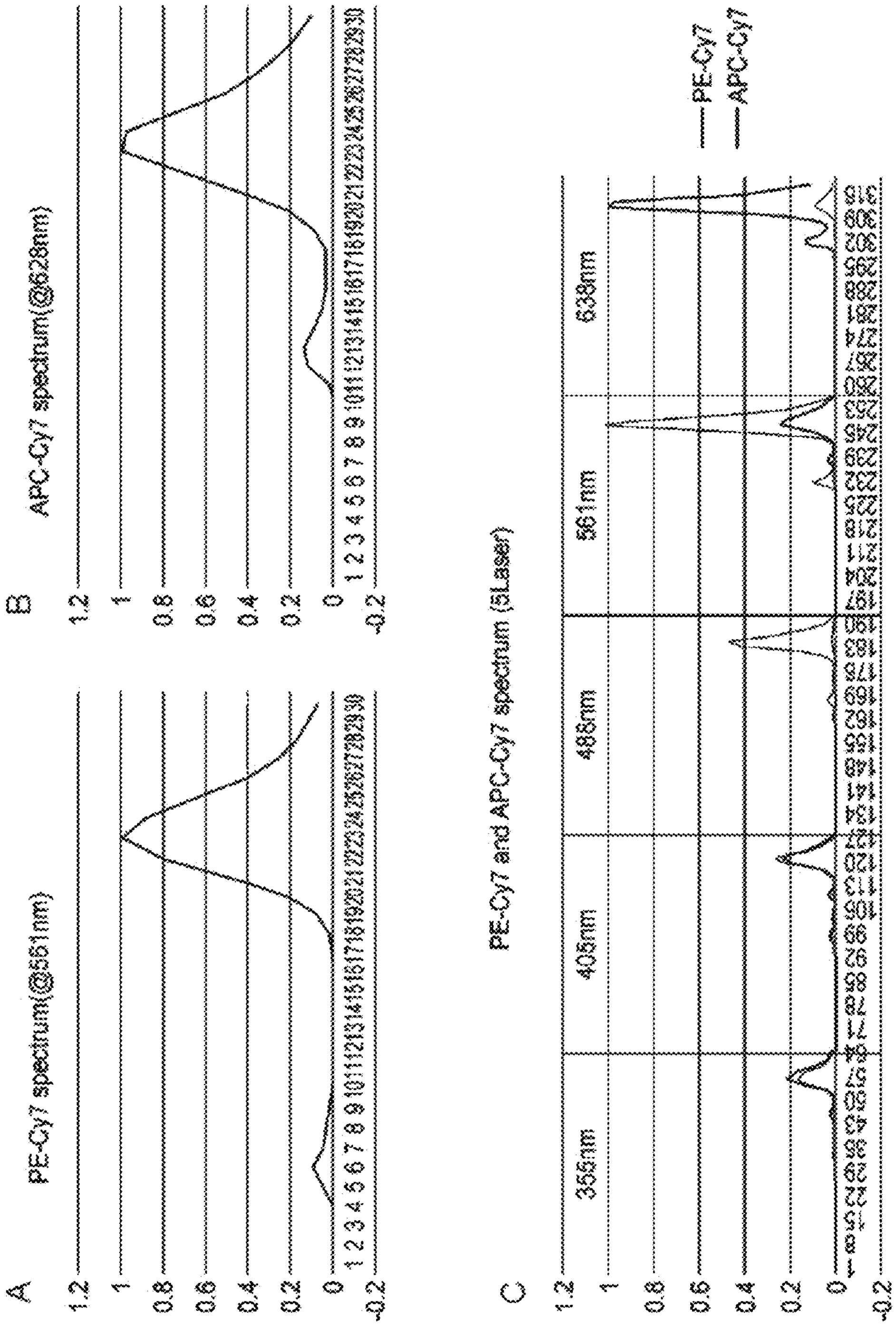
FIG. 8 is a diagram showing fluorescence spectra.

A and B of FIG. 8 show examples of fluorescence spectra of fluorescence generated in a case where the phosphor is irradiated with an excitation light beam having one wavelength. FIG. 8A is a fluorescence spectrum of fluorescence obtained in a case where PE-Cy5 is irradiated with an excitation laser of 561 nm. The horizontal axis of the fluorescence spectrum is the photodetector number corresponding to each wavelength, that is, 30 photodetectors were used to obtain the fluorescence spectrum. The vertical axis of the fluorescence spectrum is the fluorescence intensity normalized by the maximum fluorescence intensity value. FIG. 8B is a fluorescence spectrum of fluorescence obtained in a case where APC-Cy5 is irradiated with an excitation laser of 628 nm. The vertical axis and the horizontal axis of the fluorescence spectrum are the same as those in FIG. 8A.

In the present technology, a fluorescence spectrum as shown in FIG. 8A or 8B may be used. However, the fluorescence spectra of FIGS. 8A and 8B also appear to have similar spectral waveforms, and the two phosphors cannot be distinguishable.

Therefore, in the present technology, by using a combination of a plurality of fluorescence spectra obtained in a case where the phosphor is irradiated with excitation light beams having a plurality of different wavelengths, particularly one obtained by combining a plurality of fluorescence spectra, it is possible to more reliably distinguish between the two phosphors.

FIG. 8C shows an example of data obtained by combining a plurality of fluorescence spectra obtained in a case where a phosphor is irradiated with excitation light beams having a plurality of different wavelengths. The data shown in FIG. 8C is data obtained by combining five fluorescence spectra of fluorescence generated in a case where excitation laser light beams having five different wavelengths are irradiated. The five different wavelengths are 355 nm, 405 nm, 488 nm, 561 nm, and 638 nm. The horizontal axes of the five fluorescence spectra combined to obtain the data are all photodetector numbers corresponding to each wavelength, that is, 64 photodetectors were used to acquire the fluorescence spectra. In addition, the vertical axes of the five fluorescence spectra are the fluorescence intensities, and the five fluorescence spectra are normalized with the maximum value of the fluorescence intensities of the five fluorescence spectra as 1.

In FIG. 8C, a thin line is fluorescence spectrum combining data of PE-Cy5, and a thin line is fluorescence spectrum combining data of APC-Cy5. In a case where these two pieces of combining data are compared, it can be seen that the waveforms of the fluorescence spectra obtained in a case where irradiation is performed with excitation light of, for example, 488 nm, 561 nm, and 638 nm are different completely. Therefore, the fluorescence of the two fluorochromes can be more reliably distinguished using these two pieces of combining data.

As described above, in the present technology, the processing unit 101 can easily identify the optimal phosphor combination by using the combining data of the plurality of fluorescence spectra, particularly by using the combining data of the plurality of fluorescence spectra, in order to obtain the correlation information. The combination data and the combining data may be, for example, data obtained by performing predetermined normalization processing on a plurality of fluorescence spectra as described above.

Furthermore, by obtaining the correlation information using the fluorescence spectrum as described above, the same processing flow can be applied to various microparticle analyzers having different optical systems.

(3-4) Example of Processing by Processing Unit (Example of Referring to Database Regarding Availability of Reagent)

In step S103, the processing unit 101 acquires a list related to phosphors capable of labeling the biomolecule input in step S101. Then, in step S104, the phosphors included in the list are classified on the basis of brightness, and one or a plurality of brightness categories, particularly a plurality of brightness categories, is generated. At the time of generating the brightness category, the processing unit 101 may preferably refer to a reagent database having information regarding whether a reagent obtained by combining a biomolecule and a phosphor can be obtained (e.g., can be purchased). For example, in step S103, the processing unit 101 can refer to the reagent database and form the list so as to include only phosphors constituting available reagents. Alternatively, in step S104, the processing unit 101 can refer to the reagent database and form each brightness category so as to include only phosphors constituting available reagents. In this manner, the processing unit 101 can prevent a phosphor constituting an unavailable reagent from being classified into each brightness category. This makes it possible to reduce the amount of calculation in the processing according to the present technology, particularly the processing for calculating the correlation information.

In step S107, the processing unit 101 performs processing of allocating the phosphor to the biomolecule. The processing unit 101 may refer to the reagent database in the allocation processing. For example, in the allocation processing, the processing unit 101 can refer to the reagent database and generate only a combination of a phosphor and a biomolecule constituting an available reagent by the allocation processing.

More specifically, after allocating a certain phosphor to a certain biomolecule, the processing unit 101 refers to the reagent database, and in a case where there is a reagent obtained by combining the certain phosphor and the certain biomolecule in the reagent database, the combination is included in the combination list. Further, in a case where there is no reagent obtained by combining the certain phosphor and the certain biomolecule in the reagent database, the combination is not made to be included in the combination list, and then, the processing unit 101 can perform processing of allocating the certain phosphor to another biomolecule and perform similar reagent database reference processing.

By referring to the reagent database having the information regarding availability of the reagent described above, it is possible to present information to the user while limiting to available reagents. As described above, in the present technology, the plurality of phosphors that make up the brightness category may be identified on the basis of data regarding whether a complex of a phosphor and a biomolecule is available.

(3-5) Example of Processing by Processing Unit (Example of Adjusting Number of Phosphors Classified into Each Brightness Category)

In step S104, the processing unit 101 classifies the phosphors on the basis of the brightness of each phosphor and generates a plurality of brightness categories. The information processing apparatus of the present technology may be configured to be able to change the criteria of the classification.

For example, as described in (3-2) above, the numerical range of the amount of fluorescence or the fluorescence intensity may be associated with each brightness category, and the phosphor may be classified into a brightness category in accordance with the amount of fluorescence or the fluorescence intensity of the phosphor.

Figure 9:
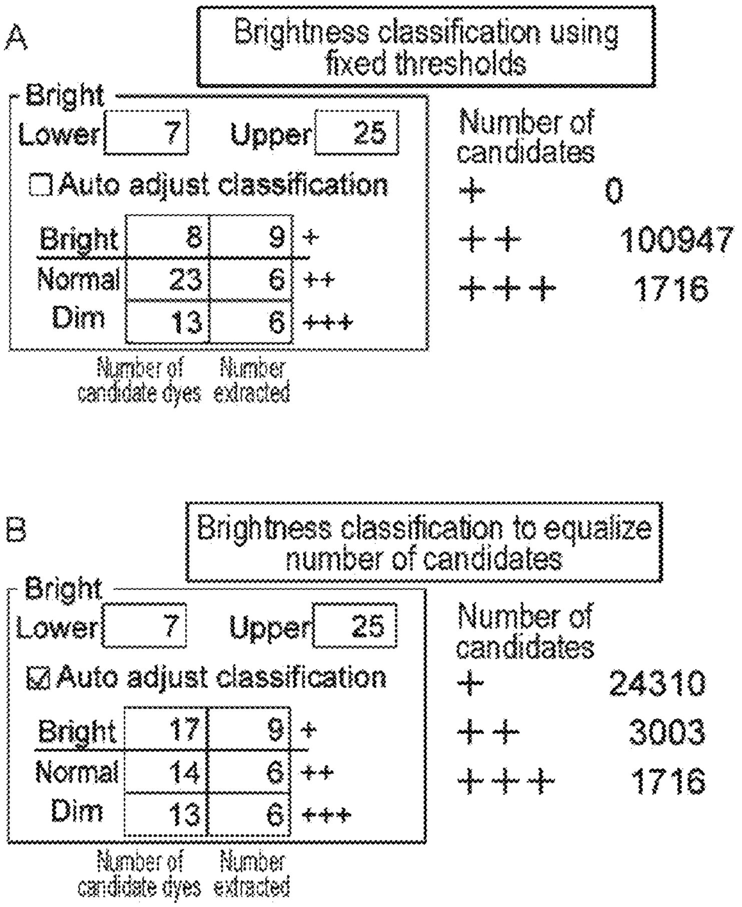
FIG. 9 is a diagram for explaining the adjustment of brightness categories.

However, depending on the biomolecule and the expression level thereof, which are input by the user, the number of biomolecules belonging to the expression level category can be larger than the number of phosphors belonging to the brightness category associated with the expression level category. In addition, it is also desirable to eliminate the bias of the number of combination candidates for each brightness category. Therefore, by adjusting the number of phosphors classified into each brightness category, an error that no candidate is found hardly occurs. The adjustment of the number of phosphors classified into each brightness category will be described below with reference to FIG. 9.

FIG. 9A shows an example of a window that displays a result of classifying phosphors in accordance with fixed brightness thresholds. In FIG. 9A, "8", "23", and "13" phosphors are classified into three brightness categories "Bright", "Normal", and "Dim", respectively ("Number of candidate dyes" column). Here, the number of biomolecules belonging to the expression level category associated with the brightness category "Bright" is "9" ("Number extracted" column), the number of biomolecules is larger, and the number of candidates of the combination related to the allocation of the phosphor to the biomolecule is 0.

Therefore, for example, the processing unit 101 can change the classification criterion of the brightness category in response to the user clicking the checkbox of "Auto adjust classification" displayed in the above window. In one embodiment of the present technology, the processing unit 101 can change the numerical range of the amount of fluorescence or the fluorescence intensity associated with each brightness category such that the "Difference between the number of phosphors classified into brightness category and the number of biomolecules belonging to the expression level category associated with the brightness category" is comparable over all the brightness categories. For example, the processing unit 101 can change the numerical range of the amount of fluorescence or the fluorescence intensity associated with each brightness category such that the condition of "a difference value between the difference for one brightness category and the difference for another brightness category is, for example, 3 or less, preferably 2 or less, and more preferably 1 or less" is satisfied for all combinations of the two brightness categories of the total brightness categories.

FIG. 9B shows an example of the window after the classification criterion is changed. As shown in the drawing, the number of phosphors classified into the brightness category "Bright" has been changed to "17", and the difference between this number and the number of biomolecules belonging to the expression level category associated with the brightness category "Bright" is "8". For other brightness categories, the difference is 8 or 7. As a result, it is possible to eliminate the bias in the number of combination candidates for allocation of biomolecules to phosphors.

As described above, in the present technology, the processing unit 101 can adjust the number of phosphors belonging to each brightness category in accordance with the number of biomolecules belonging to each expression level category.

Note that in the present technology, the processing unit 101 may accept a change in the numerical range associated with each brightness category by the user, and in accordance with the change, the processing unit 101 may change the number of phosphors classified into the brightness category after the change.

(3-6) Example of Processing by Processing Unit (Example in which Information Regarding Priority is Associated with Each Phosphor, and Phosphors to be Used in Optimization are Limited in Accordance with Number of Selected Phosphors)

In a preferred embodiment of the present technology, the information regarding the priority may be associated with each phosphor included in the phosphor data acquired in step S103, or the information regarding the priority may be associated with each phosphor in any step after the phosphor data is acquired in step S103. For example, in accordance with the number of biomolecules to which the phosphors are allocated, the processing unit 101 can limit the selectable phosphors to the phosphors with high priority for the user with reference to the information regarding the priority. This limitation enables the processing load of the processing unit 101 to be reduced and the optimization to be executed at a higher speed.

The present embodiment is also advantageous from the following viewpoints. That is, for example, among commercially available fluorochromes, there are rare fluorochromes that are not handled by a plurality of manufacturers. Such fluorochromes are generally more expensive and tend to take longer to deliver after order placement. Therefore, a user who performs analysis such as flow cytometry tends to adopt main fluorochromes as fluorochromes used in the staining process. Therefore, as described above, in the panel design, the phosphors to be adopted are limited to phosphors with high priority, whereby rare fluorochromes can be prevented from being easily included in the panel.

In the present embodiment, the information regarding the priority may be, for example, a value indicating a priority order (hereinafter also referred to as "priority order value"), a code indicating a priority order, or the like. The values and the reference numerals may be appropriately set by those skilled in the art.

In the present embodiment, the list related to phosphors can include, for example, information regarding the name, brightness, and priority of each phosphor. FIG. 10A shows an example of the list in the present embodiment. The list related to phosphors shown in FIG. 10A can have a name ("name" column) and a priority order value ("value" column) for each phosphor.

In the present embodiment, the processing unit 101 can refer to the number of biomolecules (e.g., the number of biomolecules input in step S101) and limit the phosphors usable in the generation of the brightness category from the list related to phosphors. In order to perform the limitation, the processing unit 101 can refer to priority order processing data defining the relationship between the number of biomolecules and the information regarding the priority. FIG. 10B shows a content example of the priority order processing data. As shown in FIG. 10B, the priority order processing data associates the number of biomolecules (particularly, a range of the number) with the priority order value (particularly, a range of the priority order value). For example, the number of biomolecules "0 to 10" is associated with the priority order value "1000".

The processing unit 101 can refer to the priority order processing data and use only the phosphors having the priority order values corresponding to the number of biomolecules in the processing of step S103 and subsequent steps.

For example, in the classification based on the brightness of the phosphor in step S104, the processing unit 101 can refer to the priority order processing data, classify only the phosphor having the information regarding the priority corresponding to the number of biomolecules on the basis of the brightness, and generate the brightness category including only the phosphor having the information regarding the priority. For example, in a case where the number of biomolecules is zero to ten, the processing unit 101 can refer to the above priority order processing data in step S104, classify only the phosphors having the priority order value of 1000 on the basis of the respective brightness, and generate brightness categories.

As described above, in the present technology, the processing unit 101 can identify a plurality of phosphors included in the brightness category on the basis of the information regarding the priority associated with the phosphor.

The information processing apparatus 100 according to the present technology may be configured to be able to switch between processing using the information regarding the priority and processing not using the information regarding the priority. The processing unit 101 can cause the output unit 104 to display a window that enables the switching. In addition, the processing unit 101 may cause the output unit 104 to display a window that displays a change of the phosphor selectable in the processing in accordance with the switching. FIG. 100 shows an example of such a window. On the left side of FIG. 100, all checkboxes for the listed phosphors have been checked, that is, it is shown that all phosphors are selectable. On the other hand, on the right side of FIG. 10, some of the checkboxes of the phosphors listed have not been checked (portions surrounded by a square). It is thereby possible to confirm a phosphor that can be selected and a phosphor that cannot be selected in the processing.

Example 3: Comparison of Whether Information Regarding Priority is Used

The information processing apparatus according to the present technology was used to allocate 15 phosphors to 15 antibodies and generate a combination list using the information regarding the priority as described above. The number of phosphors present as allocation candidates was 44. The time required to generate the combination list was measured.

Similarly, the information processing apparatus according to the present technology was used to allocate 20 phosphors to 20 antibodies and generate a combination list using the information regarding priority as described above. The number of phosphors present as allocation candidates was 44. The time required to generate the combination list was measured.

The measured time is shown in the "limitation on" column of FIG. 28.

A combination list was generated by allocating 15 phosphors to 15 antibodies in a similar manner except that the information regarding the priority was not used. The time required to generate the combination list was measured.

A combination list was generated by allocating 20 phosphors to 20 antibodies in a similar manner except that the information regarding the priority was not used. The time required to generate the combination list was measured.

The measured time is shown in the "limitation off" column in FIG. 28.

As shown in FIG. 28, by using the information regarding the priority, the processing time required to generate the combination list has been reduced greatly. It can thus be seen that the combination list can be generated faster by using the information regarding the priority.

(3-7) Example of Processing by Processing Unit (Example of Executing Separation Capability Evaluation)

In a preferred embodiment of the present technology, the processing unit 101 can evaluate the separation capability for the generated combination list. For example, the processing unit 101 can generate simulation data regarding the generated combination list and evaluate the separation capability regarding the combination list by using the simulation data. By performing the evaluation of the separation capability, the accuracy of optimization can be enhanced. For example, by executing the evaluation of the separation capability, it is possible to confirm whether the combination list generated in step S107 exhibits desired separation performance, or it is also possible to generate a combination list exhibiting better separation performance in accordance with the confirmation result.

In the present embodiment, for example, the processing unit 101 can further generate a modified combination list in which at least one phosphor of a set of phosphors included in the combination list is changed to another phosphor in accordance with a result of the evaluation of the separation capability and further performs separation capability evaluation related to the modified combination list. By generating the modified combination list and then performing the separation capability evaluation, a combination list that exhibits better separation performance can be generated.

Figure 11:
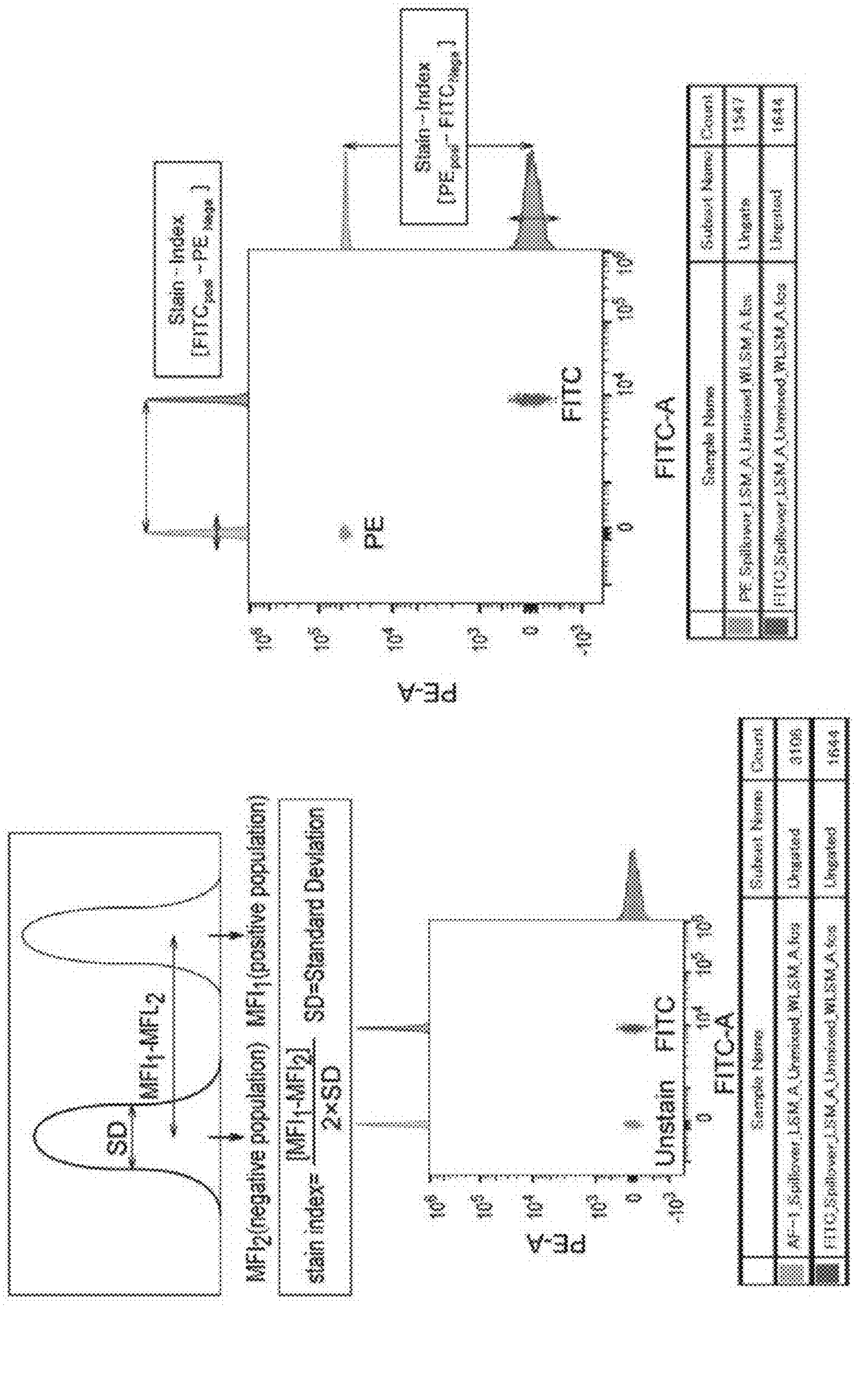
FIG. 11 is a diagram for explaining a stain index.
Figure 12:
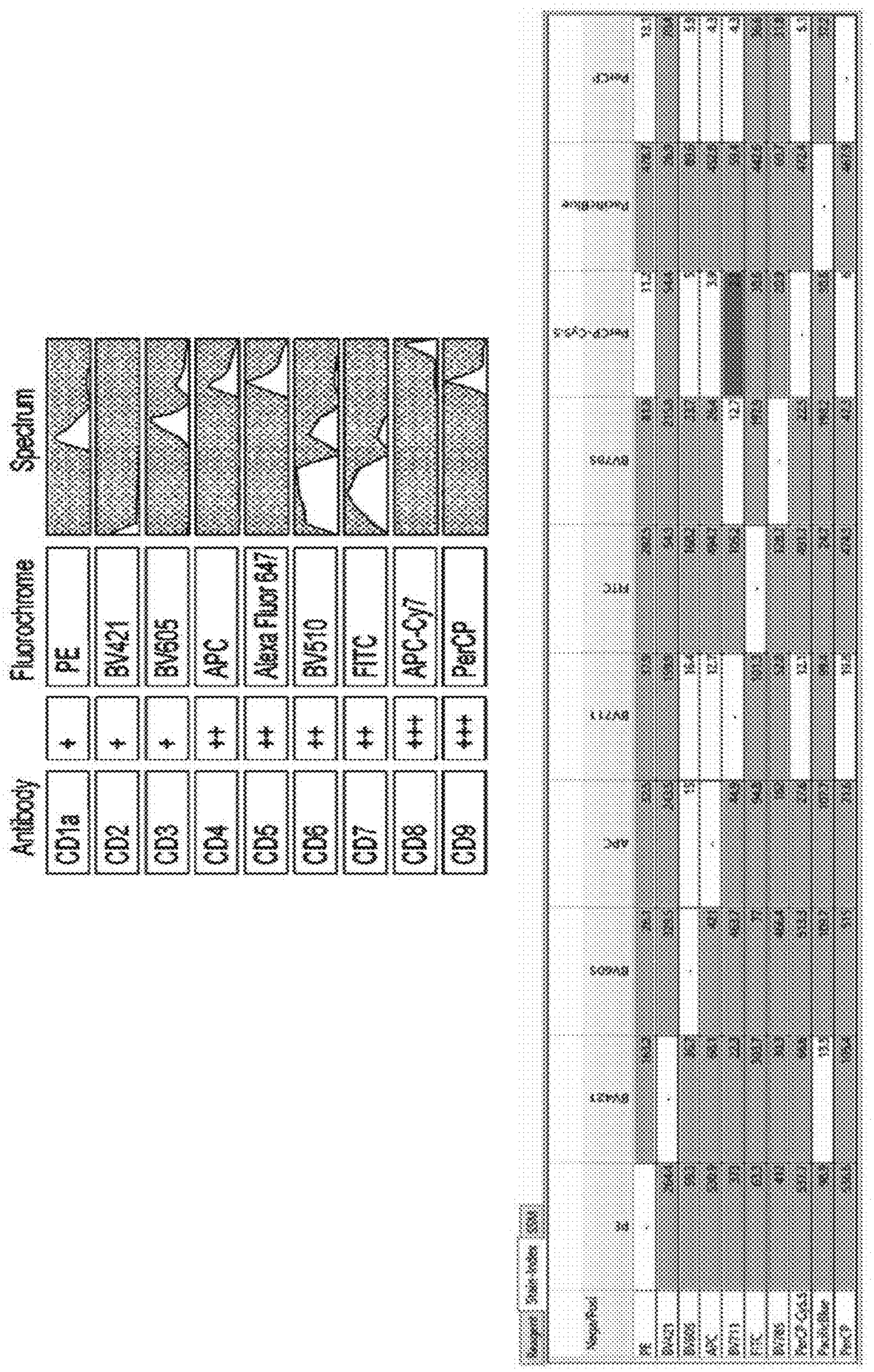
FIG. 12 is a diagram showing an example of calculation results of inter-phosphor stain indexes.

The evaluation of the separation capability is, for example, an evaluation using a stain index (Stain-Index), and more preferably, an evaluation using a stain index between phosphors. In the art, the stain index is an index indicating the performance of the phosphor (fluorochrome) itself and is defined by the amounts of fluorescence of the stained particles and the unstained particles and the standard deviation of the unstained particle data, for example, as shown in the left of FIG. 11. The unstained particle data replaced with particles stained with another phosphor is the stain index between the phosphors, for example, as shown on the right side of FIG. 11. By using the stain index between the phosphors, it is possible to evaluate the separation performance between the phosphors in consideration of the leakage amount due to the overlapping of the fluorescence spectra, the amount of fluorescence, and noise. FIG. 12 shows an example of a result of calculating inter-phosphor stain indexes for all combinations of two phosphors in the phosphor group that makes up the generated combination list.

Note that the processing unit 101 of the present technology can cause the output unit 104 to output a result of calculation for all combinations of two phosphors in the phosphor group that makes up the combination list generated by the processing unit. This facilitates the user to evaluate the separation performance.

For example, in a table of inter-phosphor stain indexes as shown in FIG. 12, the smaller the number of regions having small numerical values of the inter-phosphor stain indexes, the better the separation performance. In the present technology, first, a combination list may be generated on the basis of the expression level category, the brightness category, and the correlation information, and then, separation capability evaluation using an index such as a stain index may be performed. For example, in the generated combination list, a phosphor combination having poor separation performance can be known by the separation capability evaluation, and a panel having better separation performance can be designed by changing the phosphor combination.

Further, performing panel design by performing the generation of the combination list based on the categories and the like and the separation capability evaluation, described above (and panel correction as necessary) can reduce calculation time much more than performing panel design by performing separation capability evaluation for every combination.

Figure 13:
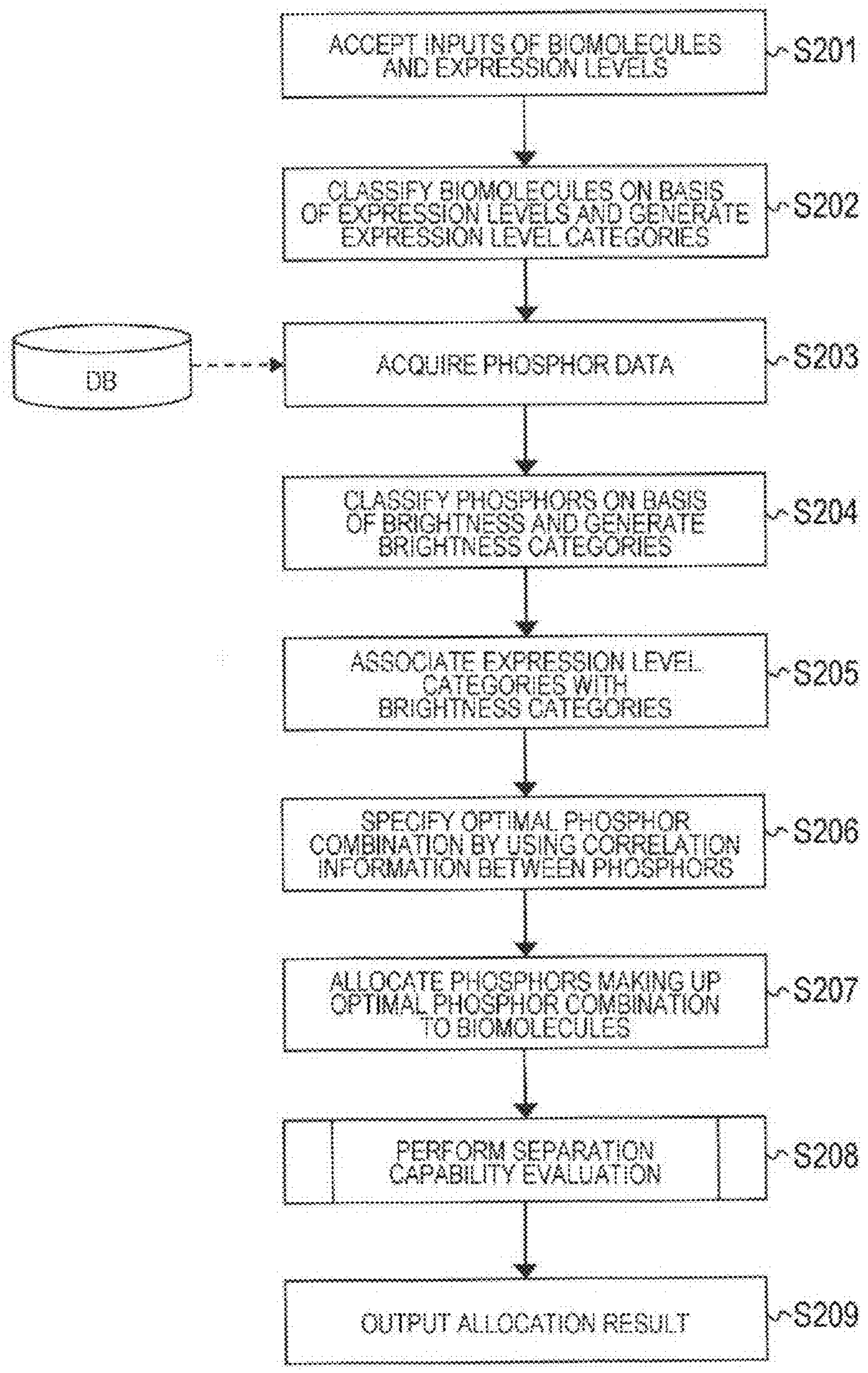
FIG. 13 is a flowchart of processing executed by the information processing apparatus according to the present technology.

Hereinafter, an example of a processing flow in the present embodiment will be described with reference to FIGS. 13 and 14. In the processing flow shown in FIG. 13, steps S201 to S207 and S209 are the same as steps S101 to S107 and S108 described with reference to FIG. 4, and the description thereof also applies to steps S201 to S207 and S209.

In step S208, the processing unit 101 evaluates the separation capability for the phosphor group that makes up the combination list generated by the allocation processing in step S207. An example of a more detailed processing flow of step S208 will be described with reference to FIG. 14.

In step S301 of FIG. 14, the processing unit 101 starts separation capability evaluation processing.

In step S302, the processing unit 101 calculates a stain index between phosphors (the stain index is also referred to as "SI" in the present specification). The SI can be obtained using, for example, data obtained by generating simulation data using the combination list generated in step S207 and performing unmixing processing on the simulation data using spectral reference.

Here, the simulation data may be, for example, a data group as if measured by a device (e.g., flow cytometer) in which analysis is performed using reagents according to a combination list. In a case where the device is a microparticle analyzer such as a flow cytometer, for example, the device can be a data group obtained in a case where 100 to 1000 microparticles are actually measured. For the generation of the data group, conditions such as noise, staining variation, and the number of generated data of the device may be considered.

Figure 15:
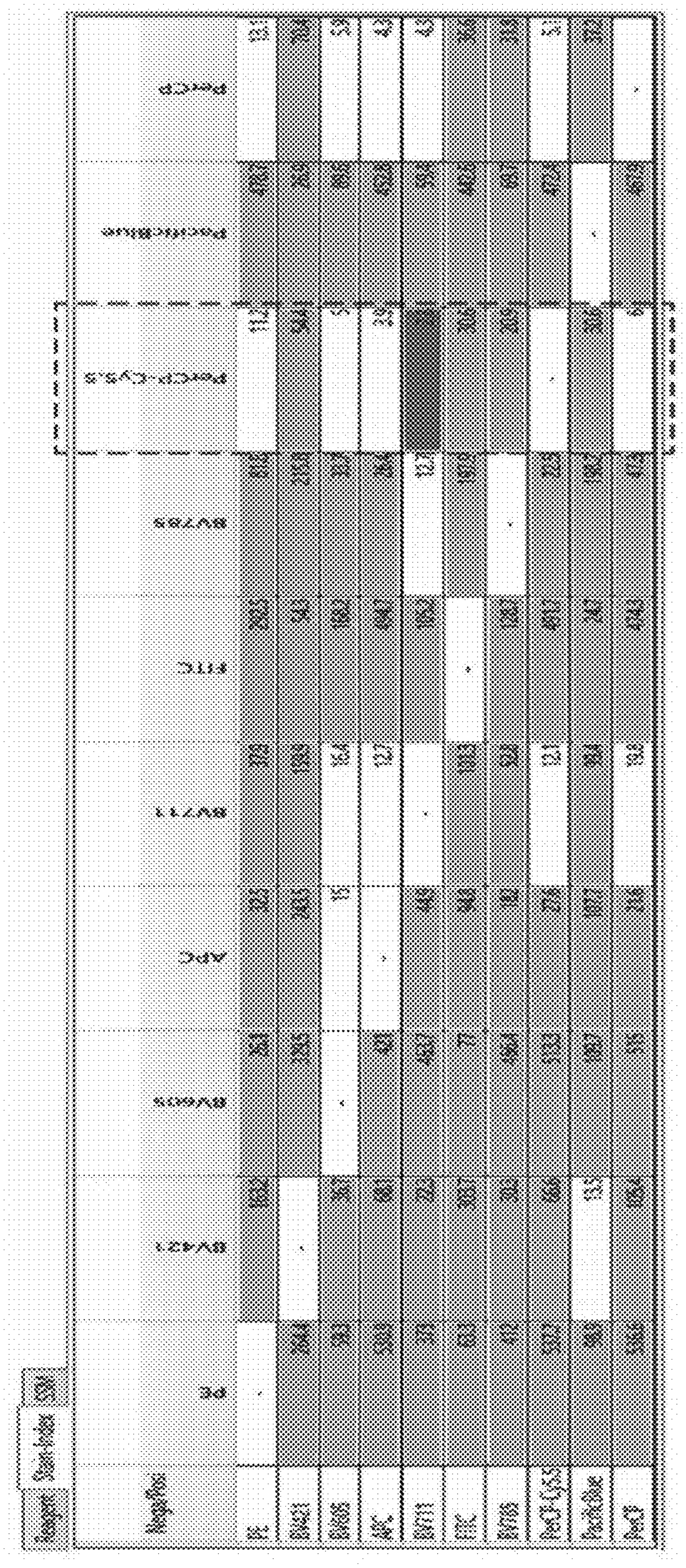
FIG. 15 is a diagram showing an example of data of inter-phosphor SI.

In step S302, the processing unit 101 can acquire inter-phosphor SI data as shown in FIG. 15, for example. The data includes all SIs between two different phosphors in the phosphor group that makes up the combination list.

In step S303, the processing unit 101 identifies one or a plurality of phosphors having poor separation performance, particularly one phosphor having poor separation performance, on the basis of the calculated inter-phosphor SIs. For example, the processing unit 101 can identify a phosphor treated as positive out of two phosphors for which the smallest inter-phosphor SI is calculated as one phosphor having poor separation performance.

For example, with respect to the inter-phosphor SI data shown in FIG. 15, in step S303, the processing unit 101 identifies the phosphor "PerCP-Cy5.5" treated as positive (posi) out of the two phosphors for which the smallest inter-phosphor SI "2.8" is calculated as one phosphor having poor separation performance.

In step S304, the processing unit 101 identifies a candidate phosphor that replaces the phosphor having poor separation performance identified in step S303. The candidate phosphors can be identified, for example, as follows. First, the processing unit 101 refers to a brightness category to which the phosphor having poor separation performance belongs, and can identify a phosphor not adopted in the combination list among phosphors belonging to the brightness category as a candidate phosphor. In addition, the processing unit 101 may select the candidate phosphor from the brightness category having the closest brightness to the brightness category to which the phosphor having poor separation performance belongs. The processing unit 101 can identify a phosphor not adopted in the combination list among phosphors belonging to the closest brightness category as a candidate phosphor.

Figure 16:
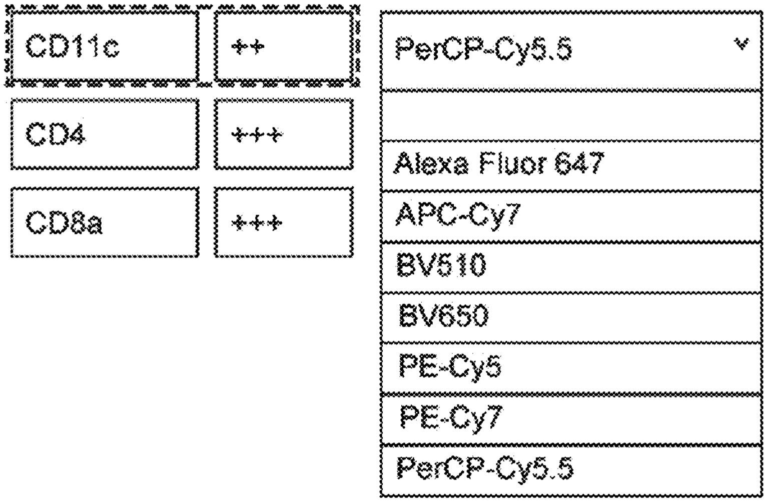
FIG. 16 is a view showing an example of a window in which a candidate phosphor that replaces a phosphor having poor separation performance is displayed.

For example, in FIG. 16, the processing unit 101 identifies six phosphors such as "Alexa Fluor 647" as candidate phosphors to replace the phosphor "PerCP-Cy5.5" having poor separation performance. In this manner, a plurality of candidate phosphors may be identified, or only one candidate phosphor may be identified.

In step S305, the processing unit 101 calculates an inter-phosphor SI in a case where the phosphor having poor separation performance identified in step S304 is changed to a candidate phosphor. This calculation may be performed for each of all of the candidate phosphors.

FIGS. 17A and 17B show examples of the calculation result. In FIGS. 17A and 17B, for each of the six phosphors mentioned with reference to FIG. 16, the inter-phosphor SIs in a case where the phosphor having poor separation performance is changed to the candidate phosphor are shown.

In step S306, the processing unit 101 selects, as a phosphor that replaces the phosphor having poor separation performance, a candidate phosphor for which a calculation result having the largest minimum value of the inter-phosphor SI has been obtained among the calculation results in step S305.

For example, regarding the calculation results in FIGS. 17A and 17B, the minimum value of the inter-phosphor SI related to "BV650" is the largest among the minimum values of the inter-phosphor SI in the calculation results of the six candidate phosphors. Therefore, the processing unit 101 selects "BV650" as a phosphor replacing "PerCP-Cy5.5".

In step S307, the processing unit 101 determines whether there is a phosphor combination better than the combination list obtained by replacing the phosphor having poor separation performance with the phosphor selected in step S306. For this determination, for example, steps S303 to S306 may be repeated.

In a case where there is a combination in which the minimum value of the inter-phosphor SI becomes larger as a result of repeating steps S303 to S306, the processing unit 101 determines that there is a better phosphor combination. In a case where the determination is made in this manner, the processing unit 101 returns the processing to step S303.

In a case where there is no combination in which the minimum value of the inter-phosphor SI becomes larger as a result of repeating steps S303 to S306, the processing unit 101 determines that there is no better phosphor combination. In the case of determining that there is no better phosphor combination, the processing unit 101 identifies a phosphor combination in a stage immediately before the repetition of steps S303 to S306 as an optimized combination list and advances the processing to step S308.

In step S308, the processing unit 101 ends the separation capability evaluation processing and advances the processing to step S209.

By the processing as described above, it is possible to present a combination list of biomolecules and phosphors that have been optimized in consideration of separation capability.

Example 4: Comparison of Performance or Non-Performance of Separation Capability Evaluation A comparison was made between a combination list generated without performing the separation capability evaluation in step S208 (hereinafter referred to as "combination list without separation capability evaluation") and a combination list generated performing the separation capability evaluation in step S208 (hereinafter referred to as "combination list with separation capability evaluation") in the processing according to the present technology described above.

Figure 29A:
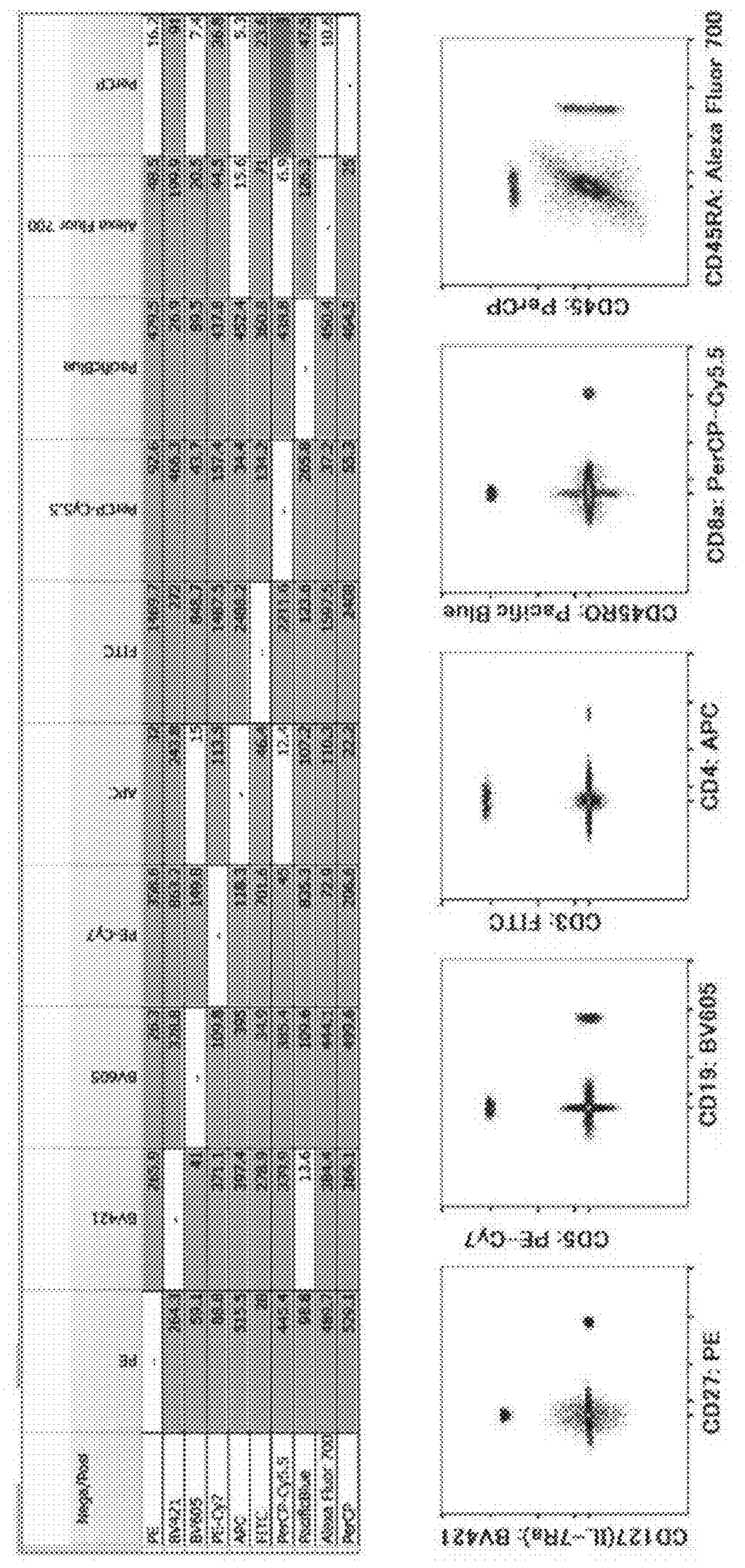
FIG. 29A is a diagram showing inter-phosphor stain indexes and two-dimensional plots obtained by an experiment.
Figure 29B:
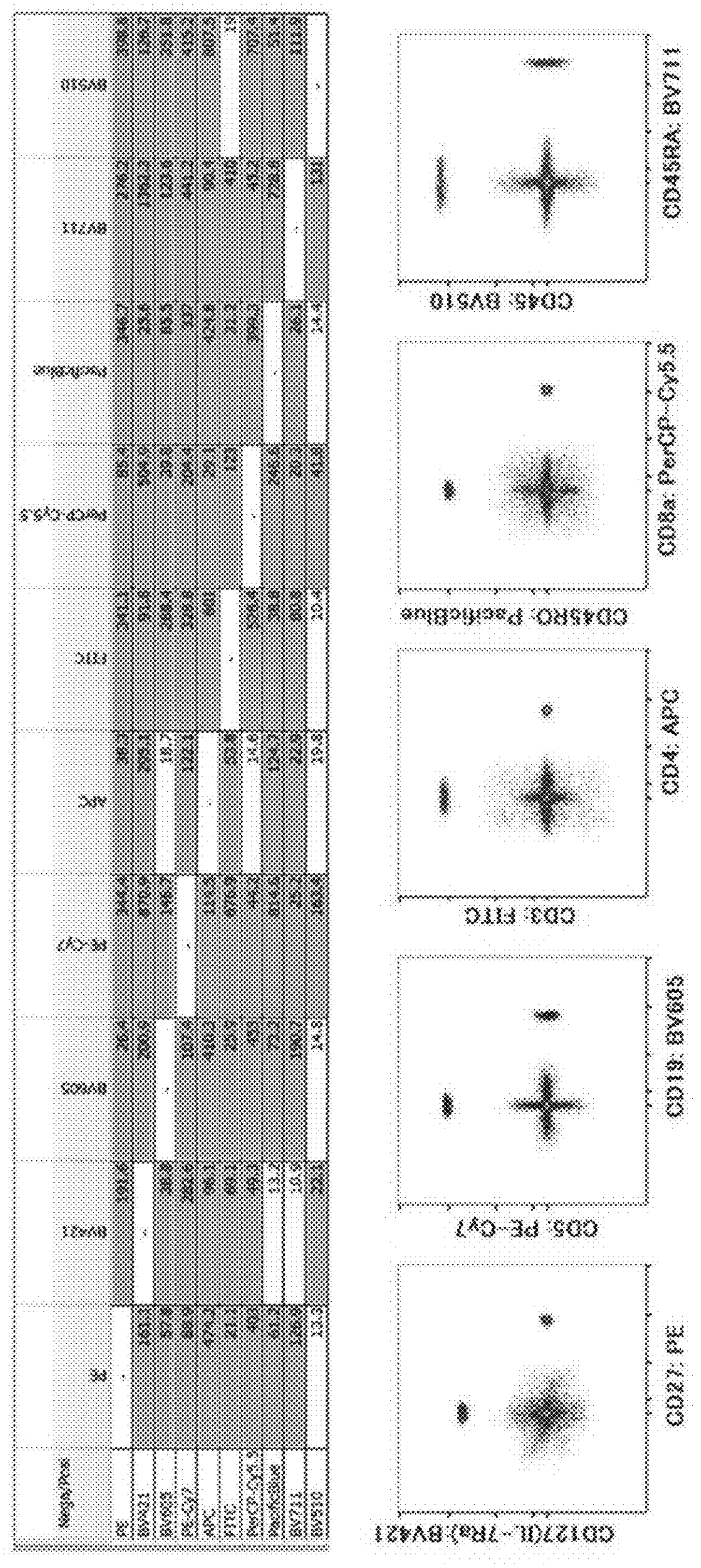
FIG. 29B is a diagram showing inter-phosphor stain indexes and two-dimensional plots obtained by an experiment.

The fluorescence separation performance of each of these combination lists was confirmed using simulation data. The fluorescence separation performance was evaluated using the inter-phosphor stain index. Further, two-dimensional plots were also generated using these combination lists. FIG. 29A shows inter-phosphor stain indexes of a combination list without separation capability evaluation and two-dimensional plots generated by the list. FIG. 29B shows inter-phosphor stain indexes of a combination list with separation capability evaluation and two-dimensional plots generated by the list.

The comparison of FIGS. 29A and 29B shows that the combination list with separation capability evaluation was superior in separation performance to the combination list without separation capability evaluation. It can be seen therefrom that the separation performance can be further improved by evaluating the separation capability.

(3-8) Example of Processing by Processing Unit (Processing Flow in Consideration of Reagent Cost)

As described in (3-2) above, in step S107, the processing unit 101 allocates the phosphors that make up the optimal phosphor combination identified in step S106 to the plurality of biomolecules. In this allocation processing, the reagent cost may be considered. That is, in a preferred embodiment of the present technology, the processing unit 101 can generate the combination list on the basis of cost information regarding a complex of a biomolecule and a phosphor. The complex can be, for example, an antibody labeled with a fluorochrome. For example, the processing unit 101 may calculate the cost required to prepare a set of reagents (e.g., a set of fluorescence-labeled antibodies) according to the combination list with reference to the cost information. The processing unit 101 can further output the cost together with the output of the combination list in step S108.

Figure 18:
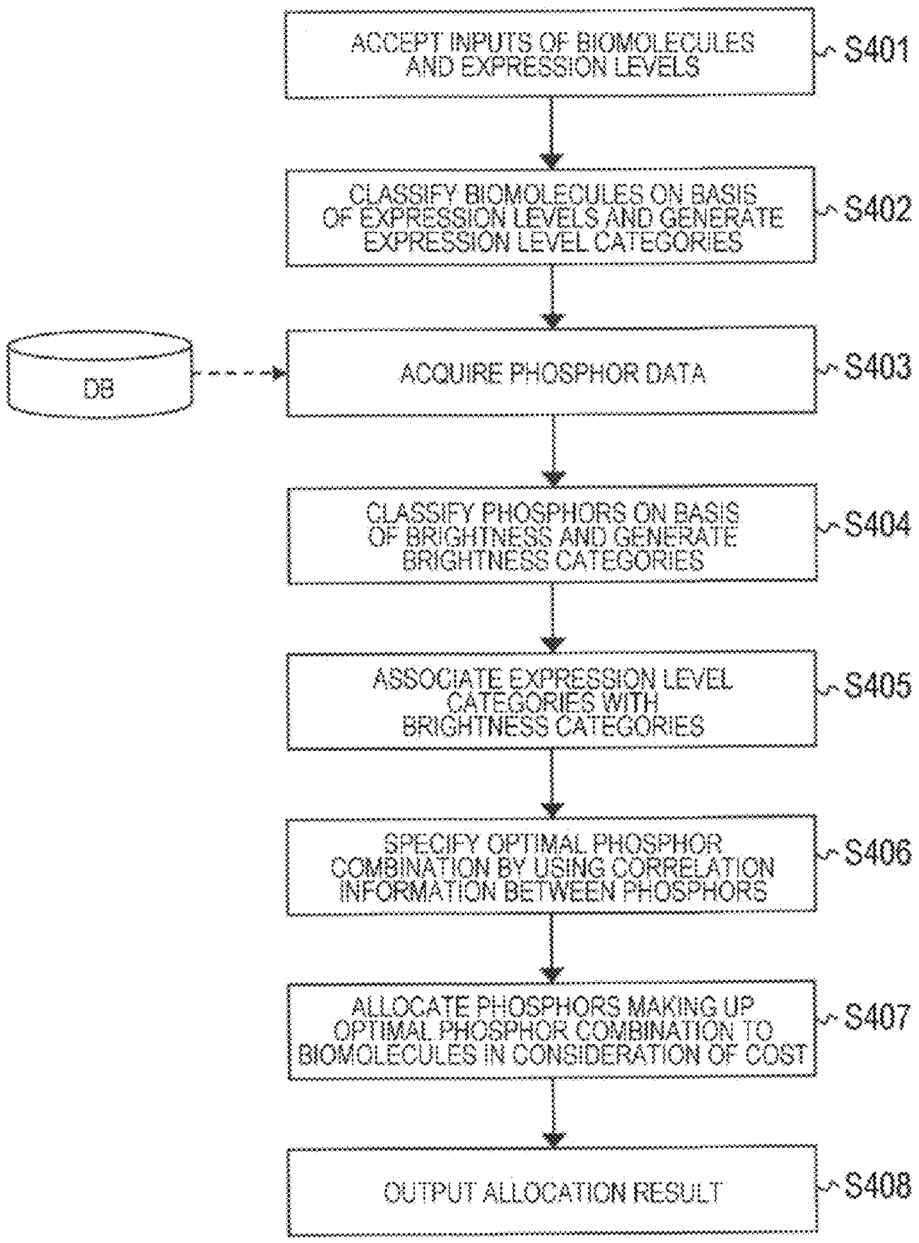
FIG. 18 is a flowchart of processing executed by the information processing apparatus according to the present technology.

FIG. 18 shows an example of a processing flow with reference to the cost information. In the processing flow shown in FIG. 18, steps S401 to S406 and S408 are the same as steps S101 to S106 and S108 described with reference to FIG. 4, and the description thereof also applies to steps S401 to S406 and S408.

In step S407, the processing unit 101 allocates the phosphors that make up the optimal phosphor combination identified in step S406 to the plurality of biomolecules on the basis of cost information regarding the complex of the biomolecule and the phosphor. In order to use the cost information, in step S407, the processing unit 101 may refer to, for example, a database outside the information processing apparatus 100. The database can have, for example, price data of a complex of a biomolecule and a phosphor (e.g., fluorochrome-labeled antibody) as the cost information. In step S407, in addition to the cost information, the expression level and the like described in step S107 above may be considered.

(3-9) Example of Processing by Processing Unit (Processing Flow in Case where Phosphor Determined in Advance to be Adopted is Included)

In a preferred embodiment of the present technology, in a case where a phosphor to be allocated to at least one biomolecule among the plurality of biomolecules is identified, the processing unit 101 generates the combination list further on the basis of correlation information between the plurality of phosphors and the phosphor identified in advance. The present embodiment can be applied to a case where there is a fluorochrome-labeled antibody that the user has already decided to use from a past experiment or a case where the user desires to add one or a plurality of antibodies to an already established panel (also referred to as "existing panel"), for example, at the time of performing an experiment using a flow cytometer or the like. In a case where some phosphors are identified in advance as described above, the phosphors are treated as fixed values in the processing according to the present technology.

Figure 19:
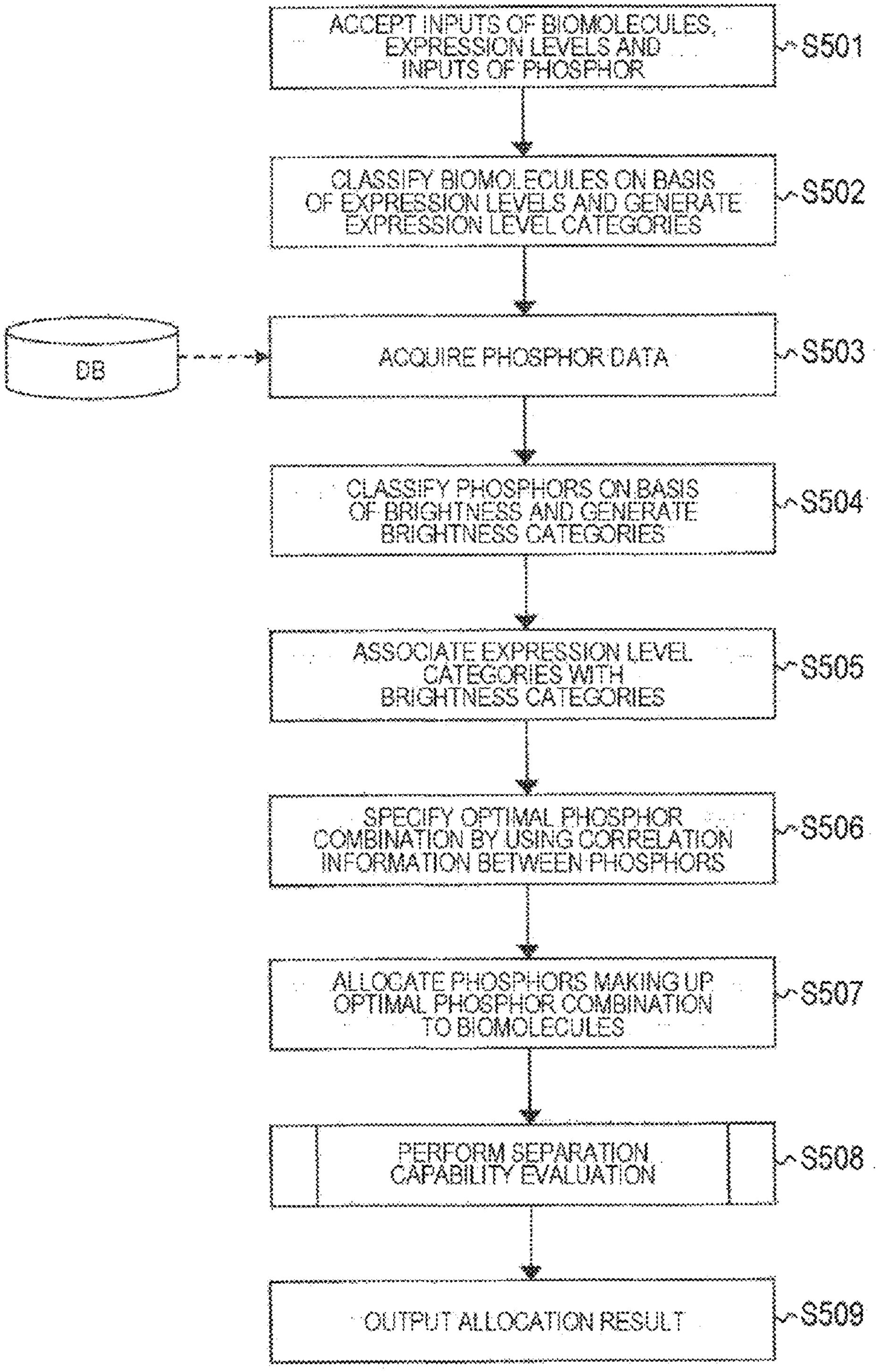
FIG. 19 is a flowchart of processing executed by the information processing apparatus according to the present technology.

Hereinafter, processing according to the present embodiment will be described with reference to FIG. 19. FIG. 19 is an example of a processing flow according to the present embodiment. In the processing flow shown in FIG. 19, steps S502 to S507 and S509 are similar to steps S102 to S107 and S109 described with reference to FIG. 4 except that the allocated phosphor is identified in advance for some of the biomolecules, and the description thereof is also applied to steps S102 to S107 and S109. Step S508 is similar to step S208 described with reference to FIG. 13, except that the allocated phosphor is identified in advance for some of the biomolecules, and the description thereof also applies to step S508.

In step S501 of FIG. 19, the information processing apparatus 100 accepts inputs of a plurality of biomolecules and the respective expression levels of the plurality of biomolecules. Furthermore, an input of an allocated phosphor is accepted for some of the plurality of biomolecules.

For example, in step S501, the processing unit 101 can cause the output unit 104 (particularly, a display device) to display an input acceptance window for accepting the input and urge the user to perform the input.

FIG. 20A shows an example of the input acceptance window. The window shown in FIG. 20A includes a column of a phosphor identifying list box a phosphor to be allocated to a biomolecule, in addition to a column of a list box for accepting inputs of a biomolecule and an expression level grade. By the user selecting one or a plurality of phosphors in the phosphor identifying list box to identify the phosphors the processing unit 101 accepts an input of the allocated phosphors. In FIG. 20A, "PE", "APC", "FITC", and "Alexa Fluor 700" have been identified as the phosphors allocated to the biomolecules "CD27", "CD5", "CD4", and "CD45", respectively.

In step S502, the processing unit 101 classifies the plurality of biomolecules selected in step S501 on the basis of the expression level selected for each biomolecule and generates one or a plurality of expression level categories, particularly a plurality of expression level categories. The biomolecule for which the phosphor was identified in step S501 may also be classified on the basis of the expression level in step S502.

The number of expression level categories may be, for example, a value corresponding to the number of expression level grades and may be preferably two to 20, preferably two to 15, even more preferably two to ten, and for example, three to ten.

In step S503, the processing unit 101 acquires a list related to phosphors capable of labeling the biomolecule input in step S501. Further, the processing unit 101 also acquires information regarding the phosphor input in step S501. The list of the phosphors may be acquired, for example, from a database existing outside the information processing apparatus 100 or may be acquired from a database stored inside the information processing apparatus 100 (e.g., storage unit 102).

In step S504, the processing unit 101 classifies the phosphors included in a list related to the phosphors capable of labeling the biomolecule out of the list related to the phosphors acquired in step S503 on the basis of the brightness of each phosphor, and generates one or a plurality of brightness categories, particularly a plurality of brightness categories.

In the list related to phosphors acquired in step S503, the phosphors input in step S501 are also classified on the basis of the brightness of each phosphor and put into any of the brightness categories.

In step S505, the processing unit 101 associates the expression level categories generated in step S502 with the brightness categories generated in step S504. Preferably, the processing unit 101 associates one expression level category with one brightness category. In addition, the processing unit 101 can perform association such that the expression level category and the brightness category correspond on a one-to-one basis. That is, the association can be performed such that two or more expression level categories are not associated with one brightness category.

In step S506, the processing unit 101 identifies the optimal phosphor combination by using correlation information between phosphors. The optimal phosphor combination may be, for example, a phosphor combination that is optimal from the viewpoint of the correlation between phosphor spectra, more particularly a phosphor combination that is optimal from the viewpoint of a correlation coefficient between phosphor spectra, and even more particularly a phosphor combination that is optimal from the viewpoint of the square of the correlation coefficient between phosphor spectra.

The correlation information between the phosphors may be preferably correlation information between phosphor spectra. That is, in one preferred embodiment of the present technology, the processing unit 101 identifies the optimal phosphor combination by using correlation information between phosphor spectra.

An example of how to identify the optimal phosphor combination will be described below.

The processing unit 101 selects, from a certain brightness category, the same number of phosphors as "the number of biomolecules belonging to the expression level category associated with the certain brightness category". However, in a case where the phosphor input in step S501 is included in the certain brightness category, the processing unit 101 selects the same number of phosphors as ("the number of biomolecules belonging to the expression level category associated with the certain brightness category"-"the phosphor input in step S501") from the certain brightness category.

The above phosphor selection is performed for all brightness categories. As a result, the sum of the "number of selected phosphors" and the "number of phosphors input in step S501" becomes the same number as the "number of a plurality of biomolecules to be used for analysis of a sample", and one phosphor combination candidate is thus obtained.

Next, the processing unit 101 calculates the square of a correlation coefficient between fluorescence spectra for any two combinations of phosphors included in the phosphor combination candidates. The processing unit 101 calculates the square of the correlation coefficient for all combinations. By the calculation processing, the processing unit 101 obtains a matrix of correlation coefficient square values as shown in FIG. 6, for example. Then, from the matrix of correlation coefficient square values, the processing unit 101 identifies the maximum correlation coefficient square value.

Here, in a case where the "number of phosphors belonging to a certain brightness category" is larger than the "number of biomolecules belonging to an expression level category associated with the certain brightness category", there is a plurality of combinations of phosphors selected from the certain brightness category. For example, there are six kinds of phosphor combinations ($={}_4C_2$) in a case where two phosphors are selected from four phosphors. Therefore, for example, in a case where there are three brightness categories, four phosphors belong to any of the three brightness categories, and two phosphors are selected from each brightness category, there are 216 phosphor combination candidates of 6×6×6. However, in a case where the phosphor input in step S501 is included in the certain brightness category, the number of phosphor combination candidates decreases.

In the present technology, the processing unit 101 identifies the maximum correlation coefficient square value as described above for every possible phosphor combination candidate. Then, the processing unit 101 identifies a phosphor combination candidate having the smallest identified maximum correlation coefficient square value. The processing unit 101 identifies the phosphor combination candidate identified in this manner as the optimal phosphor combination.

In step S507, the processing unit 101 allocates the phosphors that make up the optimal phosphor combination identified in step S506 to the plurality of biomolecules. More specifically, the processing unit 101 allocates each of the phosphors that make up the optimal phosphor combination to the biomolecules belonging to the expression level category associated with the brightness category to which the phosphor belongs.

In a case where two or more phosphors are included in one brightness category, two or more biomolecules can be included in the associated expression level category. In this case, a phosphor having a higher brightness can be allocated to a biomolecule having a lower expression level (or expected to have a lower expression level).

The processing unit 101 generates a combination of the phosphor and the biomolecule for each biomolecule by the allocation processing described above. In this manner, the processing unit 101 generates a combination list of phosphors with respect to biomolecules.

In step S508, the processing unit 101 evaluates the separation capability for the phosphor group that makes up the combination list generated by the allocation processing in step S507. A more detailed processing flow of step S508 is as described with reference to FIG. 14.

However, in step S303 of FIG. 14, the processing unit 101 does not identify the phosphor input in step S501 as a phosphor having poor separation performance. This makes it possible to prevent the phosphor input in step S501 from being changed.

In step S509, the processing unit 101 can cause, for example, the output unit 104 to output the combination list generated in step S508. For example, the combination list can be displayed on the display device.

For example, as shown in FIG. 20B, it is confirmed from the output result that phosphors have been identified for biomolecules marked with circles.

Further, in step S509, information regarding the complex of the phosphor and the biomolecule (e.g., information regarding the fluorescence-labeled antibody) can be displayed for the biomolecule to which the phosphor selected by optimization has been allocated. FIG. 20C shows an example of how to display such information. As shown in the drawing, the information includes the name of a biomolecule (the name of an antigen captured by an antibody, "Antibody" field), the name of a phosphor labeling the biomolecule ("Fluorochrome" field), the name of a clone ("Clone" field), an isotype ("ISO Type" field), a species from which the antigen captured by the biomolecule (antibody) is derived ("Target Species" field), a species from which the biomolecule (antibody) is derived ("Host Species" field), a catalog number ("Catalog" field), the size of a reagent ("Size" field), the name of a company manufacturing the complex (reagent) ("Company" field), a price ("Price" field), a web page related to the antibody ("URL" field), and the product name of the complex ("Product Name" field). In the present technology, the information regarding the complex may include one or a plurality of pieces of listed information and preferably includes the name of a biomolecule and the name of a phosphor labeling the biomolecule. In a preferred implementation, the information can further include a price.

(3-10) Example of Processing by Processing Unit (Processing Flow in Case where Light-Producing Substance, Determined in Advance to be Adopted, is Included)

In one embodiment of the present technology, in a case where a light-producing substance to be used for analysis of the sample is identified, the processing unit further generates the combination list on the basis of correlation information between the plurality of phosphors and the light-producing substance. For example, in order to perform an experiment on a fluorescence-labeled specimen by a flow cytometer or the like, the present embodiment can be applied in a case where, in addition to the determination of the amount of normal surface antibody or cytokine a light-producing substance except for these biomolecules is used for analysis. Examples of the light-producing substance include a fluorescent protein and a cell life/death determination reagent. For example, in the experiment, it is possible to determine fluorescence derived from a fluorescent protein contained in a cell itself and/or determine light caused by a reagent for performing life/death determination on the cell. Such a fluorescent protein and/or a life/death determination reagent can also be treated as a fixed value in the processing according to the present technology, similarly to the processing described in (3-9) above, and the dye can then be optimized for other biomolecules.

Figure 21:
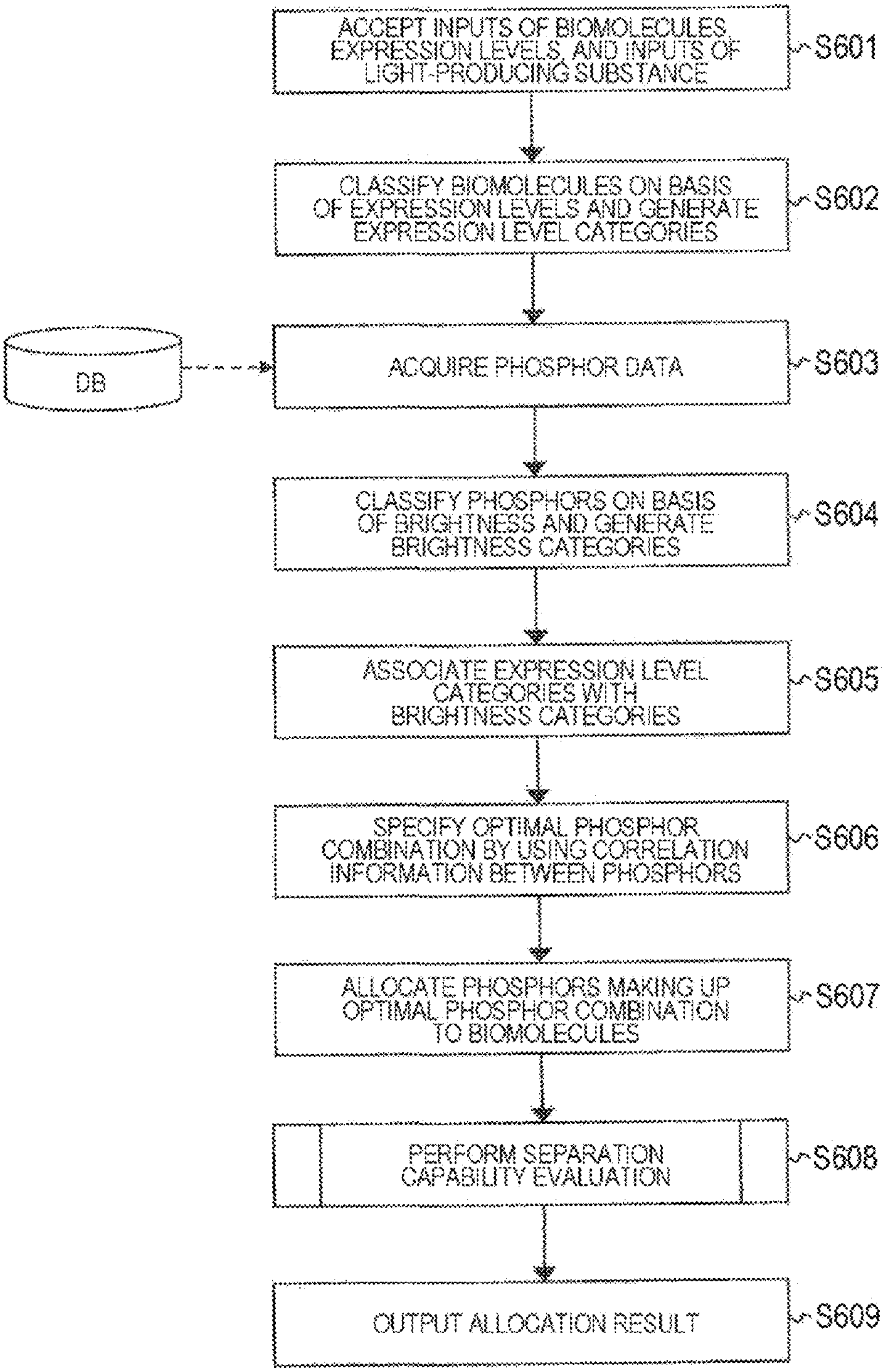
FIG. 21 is a flowchart of processing executed by the information processing apparatus according to the present technology.

Hereinafter, processing according to the present embodiment will be described with reference to FIG. 21. FIG. 21 is an example of a processing flow according to the present embodiment. In the processing flow shown in FIG. 21, steps S602 to S607 and S609 are similar to steps S102 to S107 and S109 described with reference to FIG. 4 except that the light-producing substance is identified in advance in addition to the biomolecule, and the description thereof is also applied to steps S102 to S107 and S109. Step S608 is similar to step S208 described with reference to FIG. 13 except that the light-producing substance is identified in advance in addition to the biomolecule, and the description thereof also applies to step S608.

In step S601 of FIG. 21, the information processing apparatus 100 accepts inputs of a plurality of biomolecules and the respective expression levels of the plurality of biomolecules. Furthermore, the information processing apparatus 100 also accepts an input of a light-producing substance except for the biomolecule to which allocation of the phosphor is required.

For example, in step S601, the processing unit 101 can cause the output unit 104 (particularly, a display device) to display an input acceptance window for accepting the input to urge the user to perform the input.

A of FIG. 22 shows an example of an input acceptance window for the light-producing substance. The window shown in A of FIG. 22 can accept inputs of a fluorescent protein and a cell life/death determination reagent. In A of FIG. 22, a fluorescent protein selection field 1 ("Fluorescent protein 1") in which "EGFP" has been selected has been checked, and "+" has been selected for the expression level. Similarly, a cell life/death determination reagent selection field ("Live/Death") in which "PI" has been selected has been checked, and "++" has been selected for the expression level. Note that the term "expression level" is not originally used for the cell life/death determination reagent, but the term "expression level" is used for convenience in order to treat the reagent equally to other substances. In response to the selections of the fluorescent protein and the cell life/death determination reagent and the expression levels thereof and the clicking of a close button ("Close"), the results of the selections are reflected in the input acceptance window for accepting the input of the biomolecule and the expression level grade described with respect to step S102 in (3-2) above and displayed as shown in B of FIG. 22. In a row indicated by "▲" in B of FIG. 22, the selection result in the input acceptance window for the light-producing substance is reflected. Since the input acceptance window for accepting the inputs of the biomolecule and the expression level grade is as described in (3-2) above, it is omitted.

In step S601, in response to the selection of the light-producing substance, the processing unit 101 can acquire information regarding the selected light-producing substance. As a result, as shown in FIG. 22A, the processing unit 101 may, for example, cause an optical spectrum of light generated from the light-producing substance to be displayed in the input acceptance window. The information regarding the light-producing substance can include, for example, brightness and spectrum of light generated from the light-producing substance, and the like.

Steps S602 and S603 may be executed similarly to steps S102 and S103 described in (3-2) above. Note that in step S603, the processing unit 101 may acquire, from the database, information regarding the light-producing substance in addition to the information regarding the phosphor. In this case, in step S601, the information regarding the light-producing substance may not be acquired.

In step S604, the processing unit 101 classifies the phosphors included in a list related to the phosphors capable of labeling the biomolecule out of the list related to the phosphors acquired in step S603 on the basis of the brightness of each phosphor, and generates one or a plurality of brightness categories, particularly a plurality of brightness categories.

In step S604, the processing unit 101 also classifies the light-producing substance selected in step S601 on the basis of the brightness of each light-producing substance and puts the light-producing substance into any of the brightness categories.

In step S605, the processing unit 101 associates the expression level category generated in step S602 with the brightness category generated in step S604. Preferably, the processing unit 101 associates one expression level category with one brightness category. In addition, the processing unit 101 can perform association such that the expression level category and the brightness category correspond on a one-to-one basis. That is, the processing unit 101 can perform the association such that two or more expression level categories are not associated with one brightness category.

In step S606, the processing unit 101 identifies the optimal phosphor combination by using the correlation information between the phosphor and the light-producing substance and/or the correlation information between the light-producing substances in addition to the correlation information between the phosphors. The optimal phosphor combination may be, for example, a phosphor combination that is optimal from the viewpoint of the correlation between the optical spectra of these substances, more particularly a phosphor combination that is optimal from the viewpoint of a correlation coefficient between the optical spectra of these substances, and even more particularly a phosphor combination that is optimal from the viewpoint of the square of the correlation coefficient between the optical spectra of these substances. Note that in the present embodiment, the "optical spectrum" includes a fluorescence spectrum of a phosphor and an optical spectrum of light generated from a light-producing substance.

The correlation information between these substances may be preferably correlation information between optical spectra. That is, in one preferred embodiment of the present technology, the processing unit 101 identifies the optimal phosphor combination by using correlation information between optical spectra.

How to identify the optimal phosphor combination is as described in (3-2) above, and the description also applies to the present embodiment.

Step S607 may be performed similarly to step S107. The processing unit 101 generates a combination of a phosphor and a biomolecule for each biomolecule by the allocation processing in step S607 and generates a combination list of phosphors for the biomolecule.

In step S608, the processing unit 101 evaluates the separation capability for the phosphor group that makes up the combination list generated by the allocation processing in step S607 and the group including the light-producing substances. A more detailed processing flow of step S608 is as described with reference to FIG. 14.

However, in step S303 of FIG. 14, the processing unit 101 does not identify the light-producing substance input in step S601 as a phosphor having poor separation performance. This makes it possible to prevent the light-producing substance input in step S601 from being changed.

In step S609, the processing unit 101 can cause, for example, the output unit 104 to output the combination list generated in step S608. For example, the combination list can be displayed on the display device.

For example, as shown in FIG. 21C, it is confirmed from the output result that phosphors have been identified for biomolecules marked with circles.

(3-11) Example of Processing by Processing Unit (Processing Flow in Case where Stain Index Between Phosphors or Spillover Spreading Matrix Between Phosphors is Used as Correlation Information)

In (3-2) above, in step S106, the correlation between phosphor spectra has been mentioned as an example of correlation information between phosphors, but in another embodiment of the present technology, correlation information between phosphors is not limited thereto. For example, as correlation information between phosphors, a stain index between phosphors or a spillover spreading matrix between phosphors may be used. Another embodiment here is as described in (3-2) above except that the correlation information to be used is different. For example, in the processing flow described in (3-2) above, step S106 is different, but the other steps are the same. Thus, step S106 will be described below.

(3-11-1) Case of Using Stain Index Between Phosphors

In this case, a normalized inter-phosphor stain index list may be prepared in advance in order to execute the processing in step S106. In the present specification, the normalized inter-phosphor stain index is also referred to as "normalized inter-phosphor SI".

The normalized inter-phosphor SI list may be a list having inter-phosphor stain indexes for all combinations of two phosphors in the phosphor group including at least all the phosphors included in the list related to the phosphors acquired in step S103. For example, the normalized inter-phosphor stain index list may be a list having inter-phosphor stain indexes for all combinations of two phosphors in a phosphor group including all phosphors usable in a device using a combination list of phosphors with respect to biomolecules generated by the processing unit 101.

FIG. 23A shows an example of a normalized inter-phosphor SI list. As shown in FIG. 23A, the row header of the list indicates a positive phosphor, and the column header of the list indicates a negative phosphor. For example, all the phosphors usable in the device are listed in both the row headers and column headers. Note that in FIG. 23A, "• • •" means omission of a part of the table.

Figure 23B:
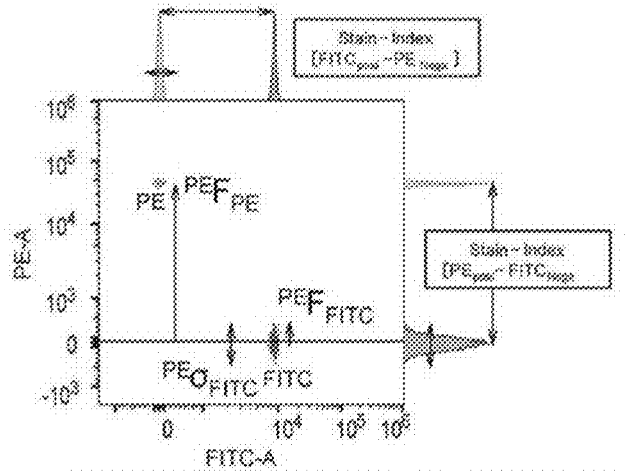
FIG. 23B is a diagram for explaining a method for calculating normalized inter-phosphor SI.

A method for calculating the normalized inter-phosphor SI will be described with reference to FIG. 23B. First, simulation data is generated for all phosphors appearing in the normalized inter-phosphor SI list on the condition that the amount of fluorescence of each phosphor is the same. Then, a normalized inter-phosphor SI between two different phosphors is calculated using the simulation data. FIG. 23B shows an example of calculation of a normalized inter-phosphor SI for PE with respect to FITC. The normalized inter-phosphor SI means the separation performance for FITC in a case where PE is positive.

The circled number 1 in FIG. 23B indicates an equation for calculating a normalized inter-phosphor SI (${}^{PE}SI_{FITC}$) in the PE-positive and FITC-negative case. As shown in the equation, ${}^{PE}SI_{FITC}$ is represented by $\{{}^{PE}F_{PE}-{}^{PE}F_{FITC}\}\div\{{}^{PE}\sigma_{FITC}\times 2\}$. Each of the terms in this equation is as shown on the left of FIG. 23B and means the following.

${}^{PE}F_{PE}$ is the mean fluorescence intensity of PE-positive and FITC-negative particles at the fluorescence wavelength of PE.

${}^{PE}F_{FITC}$ is the mean fluorescence intensity of PE-negative and FITC-positive particles at the fluorescence wavelength of PE.

${}^{PE}\sigma_{FITC}$ is the standard deviation of the mean fluorescence intensity at the fluorescence wavelength of PE for PE-negative and FITC-positive particles.

The above calculation is performed for all the combinations of the two phosphors, and the normalized inter-phosphor SI list as shown in FIG. 23A is generated.

In step S106, the processing unit 101 identifies the optimal phosphor combination by using the normalized inter-phosphor SI list prepared as described above as the correlation information between the phosphors. An example of how to identify the optimal phosphor combination will be described below.

The processing unit 101 selects, from a certain brightness category, the same number of phosphors as "the number of biomolecules belonging to the expression level category associated with the certain brightness category". The phosphors are selected for all brightness categories. Thereby, the same number of phosphors as the "number of a plurality of biomolecules to be used for analysis of a sample" are selected, and in this manner, one phosphor combination candidate is obtained.

Next, for a combination of any two phosphors included in the phosphor combination candidates, the processing unit 101 refers to the normalized inter-phosphor SI list and identifies a normalized inter-phosphor SI corresponding to the combination of the two phosphors. Here, for each combination, the normalized inter-phosphor SI in a case where one is positive and the other is negative and the normalized inter-phosphor SI in a case where the one is negative and the other is positive are identified. The processing unit 101 identifies such two normalized inter-phosphor SI for all combinations of two phosphors included in the phosphor combination candidates. Then, the processing unit 101 identifies a minimum value among all the normalized inter-phosphor SIs identified for the phosphor combination candidates.

Note that the larger the normalized inter-phosphor SI, the better the separation performance is. Therefore, it is considered that the larger the minimum value identified as described above, the better the separation performance of the phosphor combination candidate from which the minimum value is obtained.

Here, as described in (3-2) above, in a case where the "number of phosphors belonging to a certain brightness category" is larger than the "number of biomolecules belonging to an expression level category associated with the certain brightness category", there is a plurality of combinations of phosphors selected from the certain brightness category. Therefore, in the present technology, the processing unit 101 identifies the minimum value of the normalized inter-phosphor SIs as described above for all possible phosphor combination candidates. Then, the processing unit 101 identifies a phosphor combination candidate having the largest identified minimum value. The processing unit 101 identifies the phosphor combination candidate identified in this manner as the optimal phosphor combination.

Example 5: Evaluation Using Simulation Data—Case of Normalized Inter-Phosphor SI A combination list of biomolecules and phosphors was generated by allocating 20 phosphors to 20 biomolecules in a similar manner to in Example 1 except that the normalized inter-phosphor SI was used instead of the square value of the correlation coefficient as the correlation information. The fluorescence separation performance by the combination list was confirmed using simulation data. The fluorescence separation performance was evaluated using the inter-phosphor stain index. A list of inter-phosphor stain indexes is shown above in FIG. 30A. In addition, two-dimensional plots obtained in the case of using the combination list are also shown below FIG. 30A.

Further, 20 phosphors were manually allocated to the 20 biomolecules, and a combination list of biomolecules and phosphors was generated. The fluorescence separation performance by the combination list was confirmed using the simulation data in a similar manner to the above. The fluorescence separation performance was evaluated using the inter-phosphor stain index. A list of inter-phosphor stain indexes is shown above in FIG. 30B. In addition, two-dimensional plots obtained in the case of using the combination list are also shown below FIG. 30B.

Figure 30A:
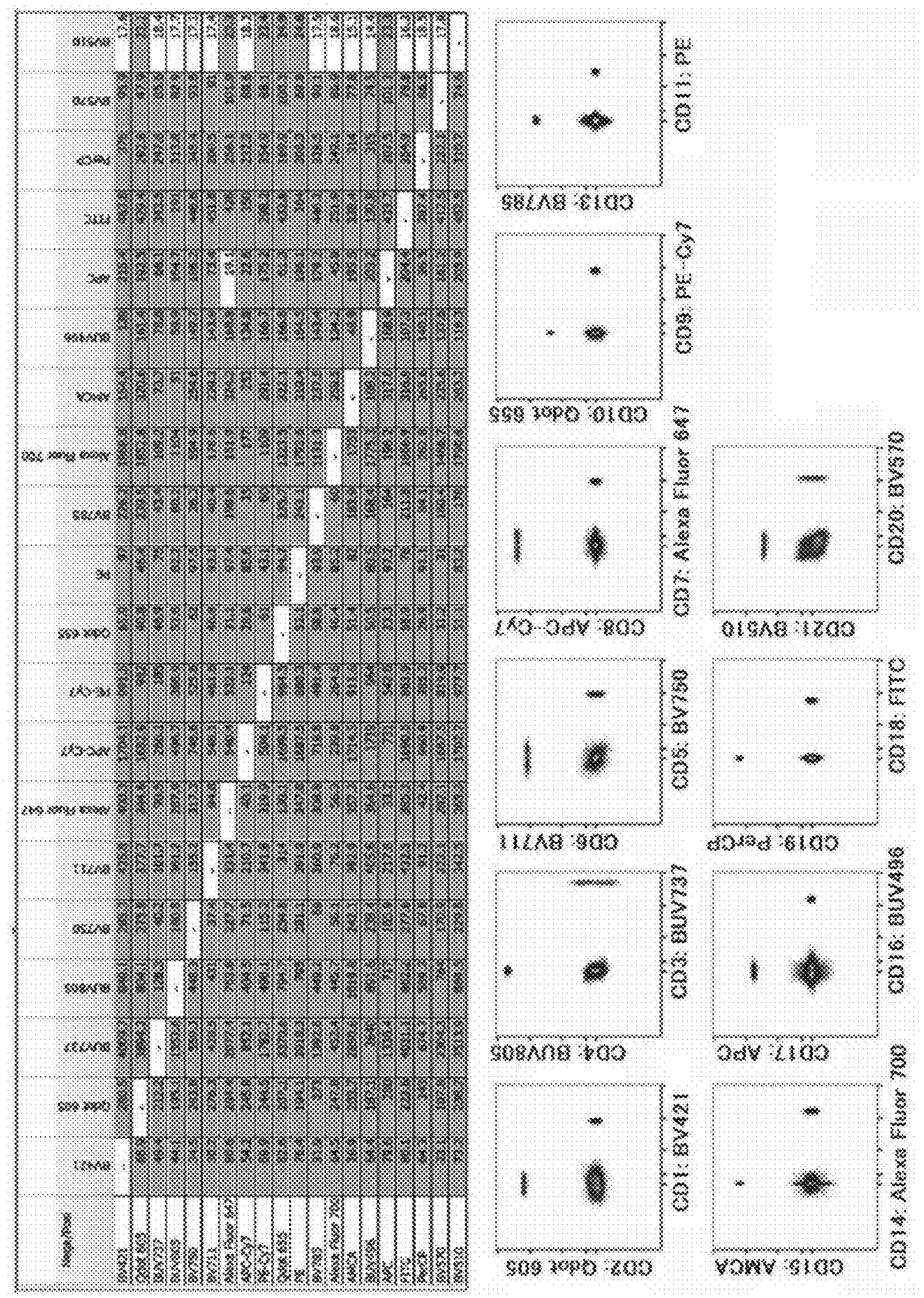
FIG. 30A is a diagram showing inter-phosphor stain indexes and two-dimensional plots obtained by an experiment.
Figure 30B:
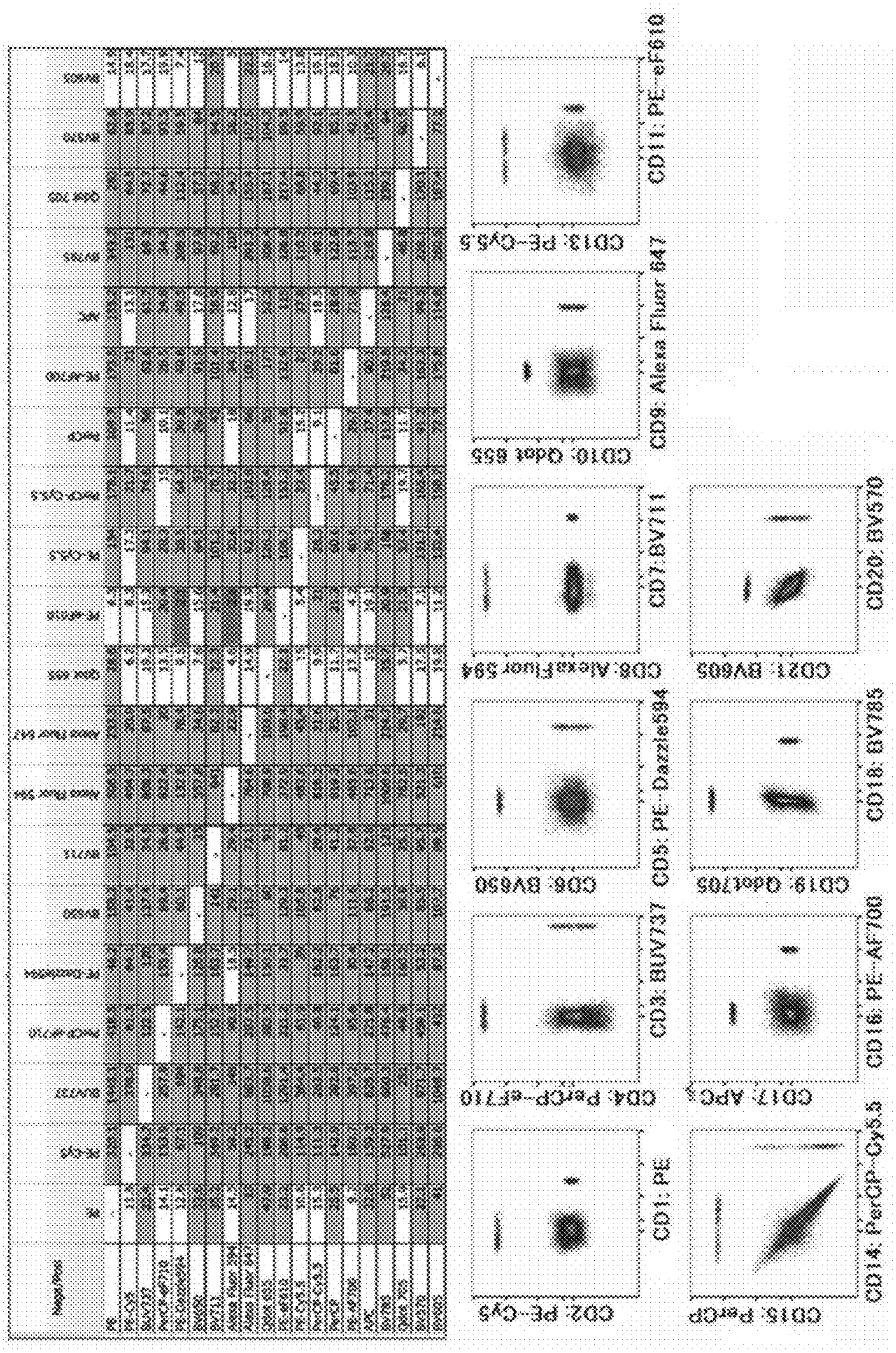
FIG. 30B is a diagram showing inter-phosphor stain indexes and two-dimensional plots obtained by an experiment.

For the combination list generated by manual allocation, the inter-phosphor stain indexes were calculated, and the minimum value among the calculated inter-phosphor stain indexes was 2.14 (above in FIG. 30B). On the other hand, for the combination list generated according to the present technology, the inter-phosphor stain indexes were calculated, and the minimum value among the calculated inter-phosphor stain indexes was 14.41 (above in FIG. 30A). Therefore, it can be seen that the separation performance can be improved by the information processing apparatus according to the present technology.

In addition, the minimum value of the normalized inter-phosphor SIs was 7.8 for the combination list generated by manual allocation, whereas the minimum value of the normalized inter-phosphor SIs was 23.2 for the combination list generated according to the present technology. From this point as well, it can be seen that the separation performance can be improved by the information processing apparatus according to the present technology.

The improved separation performance can also be confirmed by comparing the two-dimensional plots shown below in FIG. 30A and below in FIG. 30B.

(3-11-2) Case of Using Spillover Spreading Matrix Between Phosphors

In this case, an inter-phosphor spillover spreading matrix may be prepared in advance in order to execute the processing in step S106. In the present specification, the inter-phosphor spillover spreading matrix is also referred to as "inter-phosphor SSM". Further, inter-phosphor spillover spreading is also referred to as "inter-phosphor SS".

The inter-phosphor SSM may be an inter-phosphor SSM for all combinations of two phosphors in the phosphor group including at least all the phosphors included in the list related to the phosphors acquired in step S103. For example, the inter-phosphor SSM may be an inter-phosphor SSM for all combinations of two phosphors in a phosphor group including all phosphors usable in a device using a combination list of phosphors with respect to biomolecules generated by the processing unit 101.

FIG. 24A shows an example of the inter-phosphor SSM. As shown in FIG. 24A, the row header (Filter) of the matrix indicates a detector in a wavelength band corresponding to each phosphor, and the column header (Sample) indicates a particle labeled with the phosphor. Each inter-phosphor SS is an index related to the degree of leakage of light generated from the phosphor shown in Sample to the detector corresponding to the phosphor shown in Filter. Note that in FIG. 24A, "• • •" means omission of a part of the table.

Figure 24B:
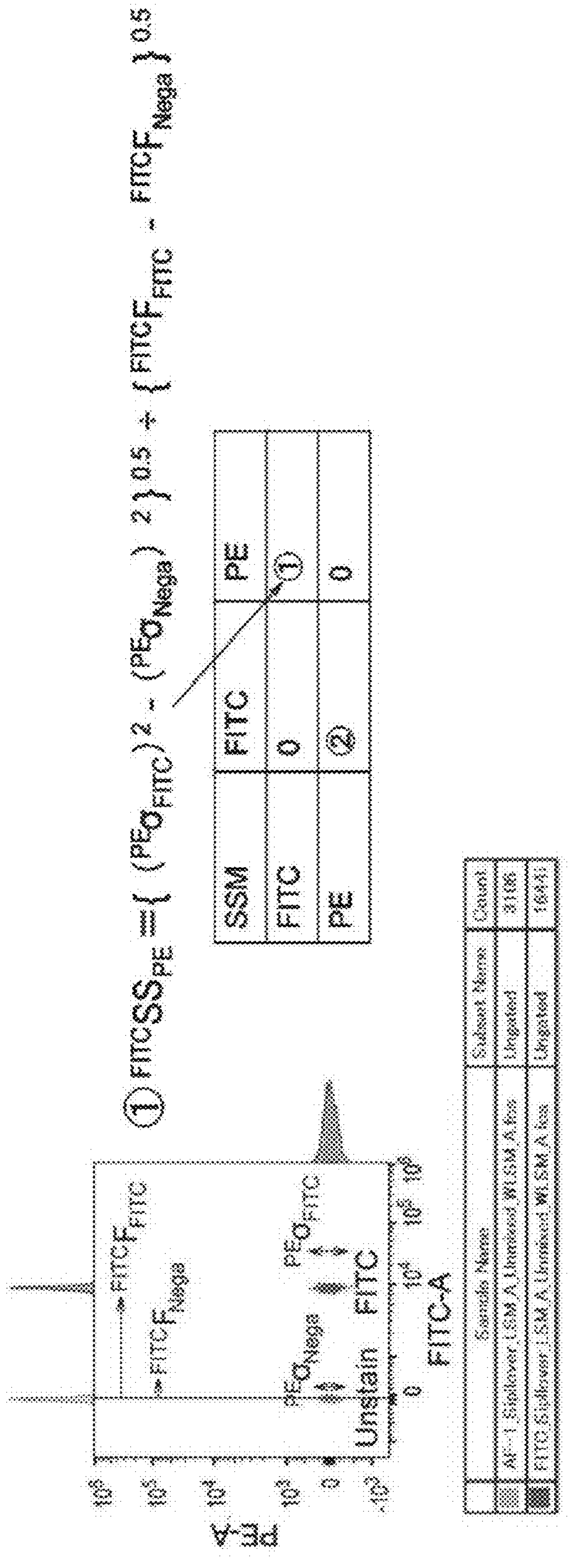
FIG. 24B is a diagram for explaining a method for calculating an inter-phosphor SSM.

A method for calculating the inter-phosphor SS will be described with reference to FIG. 24B. First, simulation data is generated for all phosphors appearing in the normalized inter-phosphor SI list on the condition that the amount of fluorescence of each phosphor is the same. Then, an inter-phosphor SS between two different phosphors is calculated using the simulation data. Note that data actually measured for the fluorescence-labeled particles may be used instead of the simulation data. FIG. 24B shows an example of calculation of an inter-phosphor SS of FITC with respect to PE. The inter-phosphor SS means the degree of leakage of fluorescence of light generated from FITC to a detector corresponding to PE.

The circled number 1 in FIG. 24B indicates an equation for calculating an inter-phosphor SS ($^{FITC}SS_{PE}$ of FITC with respect to PE). As shown in the equation, $^{FITC}SS_{PE}$ is represented by $\{(^{PE}\sigma_{FITC})^2-(^{PE}\sigma_{Nega})_2\}^{0.5} \div \{^{FITC}F_{FITC}-^{FITC}F_{Nega}\}^{0.5}$. Each of the terms in this equation is as shown on the left of FIG. 24B and means the following.

$^{PE}\sigma_{FITC}$ is the standard deviation of the mean fluorescence intensity at the fluorescence wavelength of PE for PE-negative and FITC-positive particles.

$^{PE}\sigma_{Nega}$ is the standard deviation of the mean fluorescence intensity at the fluorescence wavelength of PE for PE-negative and FITC-positive particles.

$^{FITC}F_{FITC}$ is the mean fluorescence intensity of PE-negative and FITC-positive particles at the fluorescence wavelength of FITC.

$^{FITC}F_{Nega}$ is the mean fluorescence intensity of PE-negative and FITC-negative particles at the fluorescence wavelength of FITC.

The above calculation is performed for all the combinations of the two phosphors, and the inter-phosphor SSM as shown in FIG. 24A is generated.

In step S106, the processing unit 101 identifies the optimal phosphor combination by using the inter-phosphor SSM prepared as described above as the correlation information between the phosphors. An example of how to identify the optimal phosphor combination will be described below.

The processing unit 101 selects, from a certain brightness category, the same number of phosphors as "the number of biomolecules belonging to the expression level category associated with the certain brightness category". The phosphors are selected for all brightness categories. Thereby, the same number of phosphors as the "number of a plurality of biomolecules to be used for analysis of a sample" are selected, and in this manner, one phosphor combination candidate is obtained.

Next, for a combination of any two phosphors included in the phosphor combination candidates, the processing unit 101 refers to the inter-phosphor SSM and identifies an inter-phosphor SS corresponding to the combination of the two phosphors. Here, for each combination, the inter-phosphor SS in a case where one is positive and the other is negative, and the inter-phosphor SS in a case where one is negative and the other is positive are identified. The processing unit 101 identifies such an inter-phosphor SS for all combinations of two phosphors included in the phosphor combination candidates. Then, the processing unit 101 identifies the maximum value among all the inter-phosphor SSs identified for the phosphor combination candidates.

Note that the smaller the inter-phosphor SS, the better the separation performance. Therefore, it is considered that the smaller the maximum value identified as described above, the better the separation performance of the phosphor combination candidate from which the maximum value is obtained.

Here, as described in (3-2) above, in a case where the "number of phosphors belonging to a certain brightness category" is larger than the "number of biomolecules belonging to an expression level category associated with the certain brightness category", there is a plurality of combinations of phosphors selected from the certain brightness category. Therefore, in the present technology, the processing unit 101 identifies the maximum value of the inter-phosphor SS as described above for all possible phosphor combination candidates. Then, the processing unit 101 identifies a phosphor combination candidate having the smallest identified maximum value. The processing unit 101 identifies the phosphor combination candidate identified in this manner as the optimal phosphor combination.

Example 6: Evaluation Using Simulation Data—Case of Inter-Phosphor SSM

A combination list of biomolecules and phosphors was generated by allocating 20 phosphors to 20 biomolecules in a similar manner to in Example 1 except that the inter-phosphor SSM was used instead of the square value of the correlation coefficient as the correlation information. The fluorescence separation performance by the combination list was confirmed using simulation data. The fluorescence separation performance was evaluated using the inter-phosphor stain index. A list of inter-phosphor stain indexes is shown above in FIG. 31A. In addition, two-dimensional plots obtained in the case of using the combination list are also shown below FIG. 31A.

Further, 20 phosphors were manually allocated to the 20 biomolecules, and a combination list of biomolecules and phosphors was generated. The fluorescence separation performance by the combination list was confirmed using the simulation data in a similar manner to the above. The fluorescence separation performance was evaluated using the inter-phosphor stain index. A list of inter-phosphor stain indexes is shown above in FIG. 31B. In addition, two-dimensional plots obtained in the case of using the combination list are also shown below FIG. 31B.

Figure 31A:
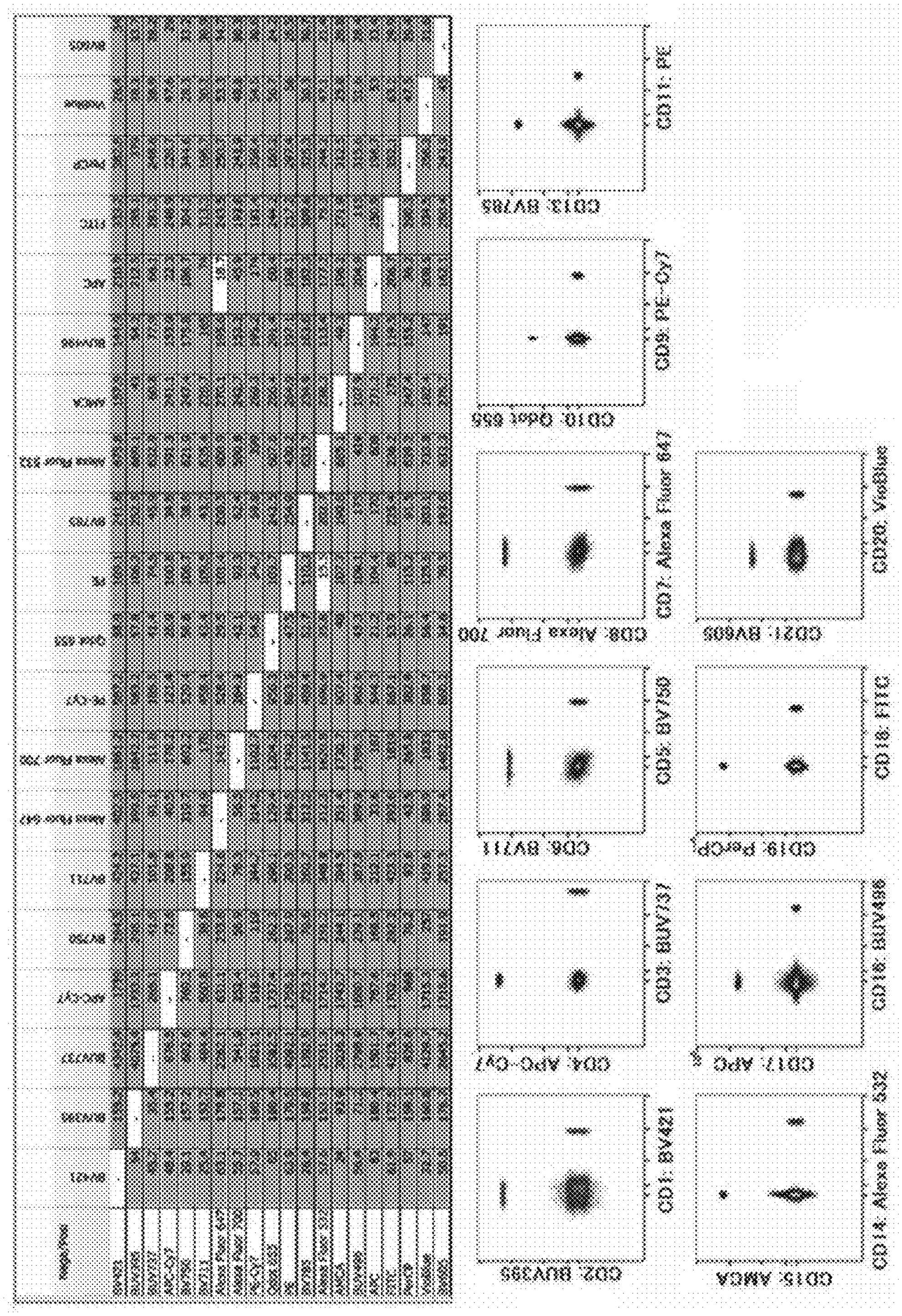
FIG. 31A is a diagram showing inter-phosphor stain indexes and two-dimensional plots obtained by an experiment.
Figure 31B:
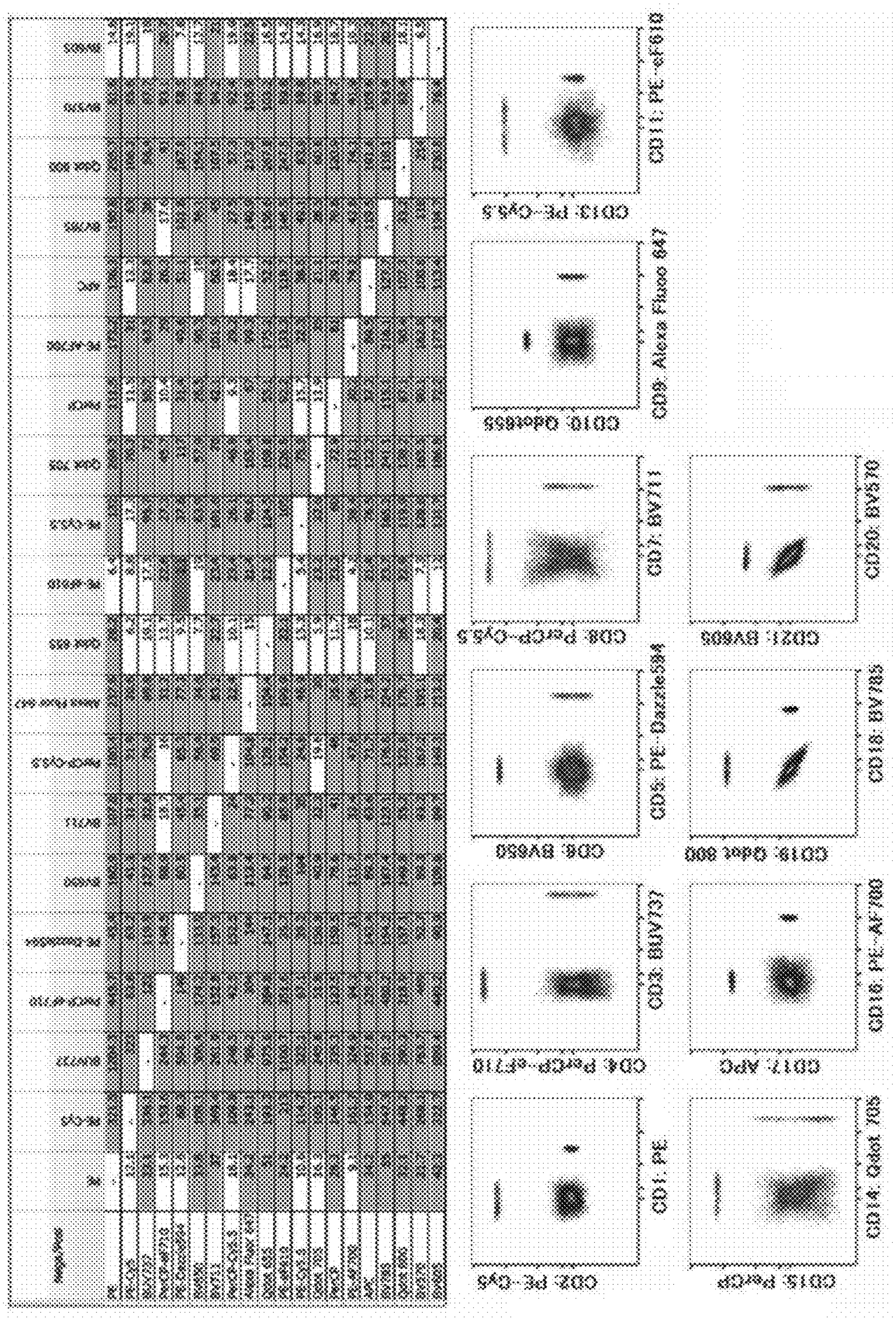
FIG. 31B is a diagram showing inter-phosphor stain indexes and two-dimensional plots obtained by an experiment.

For the combination list generated by manual allocation, the inter-phosphor stain indexes were calculated, and the minimum value among the calculated inter-phosphor stain indexes was 4.77 (above in FIG. 31B). On the other hand, for the combination list generated according to the present technology, the inter-phosphor stain indexes were calculated, and the minimum value among the calculated inter-phosphor stain indexes was 19.8 (above in FIG. 31A). Therefore, it can be seen that the separation performance can be improved by the information processing apparatus according to the present technology.

In addition, the minimum value of SS in the inter-phosphor SSM is 9.38 for the combination list generated by manual allocation, whereas the minimum value of SS in the inter-phosphor SSM is 4.43 for the combination list generated according to the present technology. From this point as well, it can be seen that the separation performance can be improved by the information processing apparatus according to the present technology.

The improved separation performance can also be confirmed by comparing the two-dimensional plots shown below in FIG. 31A and below in FIG. 31B.

2. Second Embodiment (Information Processing System)

The present technology also provides an information processing system including the processing unit described in "1. First Embodiment (information processing apparatus)" above. In addition to the processing unit, the information processing system can include the storage unit, the input unit, the output unit, and the communication unit described in "1. First Embodiment (information processing apparatus)" above. These components may be provided in one apparatus or may be provided in a plurality of apparatuses in a distributed manner. For example, the information processing system of the present technology can include an input unit that accepts an input of data regarding expression levels of a plurality of biomolecules to be used for analysis of a sample, in addition to the processing unit.

Also, by the information processing system according to the present technology, as described in "1. First Embodiment (information processing apparatus)" above, a more appropriate combination list can be generated, and processing for the generation is performed more efficiently. This makes it possible to automatically perform the optimized panel design.

3. Third Embodiment (Information Processing Method)

The present technology also relates to an information processing method. The information processing method includes a list generation step of generating a combination list of phosphors with respect to biomolecules on the basis of expression level categories obtained by classifying a plurality of biomolecules to be used for analysis of a sample on the basis of an expression level in the sample, brightness categories in which a plurality of phosphors usable for the analysis of the sample is classified on the basis of brightness, and correlation information between the plurality of phosphors. In the list generation step, the phosphor to be allocated to the biomolecule in the combination list is selected from phosphors belonging to the brightness categories associated with the expression level categories to which the biomolecules belong.

By generating a combination list of phosphors with respect to biomolecules in accordance with the information processing method of the present technology, a more appropriate combination list can be generated, and processing for the generation is performed more efficiently. This makes it possible to automatically perform the optimized panel design.

The list generation step included in the information processing method of the present technology may be executed according to any of the flows described in "1. First Embodiment (information processing apparatus)" above.

The list generation step can include, for example, an expression level category generation step of generating expression level categories obtained by classifying a plurality of biomolecules to be used for analysis of a sample on the basis of an expression level in the sample, a brightness category brightness category generation step in which a plurality of phosphors usable for the analysis of the sample is classified on the basis of brightness, and an allocation step of performing processing of allocating a phosphor to a biomolecule on the basis of the expression level categories, the brightness categories, and correlation information between the plurality of phosphors.

The expression level category generation step can include, for example, a step of executing step S102 described in "1. First Embodiment (information processing apparatus)" above. The expression level category generation step can also include a step of executing step S101 in addition to the step of executing step S102. These steps are as described in "1. First Embodiment (information processing apparatus)" above, and the description thereof also applies to the present embodiment.

The brightness category generation step can include, for example, a step of executing step S104 described in "1. First Embodiment (information processing apparatus)" above. The expression level category generation step can also include a step of executing step S103 in addition to the step of executing step S104. These steps are as described in "1. First Embodiment (information processing apparatus)" above, and the description thereof also applies to the present embodiment.

The allocation step can include, for example, a step of executing step S107 described in "1. First Embodiment (information processing apparatus)" above. The allocation step can include a step of executing step S105 and/or a step of executing step S106 in addition to the step of executing step S107. These steps are as described in "1. First Embodiment (information processing apparatus)" above, and the description thereof also applies to the present embodiment.

The information processing method according to the present technology may further include a separation capability evaluation step of performing separation capability evaluation for the combination list generated in the allocation step. The separation capability evaluation step may be performed as described in "(3-7) Example of processing by processing unit (example of executing separation capability evaluation)" of 1. above.

Further, the correlation information between the phosphors used in the information processing method according to the present technology may be correlation information between fluorescence spectra. Alternatively, the correlation information between the phosphors may be the normalized inter-phosphor SI or the inter-phosphor SSM. For details of these pieces of correlation information, see "1. First Embodiment (information processing apparatus)" above.

4. Fourth Embodiment (Program)

The present technology also provides a program for causing the information processing apparatus to execute the information processing method described in 3. above. The information processing method is as described in 1. and 3. above, and the description also applies to the present embodiment. The program according to the present technology may be recorded in, for example, the recording medium described above or may be stored in the information processing apparatus described above or the storage unit included in the information processing apparatus described above.

Note that the present technology can also have configurations as follows.

[1] An information processing apparatus including a processing unit that generates a combination list of phosphors with respect to biomolecules on the basis of expression level categories in which a plurality of biomolecules to be used for analysis of a sample is classified on the basis of expression levels in the sample, brightness categories in which a plurality of phosphors usable for the analysis of the sample is classified on the basis of brightness, and correlation information between the plurality of phosphors, in which the processing unit selects the phosphors to be allocated to the biomolecules in the combination list from phosphors belonging to a brightness category associated with an expression level category to which the biomolecules belong.

[2] The information processing apparatus according to [1], in which the expression level categories are associated with the brightness categories such that an expression level category obtained by classifying a biomolecule exhibiting a lower expression level corresponds to a brightness category in which a brighter phosphor is classified.

[3] The information processing apparatus according to [1] or [2], in which the processing unit selects each of the phosphors by using the correlation information.

[4] The information processing apparatus according to any one of [1] to [3], in which the correlation information is a correlation coefficient between fluorescence spectra of the plurality of phosphors.

[5] The information processing apparatus according to any one of [1] to [4], in which the correlation information is a value obtained by squaring a correlation coefficient between fluorescence spectra of the plurality of phosphors.

[6] The information processing apparatus according [4] or [5], in which the processing unit calculates the correlation coefficient by using two or more fluorescence spectra respectively obtained in a case where a phosphor is irradiated with excitation light beams having two or more different wavelengths.

[7] The information processing apparatus according to any one of [1] to [3], in which the correlation information is a stain index between the plurality of phosphors.

[8] The information processing apparatus according to any one of [1] to [3], in which the correlation information is a spillover spreading matrix between the plurality of phosphors.

[9] The information processing apparatus according to any one of [1] to [8], in which the plurality of phosphors is identified on the basis of data regarding whether a complex of a phosphor and a biomolecule is available.

[10] The information processing apparatus according to any one of [1] to [9], in which the processing unit adjusts the number of phosphors belonging to each of the brightness categories in accordance with the number of biomolecules belonging to each of the expression level categories.

[11] The information processing apparatus according to any one of [1] to [10], in which the plurality of phosphors is identified on the basis of information regarding priority associated with the phosphors.

[12] The information processing apparatus according to any one of [1] to [11], in which the processing unit performs evaluation of separation capability related to the combination list.

[13] The information processing apparatus according to [12], in which the processing unit further generates a modified combination list in which at least one phosphor of a set of phosphors included in the combination list is changed to another phosphor in accordance with a result of the evaluation of the separation capability and further performs separation capability evaluation related to the modified combination list.

[14] The information processing apparatus according to any one of [1] to [13], in which the processing unit further generates the combination list on the basis of cost information regarding a complex of a biomolecule and a phosphor.

[15] The information processing apparatus according to any one of [1] to [14], in which in a case where a phosphor to be allocated to at least one biomolecule among the plurality of biomolecules is identified, the processing unit further generates the combination list on the basis of correlation information between the plurality of phosphors and the phosphor identified in advance.

[16] The information processing apparatus according to any one of [1] to [15], in which in a case where a light-producing substance to be used for analysis of the sample is identified, the processing unit further generates the combination list on the basis of correlation information between the plurality of phosphors and the light-producing substance.

[17] The information processing apparatus according to any one of [1] to [16], in which each of the plurality of biomolecules is an antigen or an antibody.

[18] The information processing apparatus according to any one of [1] to [17], in which in a case where each of the plurality of biomolecules is an antigen, the expression level is an expression level of the antigen, and in a case where each of the plurality of biomolecules is an antibody, the expression level is an expression level of an antigen captured by the antibody.

[19] An information processing system including:

an input unit that accepts an input of data regarding expression levels of a plurality of biomolecules to be used for analysis of a sample; and a processing unit that generates a combination list of phosphors with respect to biomolecules on the basis of expression level categories in which the plurality of biomolecules is classified on the basis of expression levels in the sample, brightness categories in which a plurality of phosphors usable for the analysis of the sample is classified on the basis of brightness, and correlation information between the plurality of phosphors, in which the processing unit selects the phosphors to be allocated to the biomolecules in the combination list from phosphors belonging to a brightness category associated with an expression level category to which the biomolecules belong.

[20] An information processing method including a list generation step of generating a combination list of phosphors with respect to biomolecules on the basis of expression level categories in which a plurality of biomolecules to be used for analysis of a sample is classified on the basis of expression levels in the sample, brightness categories in which a plurality of phosphors usable for the analysis of the sample is classified on the basis of brightness, and correlation information between the plurality of phosphors, in which in the list generation step, the phosphors to be allocated to the biomolecules in the combination list are selected from phosphors belonging to a brightness category associated with an expression level category to which the biomolecules belong.

[21] A program causing an information processing apparatus to execute a list generation step of generating a combination list of phosphors with respect to biomolecules on the basis of expression level categories in which a plurality of biomolecules to be used for analysis of a sample is classified on the basis of expression levels in the sample, brightness categories in which a plurality of phosphors usable for the analysis of the sample is classified on the basis of brightness, and correlation information between the plurality of phosphors, in which in the list generation step, the phosphors to be allocated to the biomolecules in the combination list are selected from phosphors belonging to a brightness category associated with an expression level category to which the biomolecules belong.

REFERENCE SIGNS LIST

100 Information processing apparatus
101 Processing unit
102 Storage unit
103 Input unit
104 Output unit
105 Communication unit

The invention claimed is:

1. An information processing apparatus comprising:

at least one processor that:

receives, from an input unit, an indication of a plurality of biomolecules to be used for analysis of a sample and respective expression levels of the plurality of biomolecules;

obtains, from a database and/or from the input unit, an indication of a plurality of phosphors usable for analysis of the sample by a spectral flow cytometer and fluorescence spectra associated with the plurality of phosphors;

generates expression level categories for the plurality of biomolecules based on expression levels in the sample;

generates, based on the expression level categories, brightness categories for the plurality of phosphors based on brightness of the plurality of phosphors;

associates the expression level categories with the brightness categories based on the expression levels and the brightness;

generates, based on correlation information between the plurality of phosphors indicative of the fluorescence spectra associated with the plurality of phosphors, a combination list of phosphors to be used for the analysis of the sample by the spectral flow cytometer;

allocates, based on the association between the expression level categories and the brightness categories, phosphors of the combination list to biomolecules of the plurality of biomolecules;

outputs, for display by a display device, an indication of the phosphors of the combination list respectively allocated to the biomolecules of the plurality of biomolecules;

receives, from the spectral flow cytometer, light intensity data of the plurality of biomolecules stained with the phosphors of the combination list which were respectively allocated; and deconvolutes the light intensity data based on the fluorescence spectra of the phosphors of the combination list.

2. The information processing apparatus according to claim 1, wherein the expression level categories are associated with the brightness categories such that an expression level category obtained by classifying a biomolecule exhibiting a lower expression level corresponds to a brightness category in which a brighter phosphor is classified.

3. The information processing apparatus according to claim 1, wherein the at least one processor selects each of the phosphors by using the correlation information.

4. The information processing apparatus according to claim 1, wherein the correlation information is a correlation coefficient between fluorescence spectra of the plurality of phosphors.

5. The information processing apparatus according to claim 1, wherein the correlation information is a value obtained by squaring a correlation coefficient between fluorescence spectra of the plurality of phosphors.

6. The information processing apparatus according to claim 4, wherein the at least one processor calculates the correlation coefficient by using two or more fluorescence spectra respectively obtained in a case where a phosphor is irradiated with rays of excitation light beams having two or more different wavelengths.

7. The information processing apparatus according to claim 1, wherein the correlation information is a stain index between the plurality of phosphors.

8. The information processing apparatus according to claim 1, wherein the correlation information is a spillover spreading matrix between the plurality of phosphors.

9. The information processing apparatus according to claim 1, wherein the plurality of phosphors is identified on a basis of data regarding whether a complex of a phosphor and a biomolecule is available.

10. The information processing apparatus according to claim 1, wherein the at least one processor adjusts a number of phosphors belonging to each of the brightness categories in accordance with a number of biomolecules belonging to each of the expression level categories.

11. The information processing apparatus according to claim 1, wherein the plurality of phosphors is identified on a basis of information regarding priority associated with the phosphors.

12. The information processing apparatus according to claim 1, wherein the at least one processor performs evaluation of separation capability related to the combination list.

13. The information processing apparatus according to claim 12, wherein the at least one processor further generates a modified combination list in which at least one phosphor of a set of phosphors included in the combination list is changed to another phosphor in accordance with a result of the evaluation of the separation capability and further performs separation capability evaluation related to the modified combination list.

14. The information processing apparatus according to claim 1, wherein the at least one processor further generates the combination list on a basis of cost information regarding a complex of a biomolecule and a phosphor.

15. The information processing apparatus according to claim 1, wherein in a case where a phosphor to be allocated to at least one biomolecule among the plurality of biomolecules is identified, the at least one processor further generates the combination list on a basis of correlation information between the plurality of phosphors and the phosphor identified in advance.

16. The information processing apparatus according to claim 1, wherein in a case where a light-producing substance to be used for analysis of the sample is identified, the at least one processor further generates the combination list on a basis of correlation information between the plurality of phosphors and the light-producing substance.

17. The information processing apparatus according to claim 1, wherein each of the plurality of biomolecules is an antigen or an antibody.

18. The information processing apparatus according to claim 1, wherein:

in a case where each of the plurality of biomolecules is an antigen, an expression level is an expression level of the antigen, and in a case where each of the plurality of biomolecules is an antibody, the expression level is an expression level of an antigen captured by the antibody.

19. An information processing system comprising:

an input unit that accepts an input of data regarding expression levels of a plurality of biomolecules to be used for analysis of a sample;

a processing unit that:

receives, from the input unit, an indication of the data;

obtains an indication of a plurality of phosphors usable for analysis of the sample by a spectral flow cytometer an fluorescence spectra associated with the plurality of phosphors;

generates expression level categories for the plurality of biomolecules based on expression levels in the sample, generates, based on the expression level categories, brightness categories for the plurality of phosphors based on brightness;

associates the expression level categories with the brightness categories based on the expression levels and the brightness;

generates, based on correlation information between the plurality of phosphors indicative of the fluorescence spectra associated with the plurality of phosphors, a combination list of phosphors to be used for the analysis of the sample by the spectral flow cytometer;

outputs, for display by a display device, an indication of the phosphors of the combination list respectively allocated to the biomolecules of the plurality of biomolecules;

receives, from the spectral flow cytometer, light intensity data of the plurality of biomolecules stained with the phosphors of the combination list which were respectively allocated; and deconvolutes the light intensity data based on the fluorescence spectra of the phosphors of the combination list; and the display device.

20. An information processing method comprising:

receiving an indication of a plurality of biomolecules to be used for analysis of a sample and respective expression levels of the plurality of biomolecules;

obtaining an indication of a plurality of phosphors usable for analysis of sample by a spectral flow cytometer and fluorescence spectra associated with the plurality of phosphors;

generating expression level categories for the plurality of biomolecules based on expression levels in the sample;

generating, based on the expression level categories, brightness categories for the plurality of phosphors based on brightness of the plurality of phosphors;

associating the expression level categories with the brightness categories based on the expression levels and the brightness;

generating, based on correlation information between the plurality of phosphors indicative of the fluorescence spectra associated with the plurality of phosphors, a combination list of phosphors to be used for the analysis of the sample by the spectral flow cytometer;

allocating, based on the association between the expression level categories and the brightness categories, phosphors of the combination list to biomolecules of the plurality of biomolecules;

outputting, for display by a display device, an indication of the phosphors of the combination list respectively allocated to the biomolecules of the plurality of biomolecules;

receiving light intensity data of the plurality of biomolecules stained with the phosphors of the combination list which were respectively allocated; and deconvoluting the light intensity data based on the fluorescence spectra of the phosphors of the combination list.

21. A program causing an information processing apparatus to execute a method comprising:

receiving an indication of a plurality of biomolecules to be used for analysis of a sample and respective expression levels of the plurality of biomolecules;

obtaining an indication of a plurality of phosphors usable for analysis of sample by a spectral flow cytometer and fluorescence spectra associated with the plurality of phosphors;

generating expression level categories for the plurality of biomolecules based on expression levels in the sample;

generating, based on the expression level categories, brightness categories for the plurality of phosphors based on brightness of the plurality of phosphors;

associating the expression level categories with the brightness categories based on the expression levels and the brightness;

generating, based on correlation information between the plurality of phosphors indicative of the fluorescence spectra associated with the plurality of phosphors, a combination list of phosphors to be used for the analysis of the sample by the spectral flow cytometer;

allocating, based on the association between the expression level categories and the brightness categories, phosphors of the combination list to biomolecules of the plurality of biomolecules;

outputting, for display by a display device, an indication of the phosphors of the combination list respectively allocated to the biomolecules of the plurality of biomolecules;

receiving light intensity data of the plurality of biomolecules stained with the phosphors of the combination list which were respectively allocated; and deconvoluting the light intensity data based on the fluorescence spectra of the phosphors of the combination list.

* * * * *